(12) United States Patent
Eshoo

(10) Patent No.: US 9,873,906 B2
(45) Date of Patent: Jan. 23, 2018

(54) METHODS FOR REPAIRING DEGRADED DNA

(75) Inventor: Mark W. Eshoo, Solana Beach, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 1126 days.

(21) Appl. No.: 12/900,104

(22) Filed: Oct. 7, 2010

(65) Prior Publication Data

US 2011/0086392 A1    Apr. 14, 2011

Related U.S. Application Data

(62) Division of application No. 10/891,337, filed on Jul. 14, 2004, now Pat. No. 7,811,753.

(51) Int. Cl.
  *C12Q 1/68*    (2006.01)
(52) U.S. Cl.
  CPC .................................. *C12Q 1/6806* (2013.01)
(58) Field of Classification Search
  USPC .................................................. 435/6.12, 810
  See application file for complete search history.

(56) References Cited

U.S. PATENT DOCUMENTS

| | | | |
|---|---|---|---|
| 4,075,475 A | 2/1978 | Risby et al. |
| 4,683,195 A | 7/1987 | Mullis et al. |
| 4,683,202 A | 7/1987 | Mullis |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,541,308 A | 7/1996 | Hogan et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |
| 5,707,802 A | 1/1998 | Sandhu et al. |
| 5,712,125 A | 1/1998 | Uhlen |
| 5,716,825 A | 2/1998 | Hancock et al. |
| 5,727,202 A | 3/1998 | Kucala |
| 5,745,751 A | 4/1998 | Nelson et al. |
| 5,747,246 A | 5/1998 | Pannetier et al. |
| 5,747,251 A | 5/1998 | Carson et al. |
| 5,753,467 A | 5/1998 | Jensen et al. |
| 5,753,489 A | 5/1998 | Kistner et al. |
| 5,759,771 A | 6/1998 | Tilanus |
| 5,763,169 A | 6/1998 | Sandhu et al. |
| 5,763,588 A | 6/1998 | Matteucci et al. |
| 5,770,367 A | 6/1998 | Southern et al. |
| 5,777,324 A | 7/1998 | Hillenkamp |
| 5,814,442 A | 9/1998 | Natarajan et al. |
| 5,822,824 A | 10/1998 | Dion |
| 5,828,062 A | 10/1998 | Jarrell et al. |
| 5,830,653 A | 11/1998 | Froehler et al. |
| 5,830,655 A | 11/1998 | Monforte et al. |

(Continued)

FOREIGN PATENT DOCUMENTS

| | | |
|---|---|---|
| CN | 101096704 A | 1/2008 |
| DE | 19732086 A1 | 1/1999 |

(Continued)

OTHER PUBLICATIONS

Pusch CM, Giddings I, Scholz M. Repair of degraded duplex DNA from prehistoric samples using *Escherichia coli* DNA polymerase I and T4 DNA ligase. Nucleic Acids Res. 1998. 26(3):857-9.*

Dianov G, Price A, Lindahl T. Generation of single-nucleotide repair patches following excision of uracil residues from DNA. Mol Cell Biol. 1992. 12(4):1605-12.*

Prasad R, Beard WA, Wilson SH. Studies of gapped DNA substrate binding by mammalian DNA polymerase beta. Dependence on 5'-phosphate group. J Biol Chem.1994.269(27):18096-101.*

Prasad R, Beard WA, Strauss PR, Wilson SH. Human DNA polymerase beta deoxyribose phosphate lyase. Substrate specificity and catalytic mechanism. J Biol Chem. Jun. 12, 1998;273(24):15263-70.*

(Continued)

*Primary Examiner* — Angela M Bertagna

*Assistant Examiner* — Olayinka Oyeyemi

(74) *Attorney, Agent, or Firm* — Casimir Jones, S.C.

(57) ABSTRACT

The present invention provides methods and kits for repair of degraded DNA which may then be used as a template for efficient amplification by a number of different amplification reactions. The method relies upon a series of enzymatic activities provided by DNA repair enzymes.

7 Claims, 4 Drawing Sheets

(56) References Cited

U.S. PATENT DOCUMENTS

| | | |
|---|---|---|
| 5,830,853 A | 11/1998 | Backstrom et al. |
| 5,832,489 A | 11/1998 | Kucala |
| 5,834,255 A | 11/1998 | Van Gemen et al. |
| 5,845,174 A | 12/1998 | Yasui et al. |
| 5,849,492 A | 12/1998 | Rogan |
| 5,849,497 A | 12/1998 | Steinman |
| 5,849,901 A | 12/1998 | Mabilat et al. |
| 5,851,765 A | 12/1998 | Koster |
| 5,856,174 A | 1/1999 | Lipshutz et al. |
| 5,864,137 A | 1/1999 | Becker et al. |
| 5,866,429 A | 2/1999 | Bloch |
| 5,869,242 A | 2/1999 | Kamb |
| 5,871,697 A | 2/1999 | Rothberg et al. |
| 5,872,003 A | 2/1999 | Koster |
| 5,876,936 A | 3/1999 | Ju |
| 5,876,938 A | 3/1999 | Stolowitz et al. |
| 5,885,775 A | 3/1999 | Haff et al. |
| 5,900,481 A | 5/1999 | Lough et al. |
| 5,928,905 A | 7/1999 | Stemmer et al. |
| 5,928,906 A | 7/1999 | Koster et al. |
| 5,965,363 A | 10/1999 | Monforte |
| 5,965,383 A | 10/1999 | Vogel et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 5,994,066 A | 11/1999 | Bergeron et al. |
| 6,001,564 A | 12/1999 | Bergeron et al. |
| 6,005,096 A | 12/1999 | Matteucci et al. |
| 6,007,690 A | 12/1999 | Nelson et al. |
| 6,007,992 A | 12/1999 | Lin et al. |
| 6,015,666 A | 1/2000 | Springer et al. |
| 6,018,713 A | 1/2000 | Coli et al. |
| 6,024,925 A | 2/2000 | Little et al. |
| 6,028,183 A | 2/2000 | Lin et al. |
| 6,043,031 A | 3/2000 | Koster et al. |
| 6,046,005 A | 4/2000 | Ju et al. |
| 6,051,378 A | 4/2000 | Monforte et al. |
| 6,054,278 A | 4/2000 | Dodge et al. |
| 6,055,487 A | 4/2000 | Margery et al. |
| 6,060,246 A | 5/2000 | Summerton et al. |
| 6,061,686 A | 5/2000 | Gauvin et al. |
| 6,063,031 A | 5/2000 | Cundari et al. |
| 6,074,823 A | 6/2000 | Koster |
| 6,074,831 A | 6/2000 | Yakhini et al. |
| 6,090,558 A | 7/2000 | Butler et al. |
| 6,104,028 A | 8/2000 | Hunter et al. |
| 6,110,710 A | 8/2000 | Smith et al. |
| 6,111,251 A | 8/2000 | Hillenkamp |
| 6,133,436 A | 10/2000 | Koster et al. |
| 6,140,053 A | 10/2000 | Koster |
| 6,146,144 A | 11/2000 | Fowler et al. |
| 6,146,854 A | 11/2000 | Koster et al. |
| 6,153,389 A | 11/2000 | Haarer et al. |
| 6,159,681 A | 12/2000 | Zebala |
| 6,180,339 B1 | 1/2001 | Sandhu et al. |
| 6,180,372 B1 | 1/2001 | Franzen |
| 6,187,842 B1 | 2/2001 | Kobayashi et al. |
| 6,194,144 B1 | 2/2001 | Koster |
| 6,197,498 B1 | 3/2001 | Koster |
| 6,214,555 B1 | 4/2001 | Leushner et al. |
| 6,218,118 B1 | 4/2001 | Sampson et al. |
| 6,221,587 B1 | 4/2001 | Ecker et al. |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,476 B1 | 5/2001 | Bergmann et al. |
| 6,235,478 B1 | 5/2001 | Koster |
| 6,235,480 B1 | 5/2001 | Shultz et al. |
| 6,238,871 B1 | 5/2001 | Koster |
| 6,238,927 B1 | 5/2001 | Abrams et al. |
| 6,239,159 B1 | 5/2001 | Brown et al. |
| 6,258,538 B1 | 7/2001 | Koster et al. |
| 6,261,769 B1 | 7/2001 | Everett et al. |
| 6,265,716 B1 | 7/2001 | Hunter et al. |
| 6,265,718 B1 | 7/2001 | Park et al. |
| 6,266,131 B1 | 7/2001 | Hamada et al. |
| 6,266,144 B1 | 7/2001 | Li |
| 6,268,129 B1 | 7/2001 | Gut et al. |
| 6,268,131 B1 | 7/2001 | Kang et al. |
| 6,268,144 B1 | 7/2001 | Koster |
| 6,268,146 B1 | 7/2001 | Shultz et al. |
| 6,270,973 B1 | 8/2001 | Lewis et al. |
| 6,270,974 B1 | 8/2001 | Shultz et al. |
| 6,274,316 B1 | 8/2001 | Modrusan |
| 6,274,726 B1 | 8/2001 | Laugharn, Jr. et al. |
| 6,277,573 B1 | 8/2001 | Koster |
| 6,277,578 B1 | 8/2001 | Shultz et al. |
| 6,277,634 B1 | 8/2001 | McCall et al. |
| 6,300,076 B1 | 10/2001 | Koster |
| 6,303,297 B1 | 10/2001 | Lincoln et al. |
| 6,312,893 B1 | 11/2001 | Van Ness et al. |
| 6,312,902 B1 | 11/2001 | Shultz et al. |
| 6,322,970 B1 | 11/2001 | Little et al. |
| 6,361,940 B1 | 3/2002 | Van Ness et al. |
| 6,372,424 B1 | 4/2002 | Brow et al. |
| 6,389,428 B1 | 5/2002 | Rigault et al. |
| 6,391,551 B1 | 5/2002 | Shultz et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,428,956 B1 | 8/2002 | Crooke et al. |
| 6,432,651 B1 | 8/2002 | Hughes et al. |
| 6,436,635 B1 | 8/2002 | Fu et al. |
| 6,436,640 B1 | 8/2002 | Simmons et al. |
| 6,453,244 B1 | 9/2002 | Oefner |
| 6,458,533 B1 | 10/2002 | Felder et al. |
| 6,468,743 B1 | 10/2002 | Romick et al. |
| 6,468,748 B1 | 10/2002 | Monforte et al. |
| 6,475,143 B2 | 11/2002 | Iliff |
| 6,475,736 B1 | 11/2002 | Stanton, Jr. |
| 6,475,738 B2 | 11/2002 | Shuber et al. |
| 6,479,239 B1 | 11/2002 | Anderson et al. |
| 6,500,621 B2 | 12/2002 | Koster |
| 6,553,317 B1 | 4/2003 | Lincoln et al. |
| 6,558,902 B1 | 5/2003 | Hillenkamp |
| 6,563,025 B1 | 5/2003 | Song et al. |
| 6,566,055 B1 | 5/2003 | Monforte et al. |
| 6,568,055 B1 | 5/2003 | Tang et al. |
| 6,582,916 B1 | 6/2003 | Schmidt et al. |
| 6,586,584 B2 | 7/2003 | McMillian et al. |
| 6,589,485 B2 | 7/2003 | Koster |
| 6,602,662 B1 | 8/2003 | Koster et al. |
| 6,605,433 B1 | 8/2003 | Fliss et al. |
| 6,610,492 B1 | 8/2003 | Stanton, Jr. et al. |
| 6,613,509 B1 | 9/2003 | Chen |
| 6,613,520 B2 | 9/2003 | Ashby |
| 6,617,137 B2 | 9/2003 | Dean et al. |
| 6,623,928 B2 | 9/2003 | Van Ness et al. |
| 6,638,714 B1 | 10/2003 | Linnen et al. |
| 6,680,476 B1 | 1/2004 | Hidalgo et al. |
| 6,682,889 B1 | 1/2004 | Wang et al. |
| 6,705,530 B2 | 3/2004 | Kiekhaefer |
| 6,706,530 B2 | 3/2004 | Hillenkamp |
| 6,712,157 B2 | 3/2004 | Hansson |
| 6,723,510 B2 | 4/2004 | Lubenow et al. |
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,933,244 B2 | 8/2005 | Goodhue |
| 6,977,148 B2 | 12/2005 | Dean et al. |
| 6,994,962 B1 | 2/2006 | Thilly |
| 7,007,614 B2 | 3/2006 | Gaunt et al. |
| 7,022,835 B1 | 4/2006 | Rauth et al. |
| 7,024,370 B2 | 4/2006 | Epler et al. |

(56) References Cited

U.S. PATENT DOCUMENTS

| | | |
|---|---|---|
| 7,067,352 B1 | 6/2006 | Scheid |
| 7,108,974 B2 | 9/2006 | Ecker et al. |
| 7,181,009 B1 | 2/2007 | Huxel |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,501,251 B2 | 3/2009 | Köster et al. |
| 7,535,893 B1 | 5/2009 | Beladakere et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 2001/0039263 A1 | 11/2001 | Matthes et al. |
| 2002/0006611 A1 | 1/2002 | Portugal et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0119018 A1 | 6/2003 | Omura et al. |
| 2003/0129589 A1 | 7/2003 | Koster et al. |
| 2003/0129624 A1* | 7/2003 | Eastman ............ C12N 15/1096 435/6.12 |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 | 7/2004 | Lasken et al. |
| 2004/0137013 A1 | 7/2004 | Katinger et al. |
| 2004/0185438 A1 | 9/2004 | Ecker |
| 2004/0191769 A1 | 9/2004 | Marino et al. |
| 2004/0202577 A1 | 10/2004 | McNeil et al. |
| 2004/0202997 A1 | 10/2004 | Ecker et al. |
| 2004/0209260 A1 | 10/2004 | Ecker et al. |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130196 A1 | 6/2005 | Hofstadler et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler |
| 2006/0020391 A1 | 1/2006 | Kreiswirth et al. |
| 2006/0121520 A1 | 6/2006 | Ecker et al. |
| 2006/0172330 A1 | 8/2006 | Osborn et al. |
| 2006/0205040 A1 | 9/2006 | Sampath |
| 2006/0240412 A1 | 10/2006 | Hall et al. |
| 2006/0259249 A1 | 11/2006 | Sampath et al. |
| 2007/0134652 A1 | 6/2007 | Slepnev et al. |
| 2007/0174654 A1 | 7/2007 | Berman et al. |
| 2007/0207453 A1 | 9/2007 | Gupta et al. |
| 2007/0218467 A1 | 9/2007 | Ecker et al. |
| 2007/0218489 A1 | 9/2007 | Sampath et al. |
| 2008/0160512 A1 | 7/2008 | Ecker et al. |
| 2008/0233570 A1 | 9/2008 | Hall et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0092977 A1 | 4/2009 | Koster |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |
| 2010/0070194 A1 | 3/2010 | Ecker et al. |
| 2010/0145626 A1 | 6/2010 | Ecker et al. |
| 2010/0184035 A1 | 7/2010 | Hall et al. |

FOREIGN PATENT DOCUMENTS

| | | |
|---|---|---|
| DE | 19802905 A1 | 7/1999 |
| DE | 19824280 A1 | 12/1999 |
| DE | 19852167 A1 | 5/2000 |
| DE | 19943374 A1 | 3/2001 |
| DE | 10132147 A1 | 2/2003 |
| EP | 281390 A2 | 9/1988 |
| EP | 0620862 A1 | 10/1994 |
| EP | 633321 A1 | 1/1995 |

(56) References Cited

FOREIGN PATENT DOCUMENTS

| | | |
|---|---|---|
| EP | 620862 B1 | 4/1998 |
| EP | 1035219 A1 | 9/2000 |
| EP | 1138782 A2 | 10/2001 |
| EP | 1234888 A2 | 8/2002 |
| EP | 1308506 A1 | 5/2003 |
| EP | 1310571 A2 | 5/2003 |
| EP | 1333101 A1 | 8/2003 |
| EP | 1365031 A1 | 11/2003 |
| EP | 1234888 A3 | 1/2004 |
| EP | 1460431 A2 | 9/2004 |
| EP | 1541696 A1 | 6/2005 |
| EP | 1748072 A1 | 1/2007 |
| FR | 2811321 A1 | 1/2002 |
| GB | 2325002 A | 11/1998 |
| GB | 2339905 A | 2/2000 |
| JP | 5276999 A2 | 10/1993 |
| JP | 11137259 A | 5/1999 |
| JP | 24024206 A2 | 1/2004 |
| JP | 2004000200 A2 | 1/2004 |
| JP | 24201679 A2 | 7/2004 |
| JP | 2004201641 A | 7/2004 |
| KR | 20080029726 A | 4/2008 |
| RU | 2205876 C1 | 6/2003 |
| WO | WO8803957 A1 | 6/1988 |
| WO | WO9015157 A1 | 12/1990 |
| WO | WO9205182 A1 | 4/1992 |
| WO | WO9208117 A1 | 5/1992 |
| WO | WO9209703 A1 | 6/1992 |
| WO | WO9219774 A1 | 11/1992 |
| WO | WO9303186 A1 | 2/1993 |
| WO | WO9305182 A1 | 3/1993 |
| WO | WO9308297 A1 | 4/1993 |
| WO | WO9416101 A2 | 7/1994 |
| WO | WO9419490 A1 | 9/1994 |
| WO | WO9421822 A1 | 9/1994 |
| WO | WO9504161 A1 | 2/1995 |
| WO | WO9511996 A1 | 5/1995 |
| WO | WO9513395 A1 | 5/1995 |
| WO | WO9513396 A2 | 5/1995 |
| WO | WO9531997 A1 | 11/1995 |
| WO | WO9606187 A1 | 2/1996 |
| WO | WO9616186 A1 | 5/1996 |
| WO | WO9629431 A2 | 9/1996 |
| WO | WO9632504 A2 | 10/1996 |
| WO | WO9635450 A1 | 11/1996 |
| WO | WO9637630 A1 | 11/1996 |
| WO | WO9733000 A1 | 9/1997 |
| WO | WO9734909 A1 | 9/1997 |
| WO | WO9737041 A2 | 10/1997 |
| WO | WO9747766 A1 | 12/1997 |
| WO | WO9803684 A1 | 1/1998 |
| WO | WO9812355 A1 | 3/1998 |
| WO | WO9814616 A1 | 4/1998 |
| WO | WO9815652 A1 | 4/1998 |
| WO | WO9820020 A2 | 5/1998 |
| WO | WO9820157 A2 | 5/1998 |
| WO | WO9820166 A2 | 5/1998 |
| WO | WO9826095 A1 | 6/1998 |
| WO | WO9831830 A1 | 7/1998 |
| WO | WO9835057 A1 | 8/1998 |
| WO | WO9840520 A1 | 9/1998 |
| WO | WO9852047 A1 | 11/1998 |
| WO | WO9854571 A1 | 12/1998 |
| WO | WO9854751 A1 | 12/1998 |
| WO | WO9905319 A2 | 2/1999 |
| WO | WO9912040 A2 | 3/1999 |
| WO | WO9913104 A1 | 3/1999 |
| WO | WO9914375 A2 | 3/1999 |
| WO | WO9929898 A2 | 6/1999 |
| WO | WO9931278 A1 | 6/1999 |
| WO | WO9957318 A2 | 11/1999 |
| WO | WO9958713 A2 | 11/1999 |
| WO | WO9960183 A1 | 11/1999 |
| WO | WO0032750 A1 | 6/2000 |
| WO | WO0038636 A1 | 7/2000 |
| WO | WO0063362 A1 | 10/2000 |
| WO | WO0066762 A2 | 11/2000 |
| WO | WO0066789 A2 | 11/2000 |
| WO | WO0077260 A1 | 12/2000 |
| WO | WO0100828 A2 | 1/2001 |
| WO | WO0107648 A1 | 2/2001 |
| WO | WO0112853 A1 | 2/2001 |
| WO | WO0120018 A2 | 3/2001 |
| WO | WO0123604 A2 | 4/2001 |
| WO | WO0123608 A2 | 4/2001 |
| WO | WO0132930 A1 | 5/2001 |
| WO | WO0140497 A2 | 6/2001 |
| WO | WO0146404 A1 | 6/2001 |
| WO | WO0151661 A2 | 7/2001 |
| WO | WO0151662 A1 | 7/2001 |
| WO | WO0157263 A1 | 8/2001 |
| WO | WO0157518 A2 | 8/2001 |
| WO | WO0173119 A2 | 10/2001 |
| WO | WO0173199 A1 | 10/2001 |
| WO | WO0177392 A2 | 10/2001 |
| WO | WO0196388 A2 | 12/2001 |
| WO | WO0202811 A2 | 1/2002 |
| WO | WO0210186 A1 | 2/2002 |
| WO | WO0210444 A1 | 2/2002 |
| WO | WO0218641 A2 | 3/2002 |
| WO | WO0221108 A2 | 3/2002 |
| WO | WO0222873 A1 | 3/2002 |
| WO | WO0224876 A2 | 3/2002 |
| WO | WO0250307 A1 | 6/2002 |
| WO | WO02057491 A2 | 7/2002 |
| WO | WO02070664 A2 | 9/2002 |
| WO | WO02070728 A2 | 9/2002 |
| WO | WO02070737 A2 | 9/2002 |
| WO | WO02077278 A1 | 10/2002 |
| WO | WO02099034 A2 | 12/2002 |
| WO | WO02099095 A2 | 12/2002 |
| WO | WO02099129 A2 | 12/2002 |
| WO | WO02099130 A2 | 12/2002 |
| WO | WO03001976 A2 | 1/2003 |
| WO | WO03002750 A2 | 1/2003 |
| WO | WO03008636 A2 | 1/2003 |
| WO | WO03012058 A2 | 2/2003 |
| WO | WO03012074 A2 | 2/2003 |
| WO | WO03014382 A2 | 2/2003 |
| WO | WO03016546 A1 | 2/2003 |
| WO | WO03018636 A2 | 3/2003 |
| WO | WO03020890 A2 | 3/2003 |
| WO | WO03033732 A2 | 4/2003 |
| WO | WO03050269 A2 | 6/2003 |
| WO | WO03054162 A2 | 7/2003 |
| WO | WO03054755 A2 | 7/2003 |
| WO | WO03060163 A2 | 7/2003 |
| WO | WO03075955 A1 | 9/2003 |
| WO | WO03088979 A2 | 10/2003 |
| WO | WO03093506 A2 | 11/2003 |
| WO | WO03097869 A2 | 11/2003 |
| WO | WO03100035 A2 | 12/2003 |
| WO | WO03100068 A1 | 12/2003 |
| WO | WO03102191 A1 | 12/2003 |
| WO | WO03104410 A2 | 12/2003 |
| WO | WO03106635 A2 | 12/2003 |
| WO | WO04003511 A2 | 1/2004 |
| WO | WO04009849 A1 | 1/2004 |
| WO | WO04011651 A1 | 2/2004 |
| WO | WO04013357 A2 | 2/2004 |
| WO | WO04040013 A1 | 5/2004 |
| WO | WO04044123 A2 | 5/2004 |
| WO | WO04044247 A2 | 5/2004 |
| WO | WO04052175 A2 | 6/2004 |
| WO | WO04053076 A2 | 6/2004 |
| WO | WO04053141 A2 | 6/2004 |
| WO | WO04053164 A2 | 6/2004 |
| WO | WO04060278 A2 | 7/2004 |
| WO | WO04070001 A2 | 8/2004 |
| WO | WO04072230 A2 | 8/2004 |
| WO | WO04072231 A2 | 8/2004 |
| WO | WO04101809 A2 | 11/2004 |
| WO | WO05003384 A1 | 1/2005 |
| WO | WO05005659 A1 | 1/2005 |

(56) References Cited

FOREIGN PATENT DOCUMENTS

| WO | WO2005-017173 | * | 2/2005 | ............ C12P 19/34 |
|----|----|----|----|----|
| WO | WO05009202 A2 | | 2/2005 | |
| WO | WO05012572 A1 | | 2/2005 | |
| WO | WO05024046 A2 | | 3/2005 | |
| WO | WO05036369 A2 | | 4/2005 | |
| WO | WO05054454 A1 | | 6/2005 | |
| WO | WO05075686 A1 | | 8/2005 | |
| WO | WO05086634 A2 | | 9/2005 | |
| WO | WO05091971 A2 | | 10/2005 | |
| WO | WO05094421 A2 | | 10/2005 | |
| WO | WO05098047 A2 | | 10/2005 | |
| WO | WO05116263 A2 | | 12/2005 | |
| WO | WO06089762 A1 | | 8/2006 | |
| WO | WO06094238 A2 | | 9/2006 | |
| WO | WO06102416 A2 | | 9/2006 | |
| WO | WO06135400 A2 | | 12/2006 | |
| WO | WO2007014045 A2 | | 2/2007 | |
| WO | WO2007086904 A2 | | 8/2007 | |
| WO | WO2007100397 A2 | | 9/2007 | |
| WO | WO2007106407 A2 | | 9/2007 | |
| WO | WO2008104002 A2 | | 8/2008 | |
| WO | WO2008118809 A1 | | 10/2008 | |

OTHER PUBLICATIONS

Singhal RK, Prasad R, Wilson SH. DNA polymerase beta conducts the gap-filling step in uracil-initiated base excision repair in a bovine testis nuclear extract. J Biol Chem. 1995. 270(2):949-57.*
Wallace SS, Bandaru V, Kathe SD, Bond JP. The enigma of endonuclease VIII. DNA Repair (Amst). 2003. 2(5):441-53. Review.*
Srivastava DK, Berg BJ, Prasad R, Molina JT, Beard WA, Tomkinson AE, Wilson SH. Mammalian abasic site base excision repair. Identification of the reaction sequence and rate-determining steps. J Biol Chem. 1998. 273(33):21203-9.*
New England Biolabs (NEB) technical bulletin, 2012.*
Life Technologies Technical Bulletin, 2012.*
Bailly V, Verly WG. AP endonucleases and AP lyases. Nucleic Acids Res. May 11, 1989; 17(9):3617-8.*
Dean FB, Nelson JR, Giesler TL, Lasken RS. Rapid amplification of plasmid and phage DNA using Phi 29 DNA polymerase and multiply-primed rolling circle amplification. Genome Res. Jun. 2001; 11(6):1095-9.*
Izumi T, Wiederhold LR, Roy G, Roy R, Jaiswal A, Bhakat KK, Mitra S, Hazra TK. Mammalian DNA base excision repair proteins: their interactions and role in repair of oxidative DNA damage. Toxicology. Nov. 15, 2003; 193(1-2):43-65.*
Fpg (New England Biolabs catalog # M0240S) retrieved Jan. 7, 2016 https://www.neb.com/~/media/Catalog/All-Products/AA6D9289524B400D89BDB9B79EFE164E/Datacards or Manuals/M0240Datasheet-Lot0041205.pdf.*
T4 polynucleotide kinase (New England Biolabs catlog M0201S) retrieved Dec. 21, 2015 from https://www.neb.com/~/media/Catalog/All-Products/96F1AABD36E2412F858AB6375181E2C2/Datacards or Manuals/M0201Datasheet-Lot0911203.pdf.*
T4 DNA ligase (New England Biolabs catalog # M0202S) retrieved Dec. 21, 2015 from https://www.neb.com/~/media/Catalog/All-Products/CB1C82A631A344BE823E9F201B1516C5/Datacards or Manuals/M0202Datasheet-Lot1011202.pdf.*
Carvalho, Felicia, and Marc E. Gillespie. Bringing proteomics into the lab: Proteomics lab 101. Biochemistry and Molecular Biology Education 31, No. 1 (2003): 46-51.*
NEB T4 DNA ligase products retrieved Jan. 7, 2016 from http://international.neb.com/products/m0202-t4-dna-ligase.*
Rossi R, Montecucco A, Ciarrocchi G, Biamonti G. Functional characterization of the T4 DNA ligase: a new insight into the mechanism of action. Nucleic Acids Res. Jun. 1, 1997; 25(11):2106-13.*
Nealon K, Nicholl ID, Kenny MK. Characterization of the DNA polymerase requirement of human base excision repair. Nucleic Acids Res. Oct. 1, 1996;24(19):3763-70.*

Ecker Supporting Information [online], May 23, 2005 [retrieved on Jul. 31, 2011]. Retrieved from the Internet:<URL: http://www.pnas.org/content/102/22/8012/suppl/DC1>.
Aaserud D.J., et al., "Accurate Base Composition of Double-Strand DNA by Mass Spectrometry," American Society for Mass Spectrometry, 1996, vol. 7 (12), pp. 1266-1269.
Aaserud D.J., et al., "DNA Sequencing with Blackbody Infrared Radioactive Dissociation of Electrosprayed Ions," International Journal of Mass Spectrometry and Icon Processes, 1997, vol. 167/168, pp. 705-712.
Abdi F.A., et al., "Validation of DNA Sequences Using Mass Spectrometry Coupled with Nucleoside Mass Tagging," Genome Research, 2002, vol. 12 (7), pp. 1135-1141.
Adam E., et al., "Characterization of Intertype Specific Epitopes on Adenovirus Hexons," Archives of Virology, 1998, vol. 143 (9), pp. 1669-1682.
Adam E., et al., "Intertype Specific Epitope Structure of Adenovirus Hexon," Acta Microbiologica et Immunologica Hungarica, 1998, vol. 45 (3-4), pp. 311-316.
Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.
Adrian T., et al., "DNA Restriction Analysis of Adenovirus Prototypes 1 to 41," Archives of Virology, 1986, vol. 91 (3-4), pp. 277-290.
Adzhar A., et al., "Universal Oligonucleotides for the Detection of Infectious Bronchitis Virus by Thepolymerase Chain Reaction," Avian Pathology, 1996, vol. 25 (4), pp. 817-836.
Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.
Aires De Sousa M., et al., "Bridges from Hospitals to the Laboratory: Genetic Portraits of Methicillin-Resistant *Staphylococcus aureus* Clones," FEMS Immunology and Medical Microbiology, 2004, vol. 40 (2), pp. 101-111.
Akalu A., et al., "Rapid Identification of Subgenera of Human Adenovirus by Serological and PCR Assays," Journal of Virological Methods, 1998, vol. 71 (2), pp. 187-196.
Alamgir A.S., et al., "Phylogenetic Analysis of Influenza C Virus Nonstructural (NS) Protein Genes and Identification of the NS2 Protein," The Journal of General Virology, 2000, vol. 81 (pt 8), pp. 1933-1940.
Alba M.M., et al., "VIDA: A Virus Database System for the Organization of Animal Virus Genome Open Reading Frames," Nucleic Acids Research, 2001, vol. 29 (1), pp. 133-136.
Allaouchiche B., et al., "Clinical Impact of Rapid Oxacillin Susceptibility Testing Using a PCR Assay in *Staphylococcus aureus* Bactaeremia," The Journal of Infection, 1999, vol. 39 (3), pp. 198-204.
Allawi H.T., et al., "Thermodynamics and NMR of Internal G.T. Mismatches in DNA," Biochemistry, 1997, vol. 36 (34), pp. 10581-10594.
Altschuel S.F., et al., "Basic Local Alignment Search Tool," Journal of Molecular Biology, 1990, vol. 215 (3), pp. 403-410.
Altschuel S.F., et al., "Gapped BLAST and PSI-BLAST: A New Generation of Protein Database Search Programs," Nucleic Acids Research, 1997, vol. 25 (17), pp. 3389-3402.
Alves-Silva J., et al., "The Ancestry of Brazilian mtDNA Linages," The American Journal of Human Genetics, 2000, vol. 67 (2), pp. 444-461.
Amano Y., et al., "Detection of Influenza Virus: Traditional Approaches and Development of Biosensors," Analytical and Bioanalytical Chemistry, 2005, vol. 381 (1), pp. 156-164.
Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.
Anderson M.L.M., "Quantitative Filter Hybridization" in: Nucleic Acid Hybridization, Hames B.D., ed., IRL Press, 1985, pp. 73-111.

(56) References Cited

OTHER PUBLICATIONS

Anderson S., et al., "Sequence and Organization of the Human Mitochondrial Genome," Nature, 1981, vol. 290 (5806), pp. 457-465.

Andreasson H., et al., "Mitochondrial Sequence Analysis for Forensic Identification Using Pyrosequencing Technology," BioTechniques, 2002, vol. 32 (1), pp. 124-133.

Anthony R.M., et al., "Use of the Polymerase Chain Reaction for Rapid Detection of High-Level Mupirocin Resistance in Staphylococci," European Journal of Clinical Microbiology & Infectious Diseases, 1999, vol. 18 (1), pp. 30-34.

Arbique J., et al., "Comparison of the Velogene Rapid MRSA Identification Assay, Denka MRSAScreen Assay, and BBL Crystal MRSA ID System for Rapid Identification of Methicillin-Resistant Staphylococcus aureus," Diagnositic Microbiology and Infectious Diseases, 2001, vol. 40 (1-2), pp. 5-10.

Archer G.L., et al., "Detection of Methicillin Resistance in Staphylococci by Using a DNA Probe," Antimicrobial Agents and Chemotherapy, 1990, vol. 34 (9), pp. 1720-1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

Arnal C., et al., "Quantification of Hepatitis A Virus in Shellfish by Competitive Reverse Transcription PCR with Coextraction of Standard RNA," Applied and Environmental Microbiology, 1999, vol. 65 (1), pp. 322-326.

Aronsson F., et al., "Persistence of the Influenza A/WSN/33 Virus RNA at Midbrain Levels of Immunodefective Mice," Journal of Neurovirology, 2001, vol. 7 (2), pp. 117-124.

Ausubel F.M., et al., Eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.

Avellon A., et al., "Rapid and Sensitive Diagnosis of Human Adenovirus Infections by a Generic Polymerase Chain Reaction," Journal of Virological Methods, 2001, vol. 92 (2), pp. 113-120.

Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.

Baba T., et al., "Genome and Virulence Determinants of High Virulence Community-Acquired MRSA," Lancet, 2002, vol. 359 (9320), pp. 1819-1827.

Bahrmahd A.R., et al., "Polymerise Chain Reaction of Bacterial Genomes with Single Universal Primer: Application to Distinguishing Mycobacteria Species," Molecular and Cellular Probes, 1996, vol. 10 (2), pp. 117-122.

Bahrmahd A.R., et al., "Use of Restriction Enzyme Analysis of Amplified DNA Coding for the hsp65 Gene and Polymerase Chain Reaction with Universal Primer for Rapid Differtiation of Mycobacterium Species in the Clinical Laboratory," Scandinavian Journal of Infectious Diseases, 1998, vol. 30 (5), pp. 477-480.

Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.

Baker G.C., et al., "Review and Re-Analysis of Domain-Specific 16S Primers," Journal of Microbiological Methods, 2003, vol. 55 (3), pp. 541-555.

Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.

Barbour A.G., et al., "Identification of an Uncultivatable Borrelia Species in the Hard Tick Amblyomma Americanum: Possible Agent of a Lyme Disease-Like Illness," The Journal of Infectious Diseases, 1996, vol. 173 (2), pp. 403-409.

Barns S.M., et al., "Detection of Diverse New Francisella-like Bacteria in Environmental Samples," Applied and Environmental Microbiology, 2005, vol. 71 (9), pp. 5494-5500.

Baron E.J., "Genetic Aspects of Methicillin Resistance in Staphylococcus aureus and MethodsUsed for its Detection in Clinical Laboratories in the United States," Journal of Chemotherapy, 1995, vol. 7 (Suppl. 3), pp. 87-92.

Barr I.G., et al., "An Influenza A(H3) Reassortant was Epidemic in Australia and New Zealand in 2003," Journal of Medical Virology, 2005, vol. 76 (3), pp. 391-397.

Barski P., et al., "Rapid Assay for Detection of Methicillin-Resistant Staphylococcus aureus Using Multiplex PCR," Molecular and Cellular Probes, 1996, vol. 10 (6), pp. 471-475.

Bastia T., et al., "Organelle DNA Analysis of Solanum and Brassica Somatic Hybrids by PCR with Universal Primers," Theoretical and Applied Genetics, 2001, vol. 102 (8), pp. 1265-1272.

Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.

Beall B., et al., "Sequencing emm-Specific PCR Products for Routine andAccurate Typing of Group A Streptococci," Journal of Clincal Microbiology, 1996, vol. 34 (4), pp. 953-958.

Beall B., et al., "Survey of emm Gene Sequences and T-Antigen Types from Systemic Streptococcus pyogenes Infection Isolates Collected in San Francisco, California; Atlanta, Georgia; and Connecticut in 1994 and 1995," Journal of Clincal Microbiology, 1997, vol. 35 (5), pp. 1231-1235.

Belanger S.D., et al., "Rapid Detection of Clostridium Difficile in Feces by Real-Time PCR," Journal of Clinical Microbiology, 2003, vol. 41 (2), pp. 730-734.

Benko, M. et al., "Family Adenoviridae," Virus taxonomy. VIIIth report of the International Committee on Taxonomy of Viruses, 2004, Academic Press, New York, pp. 213-228.

Benson D.A., et al., "GenBank," Nucleic Acids Research, 1999, vol. 27 (1), pp. 12-17.

Benson L.M., et al, "Advantages of Thermococcus Kodakaraenis (KOD) DNA Polymerase for PCR-Mass Spectrometry Based Analyses," American Society for Mass Spectrometry, 2003, vol. 14 (6), pp. 601-604.

Berencsi G., et al., "Molecular Biological Characterization of Adenovirus DNA," Acta Microbiologica et Immunologica Hungarica, 1998, vol. 45 (3-4), pp. 297-304.

Bishop M.J., et al., "Molecular Sequence Databases" in: Nucleic Acid and Protein Sequence Analysis, 4th Chapter, Bishop M.J., et al., Eds, IRL Press, 1987, pp. 83-113.

Bisno A.L., "Streptococcus pyogenes" in: Infectious Diseases and Their Etiologic Agents, vol. 2, Mandell, Eds., Churchill Livingston, New York, pp. 1786-1799.

Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.

Blaiotta G., et al., "PCR Detection of Staphylococcal Enterotoxin Genes in Staphylococcus spp. Strains Isolated from Meat and Dairy Products. Evidence for New Variants of seG and Sel in S. aureus AB-8802," Journal of Applied Microbiology, 2004, vol. 97 (4), pp. 719-730.

BLAST Search results, Mar. 7, 2006.

Boivin-Jahns V., et al., "Bacterial Diversity in a Deep-Subsurface Clay Environment," Applied and Environmental Microbiology, 1996. vol. 62 (9), pp. 3405-3412.

Bolton E.T., et al., "A General Method for the Isolation of RNA Complementary to DNA," Proceedings of the National Academy of Sciences, 1962, vol. 48, pp. 1390-1397.

(56) References Cited

OTHER PUBLICATIONS

Bonk T., et al., "Matrix Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.
Borrow R., et al., "SiaD PCR Elisa for Confirmation and Identification of Serogroup Y and W135 Meningococcal Infections," FEMS Microbiology Letters, 1998, vol. 159 (2), pp. 209-214.
Boubaker K., et al., "Panton-Valentine Leukocidin and Staphylococcal Skin Infections in Schoolchildren," Emerging Infectious Diseases, 2004, vol. 10 (1), pp. 121-124.
Bowen J.E., et al., "The Native Virulence Plasmid Combination Affects the Segregational Stability of a Thetareplicating Shuttle Vector in *Bacillus anthracis* var," Journal of Applied Microbiology, 1999, vol. 87 (2), pp. 270-278.
Bowers K.M., et al., "Screening for Methicillin Resistance in *Staphylococars aureus* and Coagulasenegative Staphylococci: Evaluation of Three Selective and Mastalex-MRSA latex Agglutination," British Journal of Biomedical Science, 2003, vol. 60 (2), pp. 71-74.
Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.
Brakstad O.G., et al., "Multiplex Polymerase Chain Reaction for Detection of Genes for *Staphylococcus aureus* Themonuclease and Methicillin Resistance and Correlation with Oxacillin Resistance," Acta Pathologica, Microbiologica et Immunologica Scandinavica, 1993, vol. 101 (9), pp. 681-688.
Brandal L.T., et al., "Octaplex PCR and Fluorescence-Based Capillary Electrophoresis for Identification of Human Diarrheagenic *Escherichia coli* and *Shigella* spp," Journal of Microbiological Methods, 2007, vol. 68 (2), pp. 331-341.
Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.
Brayshaw D.P., "Methicillin-Resistant *Staphylococcus aureus*: Evaluation of Detection Techniques on Laboratory-Passaged Organisms," British Journal of Biomedical Science, 1999, vol. 56 (3), pp. 170-176.
Brightwell G., et al., "Development of Internal Controls for PCR Detection of Bacillus Anthracis," Molecular and Cellular Probes, 1998, vol. 12 (6), pp. 367-377.
Brightwell G., et al., "Genetic Targets for the Detection and Identifiaction of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.
Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the *Arabidopsis* Genome Depends on Sequence of Pre-Insertion Sites," EMBO Reports, 2002, vol. 3 (12), pp. 1152-1157.
Buck G.A., et al., "Design Strategies and Performance of Custom DNA Sequencing Primers," BioTechniques, 1999, vol. 27 (3), pp. 528-536.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.
Butler J.M., et al., High Throughput Genotyping of Forensic STRs and SNPs using Time-of-Flight Mass Spectrometry, 9th International Symposium on Human Identification, 1998, Orlando FL.
Campbell W.P., et al., "Detection of California Serogroup Bunyavirus in Tissue Culture and Mosquito Pools by PCR," Journal of Virological Methods, 1996, vol. 57 (2), pp. 175-179.
Carracedo A., et al., "DNA Commission of the International Society for Forensic Genetics: Guidelines Formitochondrial DNA Typing," Forensic Science International, 2000, vol. 110 (2), pp. 79-85.
Carroll K.C., et al., "Rapid Detection of the Staphylococcal mecA Gene from BACTEC BloodCulture Bottles by the Polymerase Chain Reaction," American Journal of Clincal Pathology, 1996, vol. 106 (5), pp. 600-605.
Case J.T., et al., "Maternal Inheritance of Mitochondrial DNA Polymorphisms in Cultured Human Fibroblasts," Somatic Cell Genetics, 1981, vol. 7 (1), pp. 103-108.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.
Certificate of Correction dated Jan. 6, 2009 for U.S. Appl. No. 10/660,996, filed Sep. 12, 2003.
Certificate of Correction dated Aug. 7, 2007 for U.S. Appl. No. 10/660,997, filed Sep. 12, 2003.
Certificate of Correction dated Dec. 12, 2006 for U.S. Appl. No. 10/156,608, filed May 24, 2002.
Certificate of Correction dated Jul. 17, 2007 for U.S. Appl. No. 09/891,793, filed Jun. 26, 2001.
Certificate of Correction dated Mar. 31, 2008 for U.S. Appl. No. 09/891,793, filed Jun. 26, 2001.
Certificate of Correction dated Mar. 31, 2008 for U.S. Appl. No. 10/156,608, filed May 24, 2002.
Certificate of Correction dated Mar. 31, 2008 for U.S. Appl. No. 10/660,997, filed Sep. 12, 2003.
Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.
Chamberlin M., et al., "New RNA Polymerase from *Escerichia coli* Infected with Bacteriophage T7," Nature, 1970, vol. 228 (5268), pp. 227-231.
Chandra S., et al., "Virus Reduction in the Preparation and Intravenous Globulin: In Vitro Experiments," Transfusion, 1999, vol. 39 (3), pp. 249-257.
Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chaves F., et al., "Molecular Characterization of Resistance to Mupirocin in Methicillin-Susceptible and -Resistant Isolates of *Staphylococcus aureus* from Nasal Samples," Journal of Clinical Microbiology, 2004, vol. 42 (2), pp. 822-824.
Chelly J., et al., "Transcription of the Dystrophin Gene in Human Muscle and Non-Muscle Tissue," Nature, 1988, vol. 333 (6176), pp. 858-860.
Chen C.A., et al., "Universal Primers for Amplification of Mitochondrial Small Subunit Ribosomal RNA-Encoding Gene in Scleractinian Corals," Marine Biotechnology, 2000, vol. 2 (2), pp. 146-153.

(56) References Cited

OTHER PUBLICATIONS

Chen C.H., et al., Laser Desorption Mass Spectrometry for FastDNA Sequencing [online], Nov. 1994, Retrieved from the Internet:< URL:http://www.ornl.gove/sci/techresources/Human_Genome/publicat/94SANTA/sequencing/seqtoc.shtml>.
Chen J., et al., "A Universal PCR Primer to Detect Members of the Potyviridae and its Use to Examine the Taxonomic Status of Several Members of the Family," Archives of Virology, 2001, vol. 146 (4), pp. 757-766.
Chen N., et al., "The Genomic Sequence of Ectromelia Virus, the Causative Agent of Mousepox," Virology, 2003, vol. 317 (1), pp. 165-186.
Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.
Chen Y.Z., et al., "A BAC-Based STS-Content Map Spanning a 35-Mb Region of Human Chromosome 1p35-36," Genomics, 2001, vol. 74 (1), pp. 55-70.
Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.
Chieochansin T., et al., "Complete Coding Sequences and Phylogenetic Analysis of Human Bocavirus (HBoV)," Virus Research, 2007, vol. 129 (1), pp. 54-57.
Chiu N.H., et al., "Mass Spectrometry of Single-Stranded Restriction Fragments Captured by an Undigested Complementary Sequence," Nucleic Acids Research, 2000, vol. 28 (8), pp. E31.
Chmielewicz B., et al., "Development of a PCR-Based Assay for Detection, Quantification, and Genotyping of Human Adenoviruses," Clinical Chemistry, 2005, vol. 51 (8), pp. 1365-1373.
Cho M., et al., "Application of the Ribonuclease P (RNaseP) RNA Gene Sequence for Phylogenetic Analysis of the Genus *Saccharomonospora*," International Journal of Systematic Bacteriology, 1998, vol. 48 (4), pp. 1223-1230.
Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1N1, H1 N2 and H3N2 Viruses in Clinical Samples Using Two Multiplex RT-PCR Assays," Journal of Virological Methods, 2002, vol. 102 (1-2), pp. 53-59.
Chomvarin C., et al., "Characterization of Diarrheagenic *Escherichia coli* isolated from Food in Khon Kaen, Thailand," The Southeast Asian Journal of Tropical Medicine and Public Health, 2005, vol. 36 (4), pp. 931-939.
Christel L.A., et al., "Rapid, Automated Nucleic Acid Probe Assays Using Silicon Microstructures for Nucleic Acid Concentration," Journal of Biomechanical Engineering, 1999, vol. 121 (1), pp. 22-27.
Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.
Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.
Collins D.W., et al., "Numerical Classification of Coding Sequences," Nucleic Acids Research, 1992, vol. 20 (6), pp. 1405-1410.
Conrads G., et al., "16S-23S rDNA Internal Transcribed Spacer Sequences for Analysis of the Phylogenetic Relationships Among Species of the Genus *Fusobacterium*," International Journal of Systematic and Evolutionary Microbiology, 2002, vol. 52 (2), pp. 493-499.
Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,463, filed Dec. 13, 2002.
Co-pending U.S. Appl. No. 10/323,186, filed Dec. 18, 2002.
Co-pending U.S. Appl. No. 10/323,187, filed Dec. 18, 2002.
Co-pending U.S. Appl. No. 10/324,721, filed Dec. 18, 2002.
Co-pending U.S. Appl. No. 10/521,662, filed Jul. 21, 2003.
Co-pending U.S. Appl. No. 10/754,415, filed Jan. 9, 2004.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed Oct. 12, 2004.
Co-pending U.S. Appl. No. 11/209,439, filed Aug. 23, 2005.
Co-pending U.S. Appl. No. 11/674,538, filed Feb. 13, 2007.
Co-pending U.S. Appl. No. 11/682,259, filed Mar. 5, 2007.
Co-pending U.S. Appl. No. 11/929,910, filed Oct. 30, 2007.
Co-pending U.S. Appl. No. 11/930,108, filed Oct. 31, 2007.
Co-pending U.S. Appl. No. 11/930,741, filed Oct. 31, 2007.
Co-pending U.S. Appl. No. 90/010,209, filed Jun. 27, 2008.
Co-pending U.S. Appl. No. 90/010,210, filed Jun. 27, 2008.
Co-pending U.S. Appl. No. 90/010,447, filed Apr. 9, 2009.
Co-pending U.S. Appl. No. 90/010,448, filed Apr. 9, 2009.
Co-pending U.S. Appl. No. 60/639,068, filed Dec. 22, 2004.
Co-pending U.S. Appl. No. 60/648,188, filed Jan. 28, 2005.
Co-pending U.S. Appl. No. 60/369,405, filed Apr. 1, 2002.
Co-pending U.S. Appl. No. 60/397,365, filed Jul. 19, 2002.
Co-pending U.S. Appl. No. 60/431,319.
Co-pending U.S. Appl. No. 60/443,443, filed Jan. 29, 2003.
Co-pending U.S. Appl. No. 60/443,788.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494.
Co-pending U.S. Appl. No. 60/470,175, filed May 12, 2003.
Co-pending U.S. Appl. No. 60/501,926, filed Sep. 11, 2003.
Co-pending U.S. Appl. No. 60/509,911.
Co-pending U.S. Appl. No. 60/604,329, filed Aug. 24, 2004.
Co-pending U.S. Appl. No. 60/615,387.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747,607, filed May 18, 2006.
Co-pending U.S. Appl. No. 60/771,101, filed Feb. 6, 2006.
Co-pending U.S. Appl. No. 60/773,124, filed Feb. 13, 2006.
Co-pending U.S. Appl. No. 60/891,479.
Co-pending U.S. Appl. No. 60/941,641.
Cornel A.J., et al., "Polymerase Chain Reaction Species Diagnostic Assay for Anopheles Quadrimaculatus Cryptic Species (Diptera:Culicidae) Based on Ribosomal DNA ITS2 Sequences," Journal of Medical Entomology, 1996, vol. 33 (1), pp. 109-116.
Courvalin P., "Vancomycin Resistance in Gram-Positive Cocci," Clinical Infectious Diseases, 2006, vol. 42 (Suppl 1), pp. S25-S34.
Couto I., et al., "Development of Methicillin Resistance in Clinical Isolates of *Staphylococcus scirui* by Transcriptional Activation of the mecA Homologue Native to the Species," Journal of Bacteriology, 2003, vol. 185 (2), pp. 645-653.
Crain P.F., et al., "Applications of Mass Spectrometry to the Characterization of Oligonucleotides and Nucleic Acids," Current Opinion in Biotechnology, 1998, vol. 9 (1), pp. 25-34.
Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance

(56) References Cited

OTHER PUBLICATIONS

Expressed by *Staphylococcus aureus* Mu50," Antimicrobial Agents and Chemotherapy, 2000, vol. 44 (9), pp. 2276-2285.

Dasen G., et al., "Classification and Identification of Propiolbacteria based on Ribosomal RNA Genes and PCR," Systematic and Applied Microbiology, 1998, vol. 21 (2), pp. 251-259.

De Jong J.C., et al., "Adenoviruses from Human Immunodeficiency Virus-Infected Individuals, Including Two Strains that Represent New Candidate Serotypes Ad50 and Ad51 of Species B1 and D, Respectively," Journal of Clincal Microbiology, 1999, vol. 37 (12), pp. 3940-3945.

De La Puente-Redondo V.A., et al., "Comparison of Different PCR Approaches for Typing of Francisella Tularensis Strains," Journal of Clinical Microbiology, 2000, vol. 38 (3), pp. 1016-1022.

Deforce D.L., et al., "Analysis of Oligonucleotides by ESI-MS," Advances in Chromatography, 2000, vol. 40, pp. 539-566.

Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.

Del Blanco Garcia N., et al., "Genotyping of Francisella Tularensis Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.

Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.

Demesure B., et al., "A Set of Universal Primers for Amplification of Polymorphic Non-Coding Regions of Mitochondrial and Chioroplast DNA in Plants," Molecular Ecology, 1995, vol. 4, pp. 129-131.

Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.

Depardieu F., et al., "VanD-Type Vancomycin-Resistant Enterococcus Faecium 10/96A," Antimicrobial Agents and Chemotherapy, 2003, vol. 47 (1), pp. 7-18.

Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.

Deurenberg R.R., et al., "The Prevalence of the *Staphylococcus aureus* tst Gene among Community- and Hospital-Acquired Strains and Isolates from Wegener's Granulomatosis Patients," FEMS Microbiology Letters, 2005, vol. 245 (1), pp. 185-189.

Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.

Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.

Dias Neto E., et al., "Shotgun Sequencing of the Human Transcriptome with ORF Expressed Sequence Tags," Proceedings of the National Academy of Sciences, 2000, vol. 97 (7), pp. 3491-3496.

Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.

Dinauer D.M., et al., "Sequence-Based Typing of HLA Class II DQB1," Tissue Antigens, 2000, vol. 55 (4), pp. 364-368.

Ding C., et al., "A High-Throughput Gene Expression Analysis Technique Using Compettiive PCR and Matrixassisted Laser Desorption Ionization Time-of-Flight MS," Proceedings of the National Academy of Sciences, 2003, vol. 100 (6), pp. 3059-3064.

DNA Modifying Enzymes and Cloning [online], [retrieved on Jan. 5, 2010]. Retrived from the Internet:< URL: http://www.neb.com/nebecomm/products/category12.asp#16.

Domingo M.C., et al., "High Prevalence of Glycopeptide Resistance Genes VanB, VanD, and VanG Not Associated with Enterococci in Human Fecal Flora," Antimicrobial Agents and Chemotherapy, 2005, vol. 49 (11), pp. 4784-4786.

Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.

Donofrio J.C., et al., "Detection of Influenza A and B in Respiratory Secretions with the Polymerase Chain Reaction," PCR Methods and Applications, 1992, vol. 1 (4), pp. 263-268.

Doty P., et al., "Strand Separation and Specific Recombination in Deoxyribonucleic Acids: Physical Chemical Studies," Proceedings of the National Academy of Sciences, 1960, vol. 46 (4), pp. 461-476.

Drosten C., et al., "Identification of a Novel Coronavirus in Patients with Severe Acute Respiratory Syndrome," New England Journal of Medicine, 2003, vol. 348 (20), pp. 1967-1976.

Dubernet S., et al., "A PCR-Based Method for Identification of Lactobacilli at to Genus Level," FEMS Microbiology Letters, 2002, vol. 214 (2), pp. 271-275.

Earl P.L., et al., "Homology Between DNA Polymerases of Poxviruses, Herpesviruses, and Adenoviruses: Nucleotide Sequence of the Vaccinia Virus DNA Polymerase Gene," Proceedings of the National Academy of Sciences, 1986, vol. 83 (11), pp. 3659-3663.

Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.

Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.

Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 38 (8), pp. 2982-2984.

Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.

Echavarria M., et al., "Prediction of Severe Disseminated Adenovirus Infection by Serum PCR," Lancet, 2001, vol. 358 (9279), pp. 384-385.

Echavarria M., et al., "Rapid Detection of Adenovirus in Throat Swab Specimens by PCR During Respiratory Disease Outbreaks among Military Recruits," Journal of Clinical Microbiology, 2003, vol. 41 (2), pp. 810-812.

Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.

Ecker D.J., et al., "Ibis T5000: A Universal Biosensor Approach for Microbiology," Nature Reviews Microbiology, 2008, vol. 6 (7), pp. 553-558.

Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.

Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.

Edwards K.M., et al., "Adenovirus Infections in Young Children," Pediatrics, 1985, vol. 76 (3), pp. 420-424.

Ellis J.S., et al., "Molecular Diagnosis of Influenza," Reviews in Medical Virology, 2002, vol. 12 (6), pp. 375-389.

Ellis J.S., et al., "Multiplex Reverse Transcription-PCR for Surveillance of Influenza A and B Viruses in England and Wales in 1995 and 1996," Journal of Clinical Microbiology, 1997, vol. 35(8), pp. 2076-2082.

(56) References Cited

OTHER PUBLICATIONS

Elnifro E.M., et al., "PCR and Restriction Endonuclease Analysis for Rapid Identification of Adenovirus Subgenera," Journal of Clinical Microbiology, 2000, vol. 38 (6), pp. 2055-2061.

Elsayed S., et al., "Development and Validation of a Molecular Beacon Probe-Based Real-Time Polymerase Chain Reaction Assay for Rapid Detection of Methicillin Resistance in *Staphylococcus aureus*," Archives of Pathology and Laboratory Medicine, 2003, vol. 127 (7), pp. 845-849.

EMBL "*Arabidopsis thaliana* T-DNA Flanking Sequence, Left Border, Clone 346C06," Accession No. AJ552897, Mar. 29, 2003.

EMBL "Dog (Clone: CXX.147) Primer for STS 147, 3" End, Sequence Tagged Site," Accession No. L15697, Mar. 4, 2000.

EMBL "Human, muscle, Mitochondrial Mutant, 22 nt, segment 2 of 2," Accession No. S90302, Sep. 1, 2004.

EMBL "Sequence 10 from Patent U.S. Pat. No. 6,563,025," Accession No. AR321656, Aug. 18, 2003.

EMBL "Synthetic Construct DNA, Reverse Primer for Human STS sts-AA031654 at 1p36" Accession No. AB068711, May 21, 2003.

Endonuclease IV [online], [retrieved on Jan. 5, 2010]. Retrived from the Internet:< URL: www.neb.com/nebecomm/products/productM0304.asp.

Enright M.C., et al., "A Multilocus Sequence Typing Scheme for *Streptococcus pneumoniae*: Identification of Clones Associated with Serious Invasive Disease," Microbiology, 1998, vol. 144 (Pt 11), pp. 3049-3060.

Enright M.C., et al., "Multilocus Sequence Typing for Characterization of Methicillin-Resistant and Methicillin-Susceptible Clones of *Staphylococcus aureus*," Journal of Clinical Microbiology, 2000, vol. 38 (3), pp. 1008-1015.

Enright M.C., et al., "Multilocus Sequence Typing of *Streptococcus pyogenes* and theRelationships between Emm Type and Clone," Infection and Immunity, 2001, vol. 69 (4), pp. 2416-2427.

Enright M.C., et al., "The Evolutionary History of Methicillin-Resistant *Staphylococcus aureus* (MRSA)," Proceedings of the National Academy of Sciences, 2002, vol. 99, (11), pp. 7687-7692.

Enright M.C., "The Evolution of a Resistant Pathogen—the Case of MRSA," Current Opinion in Pharmacology, 2003, vol. 3 (5), pp. 474-479.

Eremeeva M.E., et al., "Evaluation of a PCR Assay for Quantitation of Rickettsia rickettsii and Closely Related Spotted Fever Group Rickettsiae," Journal of Clinical Microbiology, 2003, vol. 41 (12), pp. 5466-5472.

Erlich H.A., Ed., PCR Technology: Principles and Applications for DNA Amplification, W.H. Freeman and Company, 1989.

Esmans E.L., et al., "Liquid Chromatography-Mass Spectrometry in Nucleoside, Nucleotide and Modified Nucleotide Characterization," Journal of Chromatography, 1998, vol. 794, pp. 109-127.

Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.

European Search Report for Application No. EP10175659.1, dated Feb. 9, 2011, 4 pages.

Evans P., et al., "Practical Algorithms for Universal DNA Primer Design: An Exercise in Algorithm Engineering," Currents in Computational Molecular Biology, 2001, pp. 25-26.

Ex Parte Re-Examination Certificate for U.S. Appl. No. 90/010,209 mailed Jul. 7, 2009.

Ex Parte Re-Examination Certificate for U.S. Appl. No. 90/010,210, mailed Dec. 28, 2010.

Ex Parte Re-Examination Certificate for U.S. Appl. No. 90/010,447 mailed Feb. 15, 2011.

Examiner Interview Summary dated Oct. 3, 2005 for U.S. Appl. No. 10/326,046, filed Dec. 18, 2002.

Examiner Interview Summary dated Nov. 6, 2008 for U.S. Appl. No. 10/728,486, filed Dec. 5, 2003.

Examiner Interview Summary dated Jun. 7, 2011 for U.S. Appl. No. 11/930,108, filed Oct. 31, 2007.

Examiner Interview Summary dated Aug. 10, 2004 for U.S. Appl. No. 09/798,007, filed Mar. 2, 2001.

Examiner Interview Summary dated Aug. 10, 2004 for U.S. Appl. No. 09/891,793, filed Jun. 26, 2001.

Examiner Interview Summary dated Aug. 10, 2004 for U.S. Appl. No. 10/156,608, filed May 24, 2002.

Examiner Interview Summary dated Aug. 10, 2004 for U.S. Appl. No. 10/326,642, filed Dec. 18, 2002.

Examiner Interview Summary dated May 19, 2003 for U.S. Appl. No. 09/891,793, filed Jun. 26, 2001.

Examiner Interview Summary dated Oct. 24, 2008 for U.S. Appl. No. 11/582,859, filed Oct. 17, 2006.

Examiner Interview Summary dated Feb. 27, 2006 for U.S. Appl. No. 10/326,644, filed Dec. 18, 2002.

Examiner Interview Summary dated Feb. 27, 2007 for U.S. Appl. No. 10/891,337, filed Jul. 14, 2004.

Examiner Interview Summary dated Jan. 27, 2006 for U.S. Appl. No. 10/323,211, filed Dec. 18, 2002.

Examiner Interview Summary dated May 28, 2008 for U.S. Appl. No. 10/660,998, filed Sep. 12, 2003.

Examiner Interview Summary dated Oct. 28, 2008 for U.S. Appl. No. 11/331,987, filed Jan. 13, 2006.

Examiner Interview Summary dated Oct. 29, 2008 for U.S. Appl. No. 11/331,978, filed Jan. 13, 2006.

Examiner Interview Summary dated Oct. 29, 2009 for U.S. Appl. No. 10/660,122, filed Sep. 11, 2003.

Examiner Interview Summary dated Jul. 31, 2006 for U.S. Appl. No. 10/326,643, filed Dec. 18, 2002.

Extended European Search Opinion for Application No. EP10175659.1, dated Feb. 21, 2011, 5 pages.

Extended European Search Report for Application No. EP10179789.2, dated Mar. 22, 2011, 9 pages.

Extended European Search Report for Application No. EP10179791.8, dated Mar. 17, 2011, 7 pages.

Extended European Search Report for Application No. EP10179795.9, dated Mar. 22, 2011, 9 pages.

Facklam R., et al., "Emm Typing and Validation of Provisional M Types for Group A Streptococci," Emerging Infectious Diseases, 1999, vol. 5 (2), pp. 247-253.

Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.

Farlow J., et al., "Francisella Tularensis Strain Typing Using Multiple-Locus, Variable-Number Tandem Repeat Analysis," Journal of Critical Microbiology, 2001, vol. 39 (9), pp. 3186-3192.

Farrell D.J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.

Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.

Fedele C.G., et al., "Quantitation of Polyomavirus DNA by a Competitive Nested Polymerase Chain Reaction," Journal of Virological Methods, 2000, vol. 88 (1), pp. 51-61.

Feng P., "Impact of Molecular Biology on the Detection of Food Pathogens," Molecular Biotechnology, 1997, vol. 7 (3), pp. 267-278.

Fenollar F., et al., "Molecular Genetic Methods for the Diagnosis of Fastidious Microorganisms," Acta Pathologica, Microbiologica, et Immunologica Scandinavica, 2004, vol. 112 (11-12), pp. 785-807.

Figueiredo L.M., et al., "Identification of Brazilian Flavivirus by a Simplified Reverse Transcription-Polymerase Chain Reaction Method Using Flavivirus Universal Primers," American Journal of Tropical Medicine and Hygiene, 1998, vol. 59 (3), pp. 357-362.

Final Office Action dated Dec. 3, 2009 for U.S. Appl. No. 11/582,859, filed Oct. 17, 2006.

Final Office Action dated Aug. 6, 2010 for U.S. Appl. No. 11/929,910, filed Oct. 30, 2007.

Final Office Action dated Jul. 8, 2010 for U.S. Appl. No. 12/326,800, filed Dec. 2, 2008.

(56) References Cited

OTHER PUBLICATIONS

Final Office Action dated May 12, 2010 for U.S. Appl. No. 11/674,538, filed Feb. 13, 2007.
Final Office Action dated Apr. 14, 2011 for U.S. Appl. No. 12/049,949, filed Mar. 17, 2008.
Final Office Action dated Jun. 14, 2011 for U.S. Appl. No. 12/616,422, filed Nov. 11, 2009.
Final Office Action dated Oct. 14, 2009 for U.S. Appl. No. 10/943,344, filed Sep. 17, 2004.
Final Office Action dated Nov. 17, 2009 for U.S. Appl. No. 11/582,875, filed Oct. 17, 2006.
Final Office Action dated Feb. 18, 2010 for U.S. Appl. No. 10/754,415, filed Jan. 9, 2004.
Final Office Action dated Nov. 20, 2009 for U.S. Appl. No. 11/331,987, filed Jan. 13, 2006.
Final Office Action dated Dec. 22, 2009 for U.S. Appl. No. 11/582,864, filed Oct. 17, 2006.
Final Office Action dated Jun. 23, 2010 for U.S. Appl. No. 11/930,017, filed Oct. 30, 2007.
Final Office Action dated Feb. 26, 2009 for U.S. Appl. No. 11/582,863, filed Oct. 17, 2006.
Final Office Action dated Jan. 30, 2009 for U.S. Appl. No. 10/844,938, filed May 12, 2004.
Flora J.W., et al, "Dual-Micro-ESI Source for Precise Mass Determination on a Quadrupole Time-of-Flight Mass Spectrometer for Genomic and Proteomic Applications," Analytical and Bioanalytical Chemistry, 2002, vol. 373 (7), pp. 538-546.
Fong W.K., et al., "Rapid Solid-Phase Immunoassay for Detection of Methicillin-Resistant *Staphylococcus aureus* Using Cycling Probe Technology," Journal of Clinical Microbiology, 2000, vol. 38 (7), pp. 2525-2529.
Fox A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.
Fox A., et al., "Report of the Bioterrorism Workshop," Journal of Microbiological Methods, 2002, vol. 51 (3), pp. 247-254.
Fox J.P., et al., "The Virus Watch Program: A Continuing Surveillance of Viral Infections in Metropolitan New York Families," American Journal of Epidemiology, 1969, vol. 89 (1), pp. 25-50.
Fox K.F., et al., "Identification of *Brucella* by Ribosomal-Spacer-Region PCR and Differentiation of Brucell Canis from Other *Brucella* spp. Pathogenic for Humans by Carbohydrate Profiles," Journal of Clinical Microbiology, 1998, vol. 36 (11), pp. 3217-3222.
Francois J.C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences, 1989, vol. 86 (24), pp. 9702-9706.
Francois P., et al., "Rapid Detection of Methicillin-Resistant *Staphylococcus aureus* Directly from Sterile or Nonsterile Clinical Samples by a New Molecular Assay," Journal of Clinical Microbiology, 2003, vol. 41 (1), pp. 254-260.
Fraser C.M., et al., "The Mimimal Gene Complement of Mycoplasma Genitalium," Science, 1995, vol. 270 (5235), pp. 397-403.
Freiberg C., et al., "Genome-Wide mRNA Profiling: Impact on Compound Evaluation and Target Identification in Anti-Bacterial Research," Targets, 2002, vol. 1 (1), pp. 20-29.
Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.
Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.
Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.
Fujimoto T., et al., "Single-Tube Multiplex. PCR for Rapid and Sensitive Diagnosis of Subgenus B and Other Subgenera Adenovirus in Clinical Samples," Microbiology and Immunology, 2000, vol. 44 (10), pp. 821-826.
Fujimura S., et al., "Characterization of the mupA Gene in Strains of Methicillin-Resistant *Staphylococcus aureus* with a Low Level of Resistance to Mupirocin," Antimicrobial Agents and Chemotherapy, 2001, vol. 45 (2), pp. 641-642.
Fujimura S., et al., "Isoleucyl-tRNA Synthetase Mutations in *Staphylococcus aureus* ClinicalIsolates and In Vitro Selection of Low-Level Mupirocin-Resistant Strains," Antimicrobial Agents and Chemotheraphy, 2003, vol. 47 (10), pp. 3373-3374.
Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.
Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.
Gall J.G., et al., "Construction and Characterization of Hexon-Chimeric Adenoviruses: Specification of Adenovirus Serotype," Journal of Virology, 1998, vol. 72 (12), pp. 10260-10264.
Gammelin M., et al., "Two Subtypes of Nucleoproteins (NP) of Influenza A Viruses," Virology, 1989, vol. 170 (1), pp. 71-80.
Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.
Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.
Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.
Gaydos C.A., et al., "Adenovirus Vaccines in the U.S. Military," Military Medicine, 1995, vol. 160 (6), pp. 300-304.
Geha D.J., et al., "Multiplex PCR for Identification of Methicillin-Resistant Staphylococci in the Clinical Laboratory," Journal of Clinical Microbiology, 1994, vol. 32 (7), pp. 1768-1772.
Genbank, "{Deletion 6} [Human, Muscle, Mitochondrial Mutant, 22 nt, Segment 2 of 2]," Accession No. S90302.1, Jun. 10, 1992.
Genbank, "Acinetobacter Genomosp. 10 Strain CIP 70.12 RNA Polymerase Subunit B (rpoB) Gene, Complete Cds," Accession No. 78099429, Mar. 11, 2006.
Genbank, "Bovine Parainfluenza Virus 3 Strain Shipping Fever, Complete Genome," Accesion No. AF178655, Sep. 19, 2000.
Genbank, "Clostridium Tetani E88, Complete Genome," Accession No. AE015927.1, Feb. 4, 2003.
Genbank, "*E. coli* Operon rpoBC Coding for the Beta- and Beta"-Subunits of RNA Polymerase (Genes rpoC and rpoB), and Genes rpIL, rlpJ, rplA, and rplK Coding for 50S Ribosomal Subunit Proteins L7/L12, L10, L1, and L11, Respectively. (Map position 89-90 min.)," Accession No. 42813, Feb. 28, 1992.
Genbank, "*E.coli* 16S Ribosomal RNA," Accession No. 174375, Aug. 11, 1995.
Genbank, "*E.coli* Open Reading Frame Upstream of Leu Operon," Accession No. M21150, Sep. 15, 1990.
Genbank, "*E.coli* rRNA Operon (rrnB) Coding for Glu-tRNA-2, 5S, 16S and 23S rRNA," Accession No. 147581, Sep. 14, 1992.
Genbank, "Enterococcus Malodoratus Strain ATCC43197 Elongation Factor Tu (tufA) Gene, Partial Cds," Accession No. AF274728, Dec. 11, 2000.
Genbank "*Escherichia coli* str. K-12 substr. MG1655, Complete Genome," Accession No. NC000913, Oct. 15, 2001.
Genbank, "*Homo sapiens* Haplotype V Mitochondrion, Complete Genome", Accession No. AF381990.1, Dec. 28, 2001.
Genbank, "Human Adenovirus Type 4 Hexon Gene," for Accession No. X84646, Jun. 30, 1995.

(56) References Cited

OTHER PUBLICATIONS

Genbank, "Human Coronavirus 229E, Complete Genome," Accession No. AF304460, Jul. 11, 2001.
Genbank, "Human isolate L34 Mitochondrion D-loop Region", Accession No. U08081.1, Aug. 16, 1994.
GenBank, "il11b08.y1 Human insulinoma Homo sapiens cDNA clone IMAGE:6029534 5-similar to SW:COX3_HUMAN P00414 Cytochrome C Oxidase Polypeptide III ;, mRNA sequence", Accession No. BQ581956.1, Jun. 20, 2002.
Genbank "Influenza A virus (A/swine/Tennessee/24/1977(H1N1)) Polymerase 2 (PB2) Gene, Complete Cds," Accession No. M73513.1, Jul. 28, 1992.
Genbank, "Influenza B Virus B/Panama/45/90 Polymerase (PB2) mRNA, Complete Cds", Accession No. AF005737, Oct. 4, 1997, pp. 1-3.
Genbank "Influenza B/Ann Arbor/1/66 (wild-type) PB2 Protein RNA, Complete cds," Accession No. M20168.1, Aug. 2, 1993.
Genbank, "Mastadenovirus h7 Hexon Gene," Accession No. Z48571, Apr. 18, 2005.
GenBank, "or72a01.s1 NCI_CGAP_Lu5 Homo sapiens cDNA Clone IMAGE:1601352 3-similar to SW:COX1_HUMAN P00395 Cytochrome C Oxidase Polypeptide I ;, mRNA sequence", Accession No. AI002209.1, Jun. 10, 1998.
Genbank "*Staphylococcus aureus* LukS-PV, LukF-PV Genes for Panton-Valentine Leukocidin S, Panton-Valentine Leukocidin F, Complete cds," Accession No. AB186917, Feb. 8, 2005.
Genbank "*Staphylococcus aureus* RN4220 ErmC Gene, Partial Cds," Accession No. 18542231, Sep. 16, 2003.
Genbank "*Staphylococcus aureus* Strain MSSA476, Complete Genome," Accession No. BX571857.1, Jun. 24, 2004.
Genbank, "*Staphylococcus aureus* subsp. *aureus* Mu50, Complete Genome," Accession No. 15922990, Oct. 4, 2001.
Genbank "*Staphylococcus aureus* subsp, *aureus* MW2, Complete Genome," Accession No. GI21281729, May 31, 2002.
Genbank, "*Staphylococcus epidermidis* ATCC 12228, Complete Genome," Accession No. AE015929.1, Jan. 2, 2003.
Genbank "*Streptococcus agalactiae* 2603V/R, Complete Genome," Accession No. AE009948.1, Aug. 28, 2002.
Genbank, "*Streptococcus anginosus* Elongation Factor Tu (tuf) Gene, Partial cds," Accession No. AF276257.1, Jul. 1, 2001.
Genbank, "*Streptococcus pneumoniae* Isolate 95.1In00S DNA Gyrase Subunit B (gyrB) Gene, Complete Cds," Accession No. 73916349, Sep. 30, 2005.
Genbank "*Streptococcus pneumoniae* R6, Complete Genome," Accession No. NC003098, Jul. 19, 2008.
Genbank, "*Streptococcus pyogenes* Strain MGAS8232, Complete Genome," Accession No. AE009949.1, Apr. 3, 2002.
Genbank, "Venezuelan Equine Encephalitis Virus Nonstructural Polyprotein and Structural Polyprotein Genes, Complete Cds," Accession No. AF375051.1, Jun. 26, 2001.
Gendel S.M., "Computational Analysis of the Specificity of 16S rRNA-Derived Signature Sequencesfor Identifying Food-Related Microbes," Food Microbiology, 1996, vol. 13, pp. 1-15.
Gibb T.R., et al., "Development and Evaluation of a 5″ Fluorogenic Nuclease Assay to Detect and Differentiate Between Ebola Virus Subtypes Zaire and Sudan," Journal of Clinical Microbiology, 2001, vol. 39 (11), pp. 4125-4130.
Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.
Giles R.E., et al., "Maternal Inheritance of Human Mitochondrial DNA," Proceedings of the National Academy of Sciences, 1980, vol. 77 (11), pp. 6715-6719.
Gill S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain," Journal of Bacteriology, 2005, vol. 187 (7), pp. 2426-2438.

Gilliland G., et al., "Analysis of Cytokine mRNA and DNA: Detection and Quantitation by Competitive Polymerase Chain Reaction," Proceedings of the National Academy of Sciences, 1990, vol. 87 (7), pp. 2725-2729.
Ginther C., et al., "Identifying Individuals by Sequencing Mitochondrial DNA from Teeth," Nature Genetics, 1992, vol. 2 (2), pp. 135-138.
Gjoen K.V., et al., "Specific Detection of Coxsackie Viruses A by the Polymerase Chain Reaction," Clinical and Diagnostic Virology, 1997, vol. 8 (3), pp. 183-188.
Golden M.R., et al., "Pilot Study of COBAS PCR and Ligase Chain Reaction for Detection of Rectal Infections Due to Chlamydia Trachomatis," Journal of Clinical Microbiology, 2003, vol. 41 (5), pp. 2174-2175.
Gorman O.T., et al., "Evolution of Influenza A Virus PB2 Genes: Implications for Evolution of the Ribonucleoprotein Complex and Origin of Human Influenza A Virus," Journal of Virology, 1990, vol. 64 (10), pp. 4893-4902.
Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.
Gravet A., et al., "Characterization of a Novel Structural Member, LukE-LukD, of the Bi-Component *Staphylococcal leucotoxins* Family," FEBS Letters, 1998, vol. 436 (2), pp. 202-208.
Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.
Greenberg B.D., et al., "Intraspecific Nucleotide Sequence Variability Surrounding the Origin of Replicationin Human Mitochondrial DNA," Gene, 1983, vol. 21, pp. 33-49.
Griffey, et al., "Detection of Base Pair Mismatches in Duplex DNA and RNA Oligonucleotides Using Electrospray Mass Spectrometry," SPIE, 1997, vol. 2985, pp. 82-86.
Griffin T.J., et al., "Direct Genetic Analysis by Matrix-Assisted Laseer Desorption/Ionization Mass Spectrometry," Proceedings of the National Academy of Sciences, 1999, vol. 96 (11), pp. 6301-6306.
Griffin T.J., et al., "Single-Nucleotide Polymorphism Analysis by Maldi-TOF Mass Spectrometry," Trends in Biotechnology, 2000, vol. 18 (2), pp. 77-84.
Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.
Grundmann H., et al., "Emergence and Resurgence of Meticillin-Resistant *Staphylococcus aureus* as a Public-Health Threat," Lancet, 2006, vol. 368 (9538), pp. 874-885.
Grzybowski T., et al., "Extremely High Levels of Human Mitochondrial DNA Heteroplasmy in Single Hair Roots," Electrophoresis, 2000, vol. 21 (3), pp. 548-553.
Gu Z., et al., "Multiplexed, Real-Time PCR for Quantitative Detection of Human Adenovirus," Journal of Clinical Microbiology, 2003, vol. 41 (10), pp. 4636-4641.
Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.
Haff L.A., et al., "Multiplex Genotyping of PCR Products with Mass Tag-Labeled Primers," Nucleic Acids Research, 1997, vol. 25 (18), pp. 3749-3750.
Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.
Haines J.D., et al., "Medical Response to Bioterrorism: Are We Prepared," Journal of Oklahoma State Medical Association, 2000, vol. 93, pp. 187-196.
Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.
Hamdad F., et al., "Detection of Methicillin/Oxacillin Resistance and Typing in Aminoglycoside-Susceptible Methicillin-Resistant

(56) References Cited

OTHER PUBLICATIONS and Kanamycin-Tobramycin-Resistant Methicillin-Susceptible," Microbial Drug Resistance, 2006, vol. 12 (3), pp. 177-185.
Hamel S., et al., "Consensus PCR and Microarray for Diagnosis of the Genus *Staphylococcus*, Species, and Methicillin Resistance," Biotechniques, 2001, vol. 31 (6), pp. 1364-1372.
Hammerle T., et al., "A Sensitive PCR Assay System for the Quantitation of Viral Genome Equivalents:Hepatitis C Virus (HCV)," Archives of Virology, 1996, vol. 141 (11), pp. 2103-2114.
Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10) pp. 954-962.
Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.
Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.
Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.
Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.
Hanssen A.M., et al., "Sccmecin Staphylococci: Genes on the Move," FEMS Immuol Medical Microbiol, 2006, vol. 46, pp. 8-20.
Harris K.A., et al., "Duplex Real-Time PCR Assay for Detection of *Streptococcus pneumoniae* in Clinical Samples and Determination of Penicillin Susceptibility," Journal of Clinical Microbiology, 2008, vol. 46 (8), pp. 2751-2758.
Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.
Hassan A.A., et al., "Inter- and Intraspecies Variations of the 16S-23S rDNA Intergenic Spacer Region of Various Streptococcal Species," Systematic and Applied Microbiology, 2003, vol. 26 (1), pp. 97-103.
Haugland R.A., et al., "Identification of Putative Sequence Specific PCR Primers for Detection of the Toxygenic Fungal Species Stachybotrys Chartarum," Molecular and Cellular Probes, 1998, vol. 12 (6), pp. 387-396.
Hayashi H., et al., "Phylogenetic Analysis of the Human Gut Microbiota Using 16S rDNA Clone Libraries and Strictly Anaerobic Culture-based Methods," Journal of Microbiology, Immunology, 2002, vol. 46 (8), pp. 535-548.
He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.
Heim A., et al., "Rapid and Quantitative Detection of Human Adenovirus DNA by Real-Time PCR," Journal of Medical Virology, 2003, vol. 70, pp. 228-239.
Henchal E.A., et al., "Sensitivity and Specificity of a Universal Primer Set for the Rapid Diagnosis of Dengue Virus Infections by Polymerase Chain Reaction and Nucleic Acid Hybridization," American Journal of Tropical Medicine and Hygiene, 1991, vol. 45 (4), pp. 418-428.
Herrmann B., et al., "Differentiation of *Chiamydia* spp. by Sequence Determination and Restriction Endonuclease Cleavage of RNase P RNA Genes," Journal of Clinical Microbiology, 1996, vol. 34 (8), pp. 1897-1902.

Higgins G.S., et al., "Competitive Oligonucleotide Single-base Extension Combined with Mass Spectrometric Detection for Mutation Screening," Biotechniques, 1997, vol. 23 (4), pp. 710-714.
Higgins J.A., et al., "Sensitive and Rapid Identification of Biological Threat Agents," Annals of the New York Academy of Sciences, 1999, vol. 894, pp. 130-148.
Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.
Hiramatsu K., et al., "The Emergence and Evolution of Methicillin-Resistant *Staphylococcus aureus*," Trends Microbiology, 2001, vol. 9 (10), pp. 486-493.
Hobbs L.J., et al., "Either Bacteriophage T4 RNase H or *Escherichia coli* DNA Polymerase I Is Essential for Phage Replication," Journal of Bacteriology, 1996, vol. 178 (23), pp. 6772-6777.
Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.
Hoffman E., et al., "Rescue of Influenza B Virus from Eight Plasmids," Proceedings of the National Academy of Sciences, 2002, vol. 99 (17), pp. 11411-11416.
Hoffmann E., et al., "Universal Primer Set for the Full-Length Amplification of all Influenza A Viruses," Archives of Virology, 2001, vol. 146 (12), pp. 2275-2289.
Hofstadler S.A., et al., "TIGER: The Universal Biosensor," International Journal of Mass Spectrometry, 2005, vol. 242, pp. 23-41.
Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.
Holland M.M., et al., "Mitochondrial DNA Sequence Analsysis—Validation and Use for Forensic Casework," Forensic Science Review, 1999, vol. 11 (1), pp. 22-50.
Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.
Holm L., et al., "Removing Near-Neighbour Redundancy from Large Protein Sequence Collections," Bioinformatics, 1998, vol. 14 (5), pp. 423-429.
Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.
Honda K., et al., "Universal Method of Hypersensitive Nested PCR Toward Forensic DNA typing," International Congress Series, 1998, vol. 7, pp. 28-30.
Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.
Hood E., et al., "Chemical and Biological Weapons: New Questions, New Answers," Environmental Health Perspectives, 1999, vol. 107 (12), pp. 931-932.
Houng H.S., et al., "Rapid Type-Specific Diagnosis of Adenovirus Type 4 Infection Using a Hexon-Based Quantitative Fluorogenic PCR," Diagnostic Microbiology and Infectious Disease, 2002, vol. 42 (4), pp. 227-236.
Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.
Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.
Huletsky A., et al., "New Real-Time Pcr Assay for Rapid Detection of Methicillin-Resistantstaphylococcus Aureus Directly from Specimens Containing a Mixture of Staphylococci," Journal of Clinical Microbiology, 2004, vol. 42 (5), pp. 1875-1884.

(56) References Cited

OTHER PUBLICATIONS

Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.
Hung E.C., et al., "Detection of SARS Coronavirus RNA in the Cerebrospinal Fluid of a Patient with Severe Acute Respiratory Syndrome," Clinical Chemistry, 2003, vol. 49 (12), pp. 2108-2109.
Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.
Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.
Hurst G.B., et al., "MALDI-TOF Analysis of Polymerase Chain Reaction Products from Methanotrophic Bacteria," Analytical Chemistry, 1998, vol. 70 (13), pp. 2693-2698.
Hutchison C.A., et al., "Maternal Inheritance of Mammalian Mitochondrial DNA," Nature, 1974, vol. 251 (5475), pp. 536-538.
Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.
Ieven M., et al., "Rapid Detection of Methicillin Resistance in Coagulase-Negative Staphylococci by Commercially Available Fluorescence Test," Journal of Clinical Microbiology, 1995, vol. 33 (8), pp. 2183-2185.
Ihle O., et al., "Efficient Purification of DNA Fragments using a Protein Binding Membrane," Nucleic Acids Research, 2000, vol. 28 (16), pp. e76.
Inglis T.J., et al., "Rapid Genotypic Confirmation of Methicillin Resistance," Pathology, 1996, vol. 28 (3), pp. 259-261.
Ingman M., et al., "Mitochondrial Genome Variation and the Origin of Modern Humans," Nature, 2000, vol. 408 (6813), pp. 708-713.
International Preliminary Examination Report for Application No. PCT/US2002/06763, dated Jun. 11, 2003, 6 pages.
International Preliminary Examination Report for Application No. PCT/US2002/20336, dated Apr. 26, 2004, 8 pages.
International Preliminary Examination Report for Application No. PCT/US2003/09802, dated Apr. 8, 2005, 7 pages.
International Preliminary Examination Report for Application No. PCT/US2003/22835, dated Mar. 5, 2005, 4 pages.
International Preliminary Examination Report for Application No. PCT/US2003/38505, dated Mar. 3, 2006, 5 pages.
International Preliminary Examination Report for Application No. PCT/US2003/38757, dated Feb. 2, 2007, 5 pages.
International Preliminary Examination Report for Application No. PCT/US2003/38761, dated Jun. 27, 2006, 6 pages.
International Preliminary Report on Patentability and Written Opinion for Application No. PCT/US04/007236, dated Mar. 16, 2006, 7 pages.
International Preliminary Report on Patentability and Written Opinion for Application No. PCT/US2005/00386, dated Jul. 10, 2006, 6 pages.
International Preliminary Report on Patentability and Written Opinion for Application No. PCT/US2005/024799, dated Jan. 30, 2007, 7 pages.
International Preliminary Report on Patentability and Written Opinion for Application No. PCT/US2005/030058, dated Sep. 25, 2007, 6 pages.
International Preliminary Report on Patentability and Written Opinion for Application No. PCT/US2005/033707, dated Mar. 20, 2007, 6 pages.
International Preliminary Report on Patentability for Application No. PCT/US2004/033742, dated Jun. 20, 2006, 1 page.
International Preliminary Report on Patentability for Application No. PCT/US2005/018031, dated Nov. 29, 2006, 1 page.
International Preliminary Report on Patentability for Application No. PCT/US2006/028397, dated Jan. 22, 2008, 1 page.
International Preliminary Report on Patentability for Application No. PCT/US2008/054926, dated Aug. 26, 2009, 1 page.
International Preliminary Report on Patentability, Written Opinion and International Search Report for Application No. PCT/US2004/015123, dated Oct. 3, 2005, 8 pages.
International Search Report and Written Opinion for Application No. PCT/US2005/018031, dated Jun. 28, 2006, 14 pages.
International Search Report and Written Opinion for Application No. PCT/US2006/007747, dated Sep. 5, 2006, 13 pages.
International Search Report and Written Opinion for Application No. PCT/US2006/028397, dated Mar. 5, 2007, 14 pages.
International Search Report and Written Opinion for Application No. PCT/US2006/040747, dated Mar. 17, 2009, 19 pages.
International Search Report and Written Opinion for Application No. PCT/US2006/061307, dated Jan. 9, 2008, 21 pages.
International Search Report and Written Opinion for Application No. PCT/US2007/020045 dated Jan. 8, 2009, 17 pages.
International Search Report and Written Opinion for Application No. PCT/US2008/054926, dated Jan. 26, 2009, 15 pages.
International Search Report and Written Opinion for Application No. PCT/US2008/057901, dated Aug. 28, 2008, 14 pages.
International Search Report and Written Opinion for Application No. PCT/US2008/064891, dated Jun. 29, 2009, 15 pages.
International Search Report and Written Opinion for Application No. PCT/US2009/045496, dated Jan. 13, 2010, 19 pages.
International Search Report and Written Opinion for Application No. PCT/US2009/045660, dated Jan. 13, 2010, 22 pages.
International Search Report and Written Opinion for Application No. PCT/US2009/045800, dated Jan. 13, 2010, 22 pages.
International Search Report and Written Opinion for Application No. PCT/US2009/058759, dated Feb. 5, 2010, 25 pages.
International Search Report and Written Opinion for Application No. PCT/US2009/058943, dated Jan. 25, 2010, 16 pages.
International Search Report and Written Opinion for Application No. PCT/US2009/058960, dated Jan. 11, 2010, 21 pages.
International Search Report and Written Opinion for Application No. PCT/US2009/059082, dated Jan. 7, 2010, 18 pages.
International Search Report for Application No. PCT/US04/007236, dated Feb. 24, 2006, 2 pages.
International Search Report for Application No. PCT/US2002/06763, dated Oct. 23, 2002, 2 pages.
International Search Report for Application No. PCT/US2002/20336, dated Feb. 3, 2003, 4 pages.
International Search Report for Application No. PCT/US2003/009802, dated Aug. 3, 2004, 2 pages.
International Search Report for Application No. PCT/US2003/038505, dated Apr. 12, 2005, 2 pages.
International Search Report for Application No. PCT/US2003/038830, dated Aug. 25, 2004, 4 pages.
International Search Report for Application No. PCT/US2003/22835, dated Dec. 12, 2003, 1 page.
International Search Report for Application No. PCT/US2003/38757, dated Jun. 24, 2004, 2 pages.
International Search Report for Application No. PCT/US2003/38761, dated Dec. 30, 2005, 5 pages.
International Search Report for Application No. PCT/US2003/38795, dated Apr. 19, 2004, 3 pages.
International Search Report for Application No. PCT/US2004/012671, dated Sep. 28, 2007, 2 pages.
International Search Report for Application No. PCT/US2004/015123, dated Oct. 3, 2005, 2 pages.
International Search Report for Application No. PCT/US2004/015196, dated Jul. 1, 2005, 3 pages.
International Search Report for Application No. PCT/US2004/028869, dated Jul. 17, 2006, 4 pages.
International Search Report for Application No. PCT/US2004/033742, dated May 15, 2006, 2 pages.
International Search Report for Application No. PCT/US2005/000386, dated May 9, 2006, 3 pages.
International Search Report for Application No. PCT/US2005/005356, dated Aug. 7, 2007, 4 pages.

(56) References Cited

OTHER PUBLICATIONS

International Search Report for Application No. PCT/US2005/006133, dated Jul. 26, 2007, 4 pages.
International Search Report for Application No. PCT/US2005/009557, dated Sep. 19, 2005, 1 page.
International Search Report for Application No. PCT/US2005/018337, dated Oct. 10, 2006, 2 pages.
International Search Report for Application No. PCT/US2005/024799, dated Dec. 28, 2006, 4 pages.
International Search Report for Application No. PCT/US2005/030058, dated Aug. 20, 2007, 1 page.
International Search Report for Application No. PCT/US2005/033707, dated Feb. 6, 2006, 3 pages.
International Search Report for Application No. PCT/US2007/066194, dated Jan. 15, 2008, 4 pages.
International Search Report for Application No. PCT/US2008/065332, dated Nov. 28, 2008, 4 pages.
International Search Report for Application No. PCT/US2009/045635, dated Oct. 7, 2009, 9 pages.
Invitation to Pay Additional Fees and Partial International Search Report for Application No. PCT/US2009/045496, dated Nov. 23, 2009, 4 pages.
Invitation to Pay Additional Fees and Partial International Search Report for Application No. PCT/US2009/045637, dated Dec. 16, 2009, 10 pages.
Invitation to Pay Additional Fees and Partial International Search Report for Application No. PCT/US2009/058931, dated Jan. 14, 2010, 9 pages.
Invitation to Pay Additional Fees and Partial International Search Report for Application No. PCT/US2009/059055, dated Jan. 14, 2010, 10 pages.
Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N.R., et al., "MALDI-TOF Mass Spectrometric Method for Detection of Hybridized DNA Oligomers," Analytical Chemistry, 2001, vol. 73 (9), pp. 2126-2131.
Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.
Ito T., et al., "Insights on Antibiotic Resistance of *Staphylococcus aureus* from its Whole Genome: Genomic Island Scc," Drug Resistance Updates, 2003, vol. 6 (1), pp. 41-52.
Ito T., et al., "Structural Comparison of Three Types of Staphylococcal Cassette Chromosome mecIntegrated in the Chromosome in Methicillin-Resistant *Staphylococcus aureus*," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an Amblyomma Americanum Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33-37.
Jaulhac B., et al., "Specific Detection of the Toxic Shock Syndrome Toxin-1 Gene Using the Polymerase Chain Reaction," Molecular and Cellular Probes, 1991, vol. 5, pp. 281-284.

Jaulhac B., et al., "Synthetic DNA Probes for Detection of Genes for Enterotoxins A, B, C, D, E and for Tsst-1 in Staphylococcal Strains," Journal of Applied Bacterial, 1992, vol. 72 (5), pp. 386-392.
Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.
Jeong J., et al., "Early Screening of Oxacillin-Resistant *Staphylococcus aureus* and *Staphylococcus epidermidis* from Blood Culture," Journal of Korean Medical Science, 2002, vol. 17, pp. 168-172.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson A., et al., "Evaluation of PCR-based Methods for Discrimination of *Francisella* species and Subspecies and Development of Specific PCR that Distinguishes the Two Major Subspecies of *Francisella tularensis*," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.
Johnson Y.A., et al., "Precise Molecular Weight Determination of PCR Products of the rRNA Intergenic Spacer Region Using Electrospray Quadrupole Mass Spectrometry for Differentiation of B. Subtilis and B. Atrophaeus, Closely Related Species of Bacilli," Journal of Microbiological Methods, 2000, vol. 40 (3), pp. 241-254.
Jonas D., at al., "Rapid PCR-Based Identification of Methicillin-Resistant *Staphylococcus aureus* from Screening Swabs," Journal of Clinical Microbiology, 2002, vol. 40 (5), pp. 1821-1823.
Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.
Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.
Jurinke C., et al., "MALDI-TOF Mass Spectrometry. A Versatile Tool for High-Performance DNA Analysis," Molecular Biotechnology, 2004, vol. 26 (2), pp. 147-163.
Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.
Kageyama A., et al.,, "Rapid Detection of Human Fecal Eubacterium Species and Related Genera by Tested PCR Method," Journal of Microbiology, Immunology, 2001, vol. 45 (4), pp. 315-318.
Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.
Kaltenboeck B., et al., "Two-Step Polymerase Chain Reactions and Restriction Endonuclease Analyses Detect and Differentiate OmpA DNA of *Chlamydia* Spp.," Journal of Clinical Microbiology, 1992, vol. 30 (5), pp. 1098-1104.
Kasai H., et al., "Construction of the gyrB Database for the Identification and Classification of Bacteria," Genome Informatics. Workshop on Genome Informatics, 1998, pp. 13-21.
Katano H., et al., "Identification of Adeno-Associated Virus Contamination in Cell and Virus Stocks by PCR," Biotechniques, 2004, vol. 36 (4), pp. 676-680.
Katayama Y., et al., "Genetic Organization of the Chromosome Region Surrounding mecA inClinical Staphylococcal Strains: Role of IS431-Mediated mec1 Deletion in Expression of Resistance

(56) References Cited

OTHER PUBLICATIONS inmed-Canying, Low-Level Methicillin-Resistant *Staphylococcus haemolyticus*," Antimicrobial Agents and Chemotherapy, 2001, vol. 45 (7), pp. 1955-1963.

Ke D., et al., "Development of a PCR Assay for Rapid Detection of Enterococci," Journal of Clinical Microbiology, 1999, vol. 37 (11), pp. 3497-3503.

Kearns A.M., et al., "Rapid Detection of Methicillin-Resistant *Staphylococci* by Multiplex PCR," The Journal of Hospital Inspection, 1999, vol. 43 (1), pp. 33-37.

Keller A., et al., "Empirical Statistical Model to Estimate the Accuracy of Peptide Identifications Made by MS/MS and Database Search," Analytical Chemistry, 2002, vol. 74 (20), pp. 5383-5392.

Keys C., et al., "Highly Diverse Variable Number Tandem Repeat Loci in the *E. coli* O157:H7 and O55:H7 Genomes for High-Resolution Molecular Typing," Journal of Applied Microbiology, 2005, vol. 98 (4), pp. 928-940.

Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.

Khan S.A., et al., "Simultaneous Detection of Erythromycin-Resistant Methylase Genes ermA and ermC from *Staphylococcus* Spp. By Multiplex-PCR," Molecular and Cellular Probes, 1999, vol. 13 (5), pp. 381-387.

Kidd A.H., et al., "Rapid Subgenus Identification of Human Adenovirus Isolates by a General PCR," Journal of Clinical Microbiology, 1996, vol. 34 (3), pp. 622-627.

Kidd-Ljunggren K., et al., "The Hepatitis B Virus X Gene: Analysis of Functional Domain Variation and Gene Phylogeny using Multiple Sequences," Journal of General Virology, 1995, vol. 76 (pt 9), pp. 2119-2130.

Kikuchi K., et al., "Restriction Fragment Length Polymorphism Analysis of Clinical Isolates of *Mycobacterium haemophilum*," Journal of Clinical Microbiology, 1994, vol. 32 (7), pp. 1763-1767.

Kilbourne E.D., "Influenza Pandemics of the 20th Century," Emerging Infectious Diseases Journal, 2006, vol. 12 (1), pp. 9-14.

Kilbourne E.D., "Influenza Pandemics: Can We Prepare for the Unpredictable," Viral Immunology, 2004, vol. 17 (3), pp. 350-357.

Kilpatrick D.R., et al., "Group-Specific Identification of Polioviruses by PCR Using Primer Containing Mixed-Base or Deoxyinosine Residues at Positions of Codon Degeneracy," Journal of Clinical Microbiology, 1996, vol. 34 (12), pp. 2990-2996.

Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.

Kitagawa Y., et al., "Rapid Diagnosis of Methicillin-Resistant *Staphylococcus aureus* Bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive Staphylococci," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as anAugmented Surveillance Strategy for Influenza Virus and Adenovirus Identification," Journal of Clinical Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.

Kramer L.D., et al., "Dection of Encephalitis Viruses in Mosquitoes (Diptera: Culicidea) and Avian Tissues," Journal of Medical Entomology, 2002, vol. 39 (2), pp. 312-323.

Kramer L.D., et al., "Dection of St. Louis Encephalitis and Western Equine Encephalomyelitis RNAin Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of *Staphylococccus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in *Staphylococcus aureus*isolates Using Conventional and Molecular Methods: A Descriptive Study from a Burns Unit with Highprevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiazek T.G., et al., "A Novel Coronavirus Associated with Severe Acute Respiratory Syndrome," The New England Journal of Medicine, 2003, vol. 348 (20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M., et al., "Whole Genome Sequencing of Meticillin-Resistant *Staphylococcus aureus*," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "*Staphylococcus aureus* Panton Valentine Leukocidin CausesNecrotizing Pneumonia," ScienceExpress, 2007, 8 pages.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine EncephalitisViruses by Nucleic Acid Amplification Assays," Journal of Clinical Microbiology, 2003, vol. 41 (1), pp. 379-385.

Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.

(56) References Cited

OTHER PUBLICATIONS

Lau L.T., et al., "Nucleic Acid Sequence-Based Amplification Methods to Detect Avian Influenza Virus," Biochemical and Biophysical Research Communications, 2004, vol. 313 (2), pp. 336-342.
Le Cann P., et al., "Quantification of Human Astroviruses in Sewage Using Real-Time RT-PCR," Research in Microbiology, 2004, vol. 155 (1), pp. 11-15.
Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.
Lednicky J.A., et al., "Polyomaviruses and Human Tumors: A Brief Review of Current Concenpts and Interpretations," Frontiers Bioscience, 1999, vol. 4, pp. D153-D164.
Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.
Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.
Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.
Lemee L., et al., "Multiplex PCR Targeting Tpi (Triose Phosphate Isomerase), tcdA (Toxin A), and tcdB (Toxin B) Genes for Toxigenic Culture of Clostridium Difficile," Journal of Clinical Microbiology, 2004, vol. 42 (12), pp. 5710-5714.
Lengyel A., et al., "Characterization of the Main Protein Components of Adenovirus Virion and itsPossible Use in Laboratory Diagnostics," Acta Microbiologica Immunologica Hungarica, 1998, vol. 43 (3-4), pp. 281-283.
Leroy E.M., et al., "Diagnosis of Ebola Haemorrhagic Fever by RT-PCR in an Epidemic Setting," Journal of Medicinal Virology, 2000, vol. 60 (4), pp. 463-467.
Levi K., et al., "Evaluation of an Isothermal Signal Amplification Method for Rapid Detection of Methicillin-Resistant *Staphylococcus aureus* from Patient-Screening Swabs," Journal of Clinical Microbiology, 2003, vol. 41 (7), pp. 3187-3191.
Levine S.M., et al., "PCR-Based Detection of Bacillus Anthracis in Formalin-Fixed Tissue from a Patient Receiving Ciprofloxacin," Journal of Clinical Microbiology, 2002, vol. 40 (11), pp. 4360-4362.
Levison P.R., et al., "Recent Developments of Magnetic Beads for Use in Nucleic Acid Purification," Journal of Chromatography, 1998, vol. A816, pp. 107-111.
Lewers K.S., et al., "Detection of Linked QTL for Soybean Brown Stern Rot Resistance in "BSR 101" as Expressed in a Growth Chamber Environment," Molecular Breeding, 1999, vol. 5, pp. 33-42.
Li C., et al., "Evolution of H9N2 Influenza Viruses from Domestic Poultry in Mainland China," Virology, 2005, vol. 340 (1), pp. 70-83.
Li J., et al., "Single Nucleotide Polymorphism Determination Using Primer Extension and Time-of-Flight Mass Spectrometry," Electrophoresis, 1999, vol. 20 (6), pp. 1258-1265.
Li Q., et al., "Genetic Variability of Hexon Loops 1 and 2 between Seven Genome Types of Adenovirus Serotype 7," Archives of Virology, 1999, vol. 144 (9), pp. 1739-1749.
Li Q., et al., "Screening of the High Yield Influenza B Virus on MDCK c14d Cloning of its Whole Genome," International Congress Series, 2004, vol. 1263, pp. 610-614.
Li Q.G., et al., "Analysis of 15 Different Genome Types of Adenovirus Type 7 Isolated on FiveContinents," Journal of Virology, 1986, vol. 60 (1), pp. 331-335.
Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.

Liebermann H., et al., "Mapping of Epitopes on the Fiber Knobs of Human Adenovirus Serotypes 8 and 15," Intervirology, 2002, vol. 45 (1), pp. 59-66.
Liebermann H., et al., "Mapping of Linear Epitopes on Fibre Knob of Human Adenovirus Serotype 5," Virus Research, 2001, vol. 73 (2), pp. 145-151.
Lim L.P., et al., "The MicroRNAs of Caenorhabditis Elegans," Genes and Development, 2003, vol. 17 (8), pp. 991-1008.
Limbach P.A., et al., "Enzymatic Sequencing of Oligonucleotides with Electrospray Mass Spectrometry," 42nd ASMS Conference on Mass Spectrometry, 1994.
Limoncu M.H., et al., "Emergence of Phenotypic Resistance to Ciprofloxacin and Levofloxacin Inmethicillin-Resistant and Methicillin-Sensitive *Staphylococcus aureus* Strains," International Journal of Antimicrobial Agents, 2003, vol. 21 (5), pp. 420-424.
Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.
Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.
Lina G., et al., "Bacterial Competition for Human Nasal Cavity Colonization: Role of Staphylococcalagr Alleles," Applied and Environmental Microbiology, 2003, vol. 69 (1), pp. 18-23.
Lina G., et al., "Involvement of Panton-Valentine Leukocidin-Producing *Staphylococcus aureus* in Primary Skin Infections and Pneumonia," Clinical Infectious Diseases, 1999, vol. 29 (5), pp. 1128-1132.
Linssen B., et al., "Development of Reverse Transcription—PCR Assays Specific for Detection of Equine Encephalitis Viruses," Journal of Clinical Microbiology, 2000, vol. 38 (4), pp. 1527-1535.
Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.
Little D.P., et al, "Rapid Sequencing of Oligonucleotides by High-Resolution Mass Spectrometry," Journal of the American Chemical Society, 1994, vol. 116 (11), pp. 4893-4897.
Liu C., et al., "Improving the Microdialysis Procedure for Electrospray Ionization Mass Spectrometry of Biological Samples," Journal of Mass Spectrometry, 1997, vol. 32 (4), pp. 425-431.
Liu J.H., et al., "Interregional Transmission of the Internal Protein Genes of H2 Influenza Virus in Migratory Ducks from North America to Eurasia," Virus Genes, 2004, vol. 29 (1), pp. 81-86.
Liu Y., et al., "An Unusual Gene Arrangement for the Putative Chromosome Replication Origin and Circadianexpression of dnaN in *Synechococcus* sp. Strain PCC 7942," Gene, 1996, vol. 172 (1), pp. 105-109.
Livermore D.M., "The Threat from the Pink Corner," Annals of Medicine, 2003, vol. 35 (4), pp. 226-234.
Loakes D., et al., "Nitroindoles as Universal Bases," Nucleosides and Nucleotides, 1995, vol. 14 (3-5), pp. 1001-1003.
Loo J.A., et al., "Applying Charge Discrimination with Electrospray Ionization-Mass Spectrometry to Protein Analysis," Journal of American Society for Mass Spectrometry, 1995, vol. 6, pp. 1098-1104.
Lott T.J., et al., "Nucleotide Sequence Analysis of the 5-8s rDNA and Adjacent ITS2 Region of Candidaalbicans and Related Species," Yeast, 1993, vol. 9, pp. 1199-1206.
Louie L., et al., "Evaluation of Three Rapid Methods for Detection of Methicillin Resistance in *Staphylococcus aureus*," Journal of Clinical Microbiology, 2000, vol. 38 (6), pp. 2170-2173.
Love B.C., et al., "Cloning and Sequence of the GroESL Heat-Shock Operon of Pasteurella Multocida," Gene, 1995, vol. 166 (1), pp. 179-180.
Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.
Lowe T., et al., "A Computer Program for Selection of Oligonucleotide Primers for Polymerase Chain Reactions," Nucleic Acids Research, 1990, vol. 18 (7), pp. 1757-1761.

(56) References Cited

OTHER PUBLICATIONS

Lu X., et al., "Molecular Typing of Human Adenoviruses by PCR and Sequencing of a Partial Region of the Hexon Gene," Archives of Virology, 2006, vol. 151 (8), pp. 1587-1602.
Lubman D.M., Application for Continuation Grant by David Mitchell Lubman dated Jun. 4, 1996 and Jun. 14, 1996.
Lubman D.M., Application for Continuation Grant by David Mitchell Lubman dated Jun. 10, 1994 and Jun. 24, 1994.
Lubman D.M., Application for Grant by David Mitchell Lubman dated Sep. 1, 1994 and Sep. 27, 1994.
Lubman D.M., Application for Grant by David Mitchell Lubman dated Oct. 25, 1992 and Oct. 29, 1992.
Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.
Ludwig W., et al., "Bacterial Phylogeny Based on 16S and 23S rRNA Sequence Analysis," FEMS Microbiology Reviews, 1994, vol. 15 (2-3), pp. 155-173.
Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.
Ma X.X., et al., "Novel Type of Staphylococcal Cassette Chromosome Mec Identified in Community-Acquired Methicillin-Resistant Staphylococcus aureus Strains," Antimicrobial Agents and Chemotherapy, 2002, vol. 46 (4), pp. 1147-1152.
Mack D.H., et al., "A Sensitive Method for the Identification of Uncharacterized Viruses Related to known Virus Groups: Hepadnavirus Model System," Proceedings of the National Academy of Sciences, 1988, vol. 85 (18), pp. 6977-6981.
Magnuson V.L., et al., "Substrate Nucleotide-Determined Non-Templated Addition of Adenine by Taq DNA Polymerase: Implications for PCR-Based Genotyping and Cloning," BioTechniques, 1996, vol. 21 (4), pp. 700-709.
Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.
Malasig in M.D., et al., "Simplified Microneutralization Test for Serotyping Adenovirus Isolates," Journal of Clinical Microbiology, 2001, vol. 39 (8), pp. 2984-2986.
Mangrum J.D., et al., "Solution Composition and Thermal Denaturation for the Production of Single-Stranded PCR Amplicons: Piperidine-Induced Destabilization of the DNA Duplex," Journal of the American Society for Mass Spectrometry, 2002, vol. 13 (3), pp. 232-240.
Manian F.A., "Asymptomatic Nasal Carriage of Mupirocin-Resistant, Methicillin-Resistant Staphylococcus aureus (MRSA) in a Pet Dog Associated with MRSA Infection in Household Contacts," Clinical Infectious Diseases, 2003, vol. 36 (2), pp. e26-e28.
Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.
Marmur J., et al., "Strand Separation and Specific Recombination in Deoxyribonucleic Acids: Biological Studies," Proceedings of the National Academy of Sciences, 1960, vol. 46 (4), pp. 453-461.
Martemyanov K.A., et al., "Extremely Thermostable Elongation Factor (3 from Aquifer aeolicus: Cloning, Expression, Purification, and Characterization in a Heterologous Translation System," Protein Expression and Purification, 2000, vol. 18 (3), pp. 257-261.
Martineau F., et al., "Development of a PCR Assay for Identification of Staphylococci at Genus and Species Levels," Journal of Clinical Microbiology, 2001, vol. 39 (7), pp. 2541-2547.
Martineau F., et al., "Species-Specific and Ubiquitous-DNA-Based Assays for Rapid Identification of Staphylococcus aureus," Journal of Clinical Microbiology, 1998, vol. 36 (3), pp. 618-623.
Martin-Lopez J.V., et al., "Simultaneous PCR Detection of Ica Cluster and Methicillin and Mupirocinresistance Genes in Catheter-Isolated Staphylococcus," International Microbiology, 2004, vol. 7 (1), pp. 63-66.
Mason V.P., et al., "Diversity and linkage of Replication and Mobilisation Genes in Bacillus Rolling Irclereplicating Plasmids from Diverse Geographical Origins," FEMS Microbiology Ecology, 2002, vol. 42 (2), pp. 235-241.
Matray T.J., et al., "Synthesis and Properties of RNA Analogs-Oligoribonucleotide N3->p5 Phosphoramidates," Nucleic Acids Research, 1999, vol. 27 (20), pp. 3976-3985.
Matsuoka M., et al., "Characteristic Expression of Three Genes, msr(A), mph(C) and erm(Y), Thatconfer Resistance to Macrolide Antibiotics on Staphylococcus aureus," FEMS Microbiology Letters, 2003, vol. 220 (2), pp. 287-293.
May A.C., "Percent Sequence Identity: The Need to be Explicit," Structure, 2004, vol. 12 (5), pp. 737-738.
McCabe K.M., et al., "Bacterial Species Identification After DNA Amplification with a Universal Primer Pair," Molecular Genetics and Metabolism, 1999, vol. 66 (3), pp. 205-211.
McLafferty F.W., et al., "Comparison of Algorithms and Databases for Matching Unknown Mass Spectra," Journal of the American Society for Mass Spectrometry, 1998, vol. 9 (1), pp. 92-95.
McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.
Mehrotra M., et al., "Multiplex PCR for Detection of Genes for Staphylococcus aureus Enterotoxins, Exfoliative Toxins, Toxic Shock Syndrome Toxin 1, and Methicillin Resistance," Journal of Clinical Microbiology, 2000, vol. 38 (3), pp. 1032-1035.
Meiyu F., et al., "Detection of Flaviviruses by Reverse Transcriptase-Polymerase Chain Reaction with the Universal Primer Set," Microbiology and Immunology, 1997, vol. 41 (3), pp. 209-213.
Mellor J., et al., "Genotype Dependence of Hepatitis C Virus Load Measurement in Commercially Available Quantitative Assays," Journal of Clinical Microbiology, 1999, vol. 37 (8), pp. 2525-2532.
Merlino J., et al., "New Chromogenic Identification and Detection of Staphylococcus aureus and Methicillin-Resistant S. aureus," Journal of Clinical Microbiology, 2000, vol. 38 (6), pp. 2378-2380.
Merlino J., et al., "Rapid Detection of Non-Multidrug-Resistant and Multidrug-Resistant Methicillin-Resistant Staphylococcus aureus Using Cycling Probe Technology for the mecA Gene," European Journal of Clinical Microbiology and Infectious Diseases, 2003, vol. 22 (5), pp. 322-323.
Messmer T.O., et al., "Discrimination of Streptococcus pneumoniae from Other Upper respiratory tract Streptococci by Arbitrary Primed PCR," Clinical Biochemistry, 1995, vol. 28 (6), pp. 567-572.
Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.
Miller K.W., et al., "A Compendium of Human Mitochondrial DNA Control Region: Development of an International Standard Forensic Database," Croatian Medical Journal, 2001, vol. 42 (3), pp. 315-327.
Miragaia M., et al., "Genetic Diversity among Methicillin-Resistant Staphylococcus epidermidis(MRSE)," Microbial Drug Resistance, 2005, vol. 11 (2), pp. 83-93.
Miura-Ochiai R., et al., "Quantitative Detection and Rapid Identification of Human Adenoviruses," Journal of Clinical Microbiology, 2007, vol. 45 (3), pp. 958-967.
Mollet C., et al., "RpoB Sequence Analysis as a Novel Basis for Bacterial Identification," Molecular Microbiology, 1997, vol. 26 (5), pp. 1005-1011.
Monroy A.M., et al., "Exvaluation of Reverse Transcriptase Polymerase Chain Reaction for the Detection of Eastern Equine Encephalumyelitis Virus during Vector Surveillance," Journal of Medical Entomology, 1996, vol. 33 (3), pp. 449-457.

(56) References Cited

OTHER PUBLICATIONS

Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.
Moricca S., et al., "Detection of *Fusarium oxysporum* f.sp. Vasinfectum in Cotton Tissue by Polymerase Chain Reaction," Plant Pathology, 1998, vol. 47 (4), pp. 486-494.
Morinaga N., et al., "Purification, Cloning and Charactarizarion of Variant LukE-LukD with Strong Leukocidal Activity of Staphylococcal Bi-Component Leukotoxin Family," Microbiology and Immunology, 2003, vol. 47 (1), pp. 81-90.
Morse R., et al., "Nucleotide Sequence of Part of the ropC Gene Encoding the B Subunit of DNA Dependent RNA Polymerase from some Gram-Positive Bacteria and Comparative Amino Acid Sequence Analysis," Systematic and Applied Microbiology, 1996, vol. 19, pp. 150-157.
Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.
Muddiman D.C., et al., "Characterization of PCR Products from Bacilli Using Electrospray Ionization FTICR Mass Spectrometry," Analytical Chemistry, 1996, vol. 68 (21), pp. 3705-3712.
Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.
Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.
Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.
Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.
Muhammed W.T., et al., "Electrospray Ionization Quadrupole Time-of-Flight Mass Spectrometry and Guadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.
Murakami K., et al., "Identification of Methicillin-Resistant Strains of Staphylococci by Polymerase Chain Reaction," Journal of Clinical Microbiology, 1991, vol. 29 (10), pp. 2240-2244.
Murphy M., et al., "Multiple-Locus Variable Number of Tandem Repeat Analysis (MLVA) of Irish Verocytotoxigenic *Escherichia coli* 0157 from Feedlot Cattle: Uncovering Strain Dissemination Routes," BMC Veterinary Research, 2008, vol. 4 (2), pp. 1-9.
Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.
Na B.K., et al., "Detection and Typing of Respiratory Adenoviruses in a Single-Tube Multiplex Polymerase Chain Reaction," Journal of Medical Virology, 2002, vol. 66 (4), pp. 512-517.
Nagpal M.L., et al., "Utility of 16S-23S rRNA Spacer Region Methodology: How Similar are Interspace Regions within a Genome and Between Strains for Closely Related Organisms?," Journal of Microbiological Methods, 1998, vol. 33, pp. 211-219.
Nagy M., et al., "Sequence Analysis of Porcine Adenovirus Serotype 5 Fibre Gene: Evidence for Recombination," Virus Genes, 2002, vol. 24 (2), pp. 181-185.
Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.
Nakagawa S., et al., "Gene Sequences and Specific Detection for Panton-Valentine Leukocidin," Biochemical and Biophysical Research Communications, 2005, vol. 328 (4), pp. 995-1002.
Nakao H., et al., "Development of a Direct PCR Assay for Detection of the Diphtheria Toxin Gene," Journal of Clinical Microbiology, 1997, vol. 35 (7), pp. 1651-1655.
Narita S., et al., "Phage Conversion of Panton-Valentine Leukocidin in *Staphylococcus aureus*: Molecular Analysis of a PVL-Converting Phage, cpSLT," Gene, 2001, vol. 268 (1-2), pp. 195-206.
Naumov G.I., et al., "Discrimination Between the Soil Yeast Species Williopsis Saturnus and Williopsis Suaveolens by the Polymerase Chain Reaction with the Universal Primer N21," Microbiology, 2000, vol. 69 (2), pp. 229-233.
NEB Catalog, 1998/1999, pp. 1, 79, 121 and 284.
NEB Catalog 1998/1999, pp. 79, 121 and 284.
Neske F., et al., "Real-Time PCR for Diagnosis of Human Bocavirus Infections and Phylogenetic Analysis," Journal of Clinical Microbiology, 2007, vol. 45 (7), pp. 2116-2122.
Neumann G., et al., "Host Range Restriction and Pathogenicity in the Context of Influenza Pandemic," Emerging Infectious Diseases, 2006, vol. 12 (6), pp. 881-886.
New England BioLabs, "DNA Polymerase I, Large (Klenow) Fragment" [online][retrieved on Jan. 5, 2010], Retrived from the Internet: <URL: http://www.neb.com/nebecomm/products/productM0210.asp>, 3 pages.
New England BioLabs, "Endonuclease VIII" [online][retrieved on Jan. 5, 2010]. Retrived from the Internet:< URL: http://www.neb.com/nebecomm/products/productM0299.asp>, 2 pages.
New England BioLabs, "Fpg" [online][retrieved on Jan. 5, 2010]. Retrived from the Internet:<URL: http://www.neb.com/nebecomm/products/productM0240.asp>, 3 pages.
New England BioLabs, "T4 DNA Ligase" [online][retrieved on Jan. 5, 2010]. Retrived from the Internet:< URL: http://www.neb.com/nebecomm/products/productM0202.asp>, 3 pages.
New England BioLabs, "T4 Polynucleotide Kinas" [online][retrieved on Jan. 5, 2010]. Retrived from the Internet:< URL: http://www.neb.com/nebecomm/products/productM0201.asp>, 3 pages.
Newcombe J., et al., "PCR of Peripheral Blood for Diagnosis of Meningococcal Disease," Journal of Clinical Microbiology, 1996, vol. 34 (7), pp. 1637-1640.
Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.
Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.
Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.
Nilsson M., et al., "Evaluation of Mitochondrial DNA Coding Region Assays for Increased Discrimination in Forensic Analysis," Forensic Science International: Genetics, 2008, vol. 2 (1), pp. 1-8.
Nishikawa T., et al., "Reconstitution of Active Recombinant Ship Toxin (Stc)1 from Recombinant Stx1 -A and Sbt1 -B Subunits Independently Produced by *E. coli* Clones," FEMS Microbiol Letters, 1999, vol. 178 (1), pp. 13-18.
Noller A.C., et al., "Multilocus Variable-Number Tandem Repeat Analysis Distinguishes Outbreak and Sporadic *Escherichia coli* O157:H7 Isolates," Journal of Clinical Microbiology, 2003, vol. 41 (12), pp. 5389-5397.
Non-Final Office Action dated Feb. 2, 2007 for U.S. Appl. No. 10/844,938, filed May 12, 2004.
Non-Final Office Action dated Oct. 2, 2009 for U.S. Appl. No. 11/929,707, filed Oct. 30, 2007.
Non-Final Office Action dated Aug. 4, 2010 for U.S. Appl. No. 12/049,949, filed Mar. 17, 2008.

(56) References Cited

OTHER PUBLICATIONS

Non-Final Office Action dated Apr. 6, 2009 for U.S. Appl. No. 11/331,987, filed Jan. 13, 2006.
Non-Final Office Action dated Apr. 7, 2006 for U.S. Appl. No. 10/964,571, filed Oct. 12, 2004.
Non-Final Office Action dated Aug. 7, 2007 for U.S. Appl. No. 10/844,938, filed May 12, 2004.
Non-Final Office Action dated Jun. 10, 2009 for U.S. Appl. No. 10/844,938, filed May 12, 2004.
Non-Final Office Action dated Jan. 12, 2010 for U.S. Appl. No. 11/491,376, filed Jul. 21, 2006.
Non-Final Office Action dated Oct. 13, 2010 for U.S. Appl. No. 10/754,415, filed Jan. 9, 2004.
Non-Final Office Action dated Sep. 16, 2009 for U.S. Appl. No. 11/233,630, filed Sep. 21, 2005.
Non-Final Office Action dated Apr. 17, 2009 for U.S. Appl. No. 12/211,641, filed Sep. 16, 2008.
Non-Final Office Action dated Nov. 19, 2003 for U.S. Appl. No. 09/798,007, filed Mar. 2, 2001.
Non-Final Office Action dated Aug. 20, 2007 for U.S. Appl. No. 11/582,863, filed Oct. 17, 2006.
Non-Final Office Action dated May 20, 2008 for U.S. Appl. No. 10/844,938, filed May 12, 2004.
Non-Final Office Action dated Oct. 20, 2004 for U.S. Appl. No. 09/891,793, filed Jun. 26, 2001.
Non-Final Office Action dated Feb. 23, 2009 for U.S. Appl. No. 10/660,122, filed Sep. 11, 2003.
Non-Final Office Action dated May 26, 2010 for U.S. Appl. No. 11/869,449, filed Oct. 9, 2007.
Non-Final Office Action dated Jul. 27, 2006 for U.S. Appl. No. 11/209,439, filed Aug. 8, 2005.
Non-Final Office Action dated Jun. 28, 2010 for U.S. Appl. No. 11/930,002, filed Oct. 30, 2007.
Non-Final Office Action dated Sep. 28, 2009 for U.S. Appl. No. 11/930,017, filed Oct. 30, 2007.
Non-Final Office Action dated Dec. 29, 2010 for U.S. Appl. No. 12/616,422, filed Nov. 11, 2009.
Non-Final Office Action dated Apr. 30, 2010 for U.S. Appl. No. 11/930,108, filed Oct. 31, 2007.
Norder H., et al., "Typing of Hepatitis B Virus Genomes by a Simplified Polymerase Chain Reaction," Journal of Medical Virology, 1990, vol. 31 (3), pp. 215-221.
Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.
Notice of Allowance dated Apr. 1, 2011 for U.S. Appl. No. 11/233,630, filed Sep. 21, 2005.
Notice of Allowance dated Jun. 3, 2009 for U.S. Appl. No. 11/331,978, filed Jan. 13, 2006.
Notice of Allowance dated Aug. 5, 2010 for U.S. Appl. No. 11/233,630, filed Sep. 21, 2005.
Notice of Allowance dated Aug. 6, 2009 for U.S. Appl. No. 10/728,486, filed Dec. 5, 2003.
Notice of Allowance dated Apr. 8, 2010 for U.S. Appl. No. 10/891,337, filed Jul. 14, 2004.
Notice of Allowance dated Jun. 9, 2011 for U.S. Appl. No. 11/331,987, filed Jan. 13, 2006.
Notice of Allowance dated Jun. 9, 2011 for U.S. Appl. No. 11/491,376, filed Jul. 21, 2006.
Notice of Allowance dated Dec. 10, 2010 for U.S. Appl. No. 11/233,630, filed Sep. 21, 2005.
Notice of Allowance dated Dec. 10, 2010 for U.S. Appl. No. 11/491,376, filed Jul. 21, 2006.
Notice of Allowance dated Jan. 11, 2010 for U.S. Appl. No. 10/891,337, filed Jul. 14, 2004.
Notice of Allowance dated Nov. 12, 2009 for U.S. Appl. No. 10/728,486, filed Dec. 5, 2003.
Notice of Allowance dated Dec. 15, 2008 for U.S. Appl. No. 11/331,978, filed Jan. 13, 2006.
Notice of Allowance dated Sep. 18, 2009 for U.S. Appl. No. 10/660,998, filed Sep. 12, 2003.
Notice of Allowance dated Nov. 24, 2009 for U.S. Appl. No. 11/331,978, filed Jan. 13, 2006.
Notice of Allowance dated May 25, 2011 for U.S. Appl. No. 11/929,707, filed Oct. 30, 2007.
Notice of Allowance dated Oct. 29, 2009 for U.S. Appl. No. 10/660,122, filed Sep. 11, 2003.
Nubel U., et al., "PCR Primers to Amplify 16S rRNA Genes from Cyanobacteria," Applied and Environmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.
Null A.P., et al., "Evaluation of Sample Preparation Techniques for Mass Measurements of PCR Products Using ESIFT-ICR Mass Spectrometry," The American Society for Mass Spectrometry, 2002, vol. 13 (4), pp. 338-344.
Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.
Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.
Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.
Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.
Nunes E.L., et al., "Detection of IleS-2 Gene Encoding Mupirocin Resistance in Methicillin-Resistant *Staphylococcus aureus* by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain Reaction Standards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased Foresnic Efficiency of DNA Fingerprints Through Simultaneous Resolution of Length and Nucleotide Variability by High-Performance Mass Spectrometry," Human Mutation, 2008, vol. 29 (3), pp. 427-432.
Oberste M.S., et al., "Improved Molecular Identification of Enteroviruses by RT-PCR and Amplicon Sequencing," Journal of Clinical Virology, 2003, vol. 26 (3), pp. 375-377.
Oberste M.S., et al., "Molecular Epidemiology and Type-Specific Detection of Echovirus 11 Isolates from the Americas, Europe, Africa, Australia, Southern Asia and the Middle East," Virus Research, 2003, vol. 91 (2), pp. 241-248.
Oberste M.S., et al., "Molecular Phylogeny and Proposed Classification of the Simian Picornaviruses," Journal of Virology, 2002, vol. 76 (3), pp. 1244-1251.
Office Action dated Apr. 1, 2004 for U.S. Appl. No. 10/156,608, filed May 24, 2002.
Office Action dated May 1, 2006 for U.S. Appl. No. 10/660,998, filed Sep. 12, 2003.
Office Action dated Feb. 2, 2011 for U.S. Appl. No. 11/869,449, filed Oct. 9, 2007.

(56) References Cited

OTHER PUBLICATIONS

Office Action dated Jan. 2, 2009 for U.S. Appl. No. 11/060,135, filed Feb. 17, 2005.
Office Action dated Jun. 2, 2006 for U.S. Appl. No. 10/933,928, filed Sep. 3, 2004.
Office Action dated Jun. 2, 2008 for U.S. Appl. No. 11/331,978, filed Jan. 13, 2006.
Office Action dated Oct. 2, 2008 for U.S. Appl. No. 11/233,630, filed Sep. 21, 2005.
Office Action dated Oct. 2, 2009 for Japanese Application No. 2005508560 filed Dec. 5, 2003.
Office Action dated Aug. 3, 2006 for U.S. Appl. No. 10/660,998, filed Sep. 12, 2003.
Office Action dated Aug. 3, 2009 for U.S. Appl. No. 11/754,174, filed May 25, 2007.
Office Action dated Dec. 3, 2003 for U.S. Appl. No. 10/325,527, filed Dec. 18, 2002.
Office Action dated Feb. 3, 2011 for U.S. Appl. No. 12/326,800, filed Dec. 2, 2008.
Office Action dated Nov. 3, 2008 for U.S. Appl. No. 10/728,486, filed Dec. 5, 2003.
Office Action dated Apr. 4, 2008 for U.S. Appl. No. 10/829,826, filed Apr. 22, 2004.
Office Action dated Dec. 4, 2006 for Indian Application No. 1136KOLNP2003 filed Mar. 4, 2002.
Office Action dated Feb. 4, 2009 for U.S. Appl. No. 11/404,561, filed Apr. 12, 2006.
Office Action dated Jun. 4, 2009 for U.S. Appl. No. 10/754,415, filed Jan. 9, 2004.
Office Action dated May 4, 2010 for U.S. Appl. No. 90/010,447, filed Apr. 9, 2009.
Office Action dated May 4, 2010 for U.S. Appl. No. 90/010,448, filed Apr. 9, 2009.
Office Action dated Nov. 4, 2009 for European Application No. 02709785.6 filed Mar. 4, 2002.
Office Action dated Sep. 4, 2008 for Australian Application No. 2003297687 filed Dec. 5, 2003.
Office Action dated Aug. 5, 2010 for European Application No. 02709785.6 filed Mar. 4, 2002.
Office Action dated Sep. 5, 2006 for U.S. Appl. No. 10/660,996, filed Sep. 12, 2003.
Office Action dated Jan. 6, 2011 for Israel Application No. 157661 filed Mar. 4, 2002.
Office Action dated Jul. 6, 2006 for U.S. Appl. No. 10/660,122, filed Sep. 11, 2003.
Office Action dated Jul. 6, 2007 for U.S. Appl. No. 10/829,826, filed Apr. 22, 2004.
Office Action dated Mar. 6, 2009 for U.S. Appl. No. 11/233,630, filed Sep. 21, 2005.
Office Action dated Nov. 6, 2002 for U.S. Appl. No. 09/798,007, filed Mar. 2, 2001.
Office Action dated Apr. 7, 2009 for Canadian Application No. 2525498 filed May 13, 2004.
Office Action dated Apr. 7, 2009 for European Application No. 07760292.8 filed Apr. 6, 2007.
Office Action dated Apr. 7, 2009 for U.S. Appl. No. 10/660,998, filed Sep. 12, 2003.
Office Action dated Aug. 7, 2007 for U.S. Appl. No. 10/660,998, filed Sep. 12, 2003.
Office Action dated Feb. 7, 2008 for European Application No. 03796752.8 filed Dec. 5, 2003.
Office Action dated Jun. 7, 2010 for European Application No. 06800205.4 filed Jul. 27, 2006.
Office Action dated Jan. 8, 2003 for U.S. Appl. No. 09/798,007, filed Mar. 2, 2001.
Office Action dated Jan. 8, 2007 for U.S. Appl. No. 09/891,793, filed Jun. 26, 2001.
Office Action dated Mar. 8, 2005 for U.S. Appl. No. 09/891,793, filed Jun. 26, 2001.
Office Action dated Mar. 8, 2007 for U.S. Appl. No. 11/060,135, filed Feb. 17, 2005.
Office Action dated Sep. 8, 2006 for Chinese Application No. 02809122.1 filed Mar. 4, 2002.
Office Action dated Dec. 9, 2004 for U.S. Appl. No. 10/156,608, filed May 24, 2002.
Office Action dated Dec. 9, 2009 for U.S. Appl. No. 90/010,210, filed Jun. 27, 2008.
Office Action dated Dec. 9, 2009 for U.S. Appl. No. 90/010,447, filed Apr. 9, 2009.
Office Action dated Dec. 9, 2009 for U.S. Appl. No. 90/010,448, filed Apr. 9, 2009.
Office Action dated Feb. 9, 2007 for Chinese Application No. 02809122.1 filed Mar. 4, 2002.
Office Action dated Jan. 9, 2008 for Japanese Application No. 2002570692 filed Mar. 4, 2002.
Office Action dated Jul. 9, 2008 for U.S. Appl. No. 10/660,122, filed Sep. 11, 2003.
Office Action dated Jul. 9, 2008 for U.S. Appl. No. 11/331,987, filed Jan. 13, 2006.
Office Action dated Jul. 9, 2009 for U.S. Appl. No. 10/829,826, filed Apr. 22, 2004.
Office Action dated Mar. 9, 2004 for U.S. Appl. No. 09/891,793, filed Jun. 26, 2001.
Office Action dated Nov. 9, 2010 for U.S. Appl. No. 11/331,987, filed Jan. 13, 2006.
Office Action dated Dec. 10, 2008 for U.S. Appl. No. 10/829,826, filed Apr. 22, 2004.
Office Action dated Dec. 10, 2009 for U.S. Appl. No. 11/929,910, filed Oct. 30, 2007.
Office Action dated Feb. 10, 2005 for U.S. Appl. No. 09/798,007, filed Mar. 2, 2001.
Office Action dated Feb. 10, 2006 for Australian Application No. 2002244250 filed Mar. 4, 2002.
Office Action dated Jun. 10, 2009 for U.S. Appl. No. 90/010,210, filed Jun. 27, 2008.
Office Action dated Jun. 10, 2010 for U.S. Appl. No. 90/010,447, filed Apr. 9, 2009.
Office Action dated Jun. 10, 2010 for U.S. Appl. No. 90/010,448, filed Apr. 9, 2009.
Office Action dated Oct. 10, 2007 for U.S. Appl. No. 10/754,415, filed Jan. 9, 2004.
Office Action dated Sep. 10, 2008 for Australian Application No. 2003302236 filed Dec. 5, 2003.
Office Action dated Aug. 11, 2005 for U.S. Appl. No. 09/891,793, filed Jun. 26, 2001.
Office Action dated Aug. 11, 2010 for U.S. Appl. No. 90/010,447, filed Apr. 9, 2009.
Office Action dated Aug. 11, 2010 for U.S. Appl. No. 90/010,448, filed Apr. 9, 2009.
Office Action dated Dec. 11, 2007 for U.S. Appl. No. 10/660,998, filed Sep. 12, 2003.
Office Action dated Jul. 11, 2003 for U.S. Appl. No. 09/798,007, filed Mar. 2, 2001.
Office Action dated Jun. 11, 2010 for U.S. Appl. No. 90/010,210, filed Jun. 27, 2008.
Office Action dated Mar. 11, 2005 for U.S. Appl. No. 10/325,527, filed Dec. 18, 2002.
Office Action dated May 11, 2007 for U.S. Appl. No. 10/728,486, filed Dec. 5, 2003.
Office Action dated Jul. 12, 2006 for U.S. Appl. No. 09/891,793, filed Jun. 26, 2001.
Office Action dated Jul. 12, 2006 for U.S. Appl. No. 10/660,996, filed Sep. 12, 2003.
Office Action dated Jun. 12, 2008 for U.S. Appl. No. 10/754,415, filed Jan. 9, 2004.
Office Action dated Jun. 12, 2009 for Chinese Application No. 200480016187.9 filed May 13, 2004.
Office Action dated May 12, 2002 for U.S. Appl. No. 09/798,007, filed Mar. 2, 2001.
Office Action dated Aug. 13, 2009 for U.S. Appl. No. 11/674,538, filed Feb. 13, 2007.

(56) References Cited

OTHER PUBLICATIONS

Office Action dated Jul. 13, 2004 for U.S. Appl. No. 09/891,793, filed Jun. 26, 2001.
Office Action dated Jul. 13, 2007 for U.S. Appl. No. 11/233,630, filed Sep. 21, 2005.
Office Action dated Jul. 13, 2010 for U.S. Appl. No. 11/929,930, filed Oct. 30, 2007.
Office Action dated Mar. 13, 2006 for U.S. Appl. No. 10/754,415, filed Jan. 9, 2004.
Office Action dated Nov. 13, 2003 for U.S. Appl. No. 09/891,793, filed Jun. 26, 2001.
Office Action dated Sep. 13, 2006 for U.S. Appl. No. 09/891,793, filed Jun. 26, 2001.
Office Action dated Jul. 14, 2004 for U.S. Appl. No. 10/326,642, filed Dec. 18, 2002.
Office Action dated Jun. 14, 2004 for U.S. Appl. No. 09/891,793, filed Jun. 26, 2001.
Office Action dated Mar. 14, 2011 for U.S. Appl. No. 11/930,002, filed Oct. 30, 2007.
Office Action dated Aug. 15, 2008 for U.S. Appl. No. 11/331,978, filed Jan. 13, 2006.
Office Action dated Dec. 15, 2008 for Israel Application No. 157661 filed Mar. 4, 2002.
Office action dated Dec. 15, 2010 for Canadian Application No. 2508726 filed Dec. 5, 2003.
Office Action dated Jan. 15, 2008 for Israel Application No. 157661 filed Mar. 4, 2002.
Office Action dated Jul. 15, 2009 for U.S. Appl. No. 11/060,135, filed Feb. 17, 2005.
Office Action dated Mar. 15, 2010 for European Application No. 08730682.5 filed Feb. 25, 2008.
Office Action dated Nov. 15, 2007 for U.S. Appl. No. 11/331,978, filed Jan. 13, 2006.
Office Action dated Sep. 15, 2005 for U.S. Appl. No. 10/156,608, filed May 24, 2002.
Office Action dated Apr. 16, 2002 for U.S. Appl. No. 09/798,007, filed Mar. 2, 2001.
Office Action dated Apr. 16, 2008 for U.S. Appl. No. 11/233,630, filed Sep. 21, 2005.
Office Action dated Apr. 16, 2009 for U.S. Appl. No. 90/010,210, filed Jun. 27, 2008.
Office Action dated Aug. 16, 2004 for U.S. Appl. No. 10/325,527, filed Dec. 18, 2002.
Office Action dated Aug. 16, 2010 for U.S. Appl. No. 11/929,707, filed Oct. 30, 2007.
Office Action dated Dec. 16, 2009 for U.S. Appl. No. 11/582,860, filed Oct. 17, 2006.
Office Action dated Feb. 16, 2011 for U.S. Appl. No. 11/929,910, filed Oct. 30, 2007.
Office Action dated Jul. 16, 2007 for U.S. Appl. No. 11/331,987, filed Jan. 13, 2006.
Office Action dated Mar. 16, 2006 for U.S. Appl. No. 09/891,793, filed Jun. 26, 2001.
Office Action dated Mar. 16, 2010 for Canadian Application No. 2616281 filed Jul. 21, 2006.
Office Action dated May 16, 2008 for U.S. Appl. No. 11/404,561, filed Apr. 12, 2006.
Office Action dated Nov. 16, 2009 for Japanese Application No. 2005508488 filed Dec. 5, 2003.
Office Action dated Jun. 17, 2008 for U.S. Appl. No. 11/582,863, filed Oct. 17, 2006.
Office Action dated Mar. 17, 2006 for U.S. Appl. No. 10/660,122, filed Sep. 11, 2003.
Office Action dated Nov. 17, 2006 for U.S. Appl. No. 10/754,415, filed Jan. 9, 2004.
Office Action dated Oct. 17, 2007 for U.S. Appl. No. 10/728,486, filed Dec. 5, 2003.
Office Action dated Oct. 17, 2008 for U.S. Appl. No. 11/331,978, filed Jan. 13, 2006.
Office Action dated Sep. 17, 2008 for European Application No. 03796752.8 filed Dec. 5, 2003.
Office Action dated Sep. 17, 2008 for U.S. Appl. No. 10/660,122, filed Sep. 11, 2003.
Office Action dated Feb. 18, 2010 for European Application No. 03814656.9 filed Dec. 5, 2003.
Office Action dated Jan. 18, 2011 for U.S. Appl. No. 11/930,108, filed Oct. 31, 2007.
Office Action dated May 18, 2005 for New Zealand Application No. 527857 filed Mar. 4, 2002.
Office Action dated Sep. 18, 2006 for U.S. Appl. No. 10/660,997, filed Sep. 12, 2003.
Office Action dated Sep. 18, 2008 for Australian Application No. 2003298030 filed Dec. 5, 2003.
Office Action dated Sep. 18, 2008 for U.S. Appl. No. 10/660,998, filed Sep. 12, 2003.
Office Action dated Jan. 19, 2007 for U.S. Appl. No. 11/059,776, filed Feb. 17, 2005.
Office Action dated May 19, 2005 for U.S. Appl. No. 09/891,793, filed Jun. 26, 2001.
Office Action dated Nov. 19, 2004 for U.S. Appl. No. 10/156,608, filed May 24, 2002.
Office Action dated Oct. 19, 2007 for U.S. Appl. No. 11/210,516, filed Aug. 24, 2005.
Office Action dated Sep. 19, 2006 for U.S. Appl. No. 10/660,122, filed Sep. 11, 2003.
Office Action dated Sep. 19, 2007 for U.S. Appl. No. 10/660,122, filed Sep. 11, 2003.
Office Action dated Apr. 20, 2007 for U.S. Appl. No. 10/660,122, filed Sep. 11, 2003.
Office Action dated Apr. 20, 2009 for U.S. Appl. No. 10/891,337, filed Jul. 14, 2004.
Office Action dated Dec. 20, 2006 for U.S. Appl. No. 10/728,486, filed Dec. 5, 2003.
Office Action dated Jul. 20, 2005 for U.S. Appl. No. 10/156,608, filed May 24, 2002.
Office Action dated Jun. 20, 2002 for U.S. Appl. No. 09/798,007, filed Mar. 2, 2001.
Office Action dated Nov. 20, 2003 for U.S. Appl. No. 10/323,438, filed Dec. 18, 2002.
Office Action dated Nov. 20, 2006 for U.S. Appl. No. 09/891,793, filed Jun. 26, 2001.
Office Action dated Nov. 20, 2006 for European Application No. 02709785.6 filed Mar. 4, 2002.
Office Action dated Sep. 20, 2010 for U.S. Appl. No. 90/010,447, filed Apr. 9, 2009.
Office Action dated Sep. 20, 2010 for U.S. Appl. No. 90/010,448, filed Apr. 9, 2009.
Office Action dated Apr. 21, 2009 for U.S. Appl. No. 90/010,209, filed Jun. 27, 2008.
Office Action dated Mar. 21, 2008 for U.S. Appl. No. 10/660,122, filed Sep. 11, 2003.
Office Action dated May 21, 2008 for U.S. Appl. No. 10/943,344, filed Sep. 17, 2004.
Office Action dated Nov. 21, 2003 for U.S. Appl. No. 10/326,642, filed Dec. 18, 2002.
Office Action dated Nov. 21, 2006 for U.S. Appl. No. 10/660,097, filed Sep. 12, 2003.
Office Action dated Oct. 21, 2005 for U.S. Appl. No. 10/326,641, filed Dec. 18, 2002.
Office Action dated Oct. 21, 2009 for U.S. Appl. No. 12/326,800, filed Dec. 2, 2008.
Office Action dated Apr. 22, 2009 for U.S. Appl. No. 11/491,376, filed Jul. 21, 2006.
Office Action dated Jul. 22, 2008 for U.S. Appl. No. 90/010,209, filed Jun. 27, 2008.
Office Action dated Jul. 22, 2008 for U.S. Appl. No. 90/010,210, filed Jun. 27, 2008.
Office Action dated Nov. 22, 2006 for U.S. Appl. No. 10/660,996, filed Sep. 12, 2003.
Office Action dated Oct. 22, 2007 for U.S. Appl. No. 11/331,987, filed Jan. 13, 2006.

(56) References Cited

OTHER PUBLICATIONS

Office Action dated Sep. 22, 2003 for U.S. Appl. No. 09/798,007, filed Mar. 2, 2001.
Office Action dated Sep. 22, 2010 for Canadian Application No. 2510007 filed Dec. 5, 2003.
Office Action dated Apr. 23, 2010 for U.S. Appl. No. 90/010,210, filed Jun. 27, 2008.
Office Action dated Feb. 23, 2009 for U.S. Appl. No. 10/943,344, filed Sep. 17, 2004.
Office Action dated Jan. 23, 2008 for U.S. Appl. No. 10/728,486, filed Dec. 5, 2003.
Office Action dated Jan. 23, 2008 for U.S. Appl. No. 11/059,776, filed Feb. 17, 2005.
Office Action dated May 23, 2003 for U.S. Appl. No. 09/891,793, filed Jun. 26, 2001.
Office Action dated May 23, 2005 for U.S. Appl. No. 10/156,608, filed May 24, 2002.
Office Action dated Oct. 23, 2003 for New Zealand Application No. 527857 filed Mar. 4, 2002.
Office Action dated Apr. 24, 2009 for U.S. Appl. No. 90/010,447, filed Apr. 9, 2009.
Office Action dated Apr. 24, 2009 for U.S. Appl. No. 90/010,448, filed Apr. 9, 2009.
Office Action dated Aug. 24, 2010 for U.S. Appl. No. 90/010,210, filed Jun. 27, 2008.
Office Action dated Dec. 24, 2004 for New Zealand Application No. 527857 filed Mar. 4, 2002.
Office Action dated Feb. 24, 2004 for U.S. Appl. No. 10/326,642, filed Dec. 18, 2002.
Office Action dated Jan. 24, 2005 for U.S. Appl. No. 10/326,642, filed Dec. 18, 2002.
Office Action dated Jan. 24, 2007 for U.S. Appl. No. 10/660,998, filed Sep. 12, 2003.
Office Action dated Jul. 24, 2007 for Mexican Application No. PAA2003007927 filed Sep. 2, 2003.
Office Action dated Jul. 24, 2007 for U.S. Appl. No. 11/060,135, filed Feb. 17, 2005.
Office Action dated Jul. 24, 2009 for U.S. Appl. No. 11/754,182, filed May 25, 2007.
Office Action dated Jun. 24, 2008 for European Application No. 06800205.4 filed Jul. 27, 2006.
Office Action dated Mar. 24, 2011 for U.S. Appl. No. 11/929,930, filed Oct. 30, 2007.
Office Action dated Nov. 24, 2009 for Canadian Application No. 2607468 filed Apr. 21, 2006.
Office Action dated Nov. 24, 2009 for U.S. Appl. No. 90/010,210, filed Jun. 27, 2008.
Office Action dated Sep. 24, 2009 for U.S. Appl. No. 90/010,210, filed Jun. 27, 2008.
Office Action dated Aug. 25, 2009 for U.S. Appl. No. 11/754,169, filed May 25, 2007.
Office Action dated Jun. 25, 2009 for U.S. Appl. No. 11/869,449, filed Oct. 9, 2007.
Office Action dated Jun. 25, 2009 for U.S. Appl. No. 90/010,210, filed Jun. 27, 2008.
Office Action dated Mar. 25, 2008 for U.S. Appl. No. 11/060,135, filed Feb. 17, 2005.
Office Action dated Nov. 25, 2009 for Japanese Application No. 2006533082 filed May 13, 2004.
Office Action dated Aug. 26, 2003 for U.S. Appl. No. 09/891,793, filed Jun. 26, 2001.
Office Action dated Aug. 26, 2010 for Canadian Application No. 2508584 filed Dec. 5, 2003.
Office Action dated Jul. 26, 2004 for U.S. Appl. No. 10/323,438, filed Dec. 18, 2002.
Office Action dated May 26, 2005 for U.S. Appl. No. 10/156,608, filed May 24, 2002.
Office Action dated May 26, 2006 for U.S. Appl. No. 10/660,997, filed Sep. 12, 2003.
Office Action dated Feb. 27, 2003 for U.S. Appl. No. 09/798,007, filed Mar. 2, 2001.
Office Action dated Feb. 27, 2007 for U.S. Appl. No. 10/754,415, filed Jan. 9, 2004.
Office Action dated Feb. 27, 2007 for U.S. Appl. No. 10/943,344, filed Sep. 17, 2004.
Office Action dated Jul. 27, 2006 for U.S. Appl. No. 10/728,486, filed Dec. 5, 2003.
Office Action dated Jul. 27, 2009 for Canadian Application No. 2439655 filed Mar. 4, 2002.
Office Action dated Aug. 28, 2006 for U.S. Appl. No. 10/754,415, filed Jan. 9, 2004.
Office Action dated Feb. 28, 2006 for U.S. Appl. No. 10/660,996, filed Sep. 12, 2003.
Office Action dated Jul. 28, 2009 for U.S. Appl. No. 11/754,163, filed May 25, 2007.
Office Action dated Jul. 28, 2010 for U.S. Appl. No. 90/010,210, filed Jun. 27, 2008.
Office Action dated May 28, 2003 for U.S. Appl. No. 09/798,007, filed Mar. 2, 2001.
Office Action dated Dec. 29, 2009 for U.S. Appl. No. 10/829,826, filed Apr. 22, 2004.
Office Action dated Dec. 29, 2009 for U.S. Appl. No. 11/210,516, filed Aug. 24, 2005.
Office Action dated Mar. 29, 2010 for Australian Application No. 2006272776 filed Jul. 21, 2006.
Office Action dated May 29, 2007 for U.S. Appl. No. 11/059,776, filed Feb. 17, 2005.
Office Action dated Oct. 29, 2009 for U.S. Appl. No. 90/010,447, filed Apr. 9, 2009.
Office Action dated Oct. 29, 2009 for U.S. Appl. No. 90/010,448, filed Apr. 9, 2009.
Office Action dated Aug. 30, 2007 for U.S. Appl. No. 10/754,415, filed Jan. 9, 2004.
Office Action dated Jul. 30, 2008 for Australian Application No. 2004248107 filed Apr. 23, 2004.
Office Action dated Jul. 30, 2009 for Japanese Application No. 2002570692 filed Mar. 4, 2002.
Office Action dated Jun. 30, 2004 for U.S. Appl. No. 09/798,007, filed Mar. 2, 2001.
Office Action dated Jun. 30, 2010 for U.S. Appl. No. 90/010,210, filed Jun. 27, 2008.
Office Action dated Jun. 30, 2010 for U.S. Appl. No. 90/010,447, filed Apr. 9, 2009.
Office Action dated Jun. 30, 2010 for U.S. Appl. No. 90/010,448, filed Apr. 9, 2009.
Office Action dated May 30, 2006 for U.S. Appl. No. 10/660,996, filed Sep. 12, 2003.
Office Action dated Nov. 30, 2009 for U.S. Appl. No. 10/660,122, filed Sep. 11, 2003.
Office Action dated Sep. 30, 2005 for Chinese Application No. 02809122.1 filed Mar. 4, 2002.
Office Action dated Jan. 31, 2003 for U.S. Appl. No. 09/793,007, filed Mar. 2, 2001.
Office Action dated Jan. 31, 2007 for Philippines Application No. PH12003500824 filed Mar. 4, 2002.
Office Action dated Oct. 6, 2008 for U.S. Appl. No. 11/368,233, filed Mar. 3, 2006.
Office Action dated Jun. 22, 2007 for U.S. Appl. No. 11/368,233, filed Mar. 3, 2006.
Office Action dated Jun. 22, 2009 for U.S. Appl. No. 11/368,233, filed Mar. 3, 2006.
O"Guinn M.L., et al., "Field Detection of Eastern Equine Encephalitis Virus in the Amazon Basin Region of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship Between Mutations in the DNA Gyrase and Topoisomerase IV Genes and Nadifloxacin Resistance in Clinically Isolated Quinolone-Resistant *Staphylococcus aureus*," Journal of Infection and Chemotherapy, 2001, vol. 7 (3), pp. 191-194.

(56) References Cited

OTHER PUBLICATIONS

Okada M., et al., "Detection and Sequence-Based Typing of Human Adenoviruses Using Sensitiveuniversal Primer Sets for the Hexon Gene," Archives of Virology, 2007, vol. 152 (1), pp. 1-9.

Okuma K., et al., "Dissemination of New Methicillin-Resistant *Staphylococcus aureus* Clones in the Community," Journal of Clinical Microbiology, 2002, vol. 40 (11), pp. 4289-4294.

Oliveira D.C., et al., "Genetic Organization of the Downstream Region of the mecA Element inMethicillin-Resistant *Staphylococcus aureus* Isolates Carrying Different Polymorphisms of This Region," Antimicrobial Agents and Chemotherapy, 2000, vol. 44 (7), pp. 1906-1910.

Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.

Olsen B., et al., "Transhemispheric Exchange of Lyme Disease Spyrochetes by Seabirds," Journal of Clinical Microbiology, 1995, vol. 33 (12), pp. 3270-3274.

Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.

Ostrander E.A., et al., "Identification and Characterization of Dinucleotide Repeat (CA)n Markers for Genetic Mapping in Dog," Genomics, 1993, vol. 16 (1), pp. 207-213.

Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.

Palys T., et al., "Discovery and Classification of Ecological Diversity in the Bacterial World: the Role of DNA Sequence Data," International Journal of Systematic Bacteriology, 1997, vol. 47 (4), pp. 1145-1156.

Pan Z.Q., et al., "Oligonucleotide-Targeted Degradation of U1 and U2 snRNAs Reveals Differential Interactions of Simian Virus 40 pre-mRNAs with snRNPs," Nucleic Acids Research, 1989, vol. 17 (16), pp. 6553-6568.

Pannetier C., et al., "Quantitative Titration of Nucleic Acids by Enzymatic Amplification Reactions Run to Saturation," Nucleic Acids Research, 1993, vol. 21 (3), pp. 577-583.

Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.

Partial European Search Report for Application No. EP01106974, dated Dec. 16, 2002, 2 pages.

Partial International Search Report for Application No. PCT/US2009/058759, dated Dec. 12, 2009, 2 pages.

Partial International Search Report for Application No. PCT/US2009/059169, dated Jan. 12, 2010, 7 pages.

Pastorino B., et al., "Development of a TagMan PCR Assay Without RNA Extraction Step for the Detection and Quantification of African Chikungunya Viruses," Journal of Virological Methods, 2005, vol. 124 (1-2), pp. 65-71.

Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.

Pawa A., et al., "Co-Transfer of Plasmids in Association with Conjugative Transfer of Mupirocin or Mupirocin and Penicillin Resistance in Methicillin-Resistant *Staphylococcus aureus*," Journal of Medicinal Microbiology, 2000, vol. 49 (12), pp. 1103-1107.

Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.

Pei Y., et al., "Molecular Characterization of Enterohemorrhagic *Escherichia coli* O157:H7 Isolates Dispersed Across Japan by Pulsed-Field Gel Electrophoresis and Multiple-Locus Variable-Number Tandem Repeat Analysis," Japanese Journal of Infectious Diseases, 2008, vol. 61 (1), pp. 58-64.

Peng X., et al., "Rapid Detection of Shigella Species in Environmental Sewage by an Immunocapture PCR with Universal Primers," Applied and Environmental Microbiology, 2002, vol. 68 (5), pp. 2580-2583.

Perez-Roth E., et al., "Multiplex PCR for Simultaneous Identification of *Staphylococcus aureus* and Detection of Methicillin and Mupirocin Resistance," Journal of Clinical Microbiology, 2001, vol. 39 (11), pp. 4037-4041.

Peters S.E., et al., "Quantification of the Detection of Pneumocystis Carinii by DNA Amplification," Molecular and Cellur Probes, 1992, vol. 6 (2), pp. 115-117.

Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.

Pfeffer M., et al., "Specific Detection of Chikungunya Virus Using a RT-PCR/Nested PCR Combination," Journal of Veterinary Medicine B, 2002, vol. 49 (1), pp. 49-54.

Pieles U., et al., "Matrix-Assisted Laser Desorption Ionization Time-of-Flight Spectrometry: APowerful Tool for the Mass and Sequence Analysis of Natural and Modified Oligonucleotides, 787 reexamination," Nucleic Acids Research, 1993, vol. 21 (14), pp. 3191-3196.

Pillai S.D., et al., "Rapid Molecular Detection of Microbial Pathogens: Breakthroughs and Challenges," Archives of Virology, 1997, vol. 13, pp. 67-82.

Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.

Poddar S.K., et al., "Detection of Adenovirus using PCR and Molecular Beacon," Journal of Virological Methods, 1999, vol. 82 (1), pp. 19-26.

Pomerantz S.C., et al., "Determination of Oligonucleotide Composition from Mass Spectrometrically Measured Molecular Weight," Journal of the American Society for Mass Spectrometry, 1993, vol. 4 (3), pp. 204-209.

Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.

Pring-Akerblom P., et al., "PCR-Based Detection and Typing of Human Adenoviruses in Clinical Samples," Research in Virology, 1997, vol. 148 (3), pp. 225-231.

Promega. T4 Polynucleotide Kinase, Technical Bulletin No. 519, 2002.

Puthavathana P., et al., "Molecular Characterization of the Complete Genome of Human Influenza H5N1 Virus Isolates from Thailand," Journal of General Virology, 2005, vol. 86 (2), pp. 423-433.

Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.

Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.

Ramisse V., et al., "Identification and Characterization of Bacillus Anthracis by Multiplex PCR Analysis of Sequences on Plasmids pX01 and pX02 and Chromosomal DNA," Fems Microbiology Letters, 1996, vol. 145 (1), pp. 9-16.

Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.

Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.

Reischl U., "Application of Molecular Biology-Based Methods to theDiagnosis of Infectious Diseases 1, e72-e77.," Frontiers in Bioscience, 1996, vol. 1 (1), pp. e72-e77.

Reischl U., et al., "Rapid Identification of Methicillin-Resistant *Staphylococcus aureus* and Simultaneous Species Confirmation

(56) References Cited

OTHER PUBLICATIONS

Using Real-Time Fluorescence PCR," Journal of Clinical Microbiology, 2000, vol. 38 (6), pp. 2429-2433.
Roberts M.M., "Three-Dimensional Structure of the Adenovirus Major Coat Protein Hexon," Science, 1986, vol. 232 (4754), pp. 1148-1151.
Roberts M.S., et al., "Recombination and Migration Rates in Natural Populations of Bacillus Subtilis and Bacillus Mojavensis," Evolution, 1995, vol. 49 (6), pp. 1081-1094.
Robinson D.A., et al., "Multilocus Sequence Typing and the Evolution of Methicillin-Resistant *Staphylococcus aureus*," Clinical Microbiology and Infection, 2004, vol. 10, pp. 92-97.
Rong S., et al., "Design and Application of 60mer Oligonucleotide Microarray in SARS Coronavirus Detection," Chinese Science Bulletin, 2003, vol. 48 (12), pp. 1165-1169.
Ross P., et al., "High Level Multiplex Genotyping by MALDI-TOF Mass Spectrometry," Nature Biotechnology, 1998, vol. 16 (13), pp. 1347-1351.
Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.
Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.
Rota P.A., et al., "Sequencing of a cDNA Clone of the Nucleoprotein Gene of Influenza B/Ann Arbor/1/86," Nucleic Acids Research, 1989, vol. 17 (9), pp. 3595.
Ruan Y., et al., "Comparative Full-Length Genome Sequence Analysis of 14 SARS Coronavirus Isolates and Common Mutations Associated with the Putative Origins of Infection," The Lancet, 2003, vol. 361, pp. 1779-1785, 1832.
Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.
Rupf S., et al., "Quantitative Determination of *Streptococcus mutans* by using Competitive Polymerasechain Reaction," European Journal of Oral Sciences, 1999, vol. 107 (2), pp. 75-81.
Rupnik M., et al., "A Novel Toxinotyping Scheme and Correlation of Toxinotypes with Serogroups of Clostridium Difficile Isolates," Journal of Clinical Microbiology, 1998, vol. 36 (8), pp. 2240-2247.
Russell K.L., et al., "Transmission Dynamics and Prospective Environmental Sampling of Adenovirus in a Military Recruit Setting," Journal of Infectious Diseases, 2006, vol. 194 (7), pp. 877-885.
Ruttler M.E., et al., "Evaluation of Multiplex PCR Method to Detect Enteroaggregative *Escherichia coli*," Biocell, 2006, vol. 30 (2), pp. 301-308.
Sabat A., et al., "Comparison of PCR-Based Methods for Typing *Staphylococcus aureus* Isolates," Journal of Clinical Microbiology, 2006, vol. 44 (10), pp. 3804-3807.
Sackesen C., et al., "Use of Polymerase Chain Reaction for Detection of Adenovirus in Children Withor Without Wheezing," Turkish Journal of Pediatrics, 2005, vol. 47 (3), pp. 227-231.
Sakai H., et al., "Simultaneous Detection of *Staphylococcus aureus* and Coagulase-Negative Staphylococci in Positive Blood Cultures by Real-Time PCR with Two Fluorescence Resonance Energy Transfer Probe Sets," Journal of Clinical Microbiology, 2004, vol. 42 (12), pp. 5739-5744.
Sala M., et al., "Ambiguous Base Pairing of the Purine Analogue 1-(2-Deoxy-B-D-Ribofuranosyl)-Imidazole-4-Carboxamide During PCR," Nucleic Acids Research, 1996, vol. 24 (17), pp. 3302-3306.
Sallstrom B., et al., "Genome Reduction in the Alpha-Proteobacteria," Current Opinion in Microbiology, 2005, vol. 8 (5), pp. 579-585.
Sambrook J., et al., "Molecular Cloning—A Laboratory Manual," 1989, Cold Spring Harbor Laboratory Press, Table of Contents.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sanchez A., et al., "Detection and Molecular Characterization of Ebola Viruses Causing Disease in Human and Nonhuman Primates," Journal of Infectious Diseases, 1999, vol. 179 (1), pp. S164-S169.
Sanchez J.L., et al., "Epidemic of Adenovirus-Induced Respiratory Illness Among US Military Recruits: Epidemiologic and Immunologic Risk Factors in Healthy, Young adults," Journal of Medical Virology, 2001, vol. 65 (4), pp. 710-718.
Sanchez-Seco M.P., et al., "A Generic Nested-RT-PCR followed by Sequencing for Detection and Identification of Members of the Alphavirus Genus," Journal of Virological Methods, 2001, vol. 95 (1-2), pp. 153-161.
Santos S.R., et al., "Identification and Phylogenetic Sorting of Bacterial Lineages with Universally Conserved Genes and Proteins," Environmental Microbiology, 2004, vol. 6 (7), pp. 754-759.
Sarantis H., et al., "Comprehensive Detection and Serotyping of Human Adenoviruses by PCR and Sequencing," Journal of Clinical Microbiology, 2004, vol. 42 (9), pp. 3963-3969.
Sauer S., et al., "A Novel Procedure for Efficient Genotyping of Single Nucleotide Polymorphisms," Nucleic Acids Research, 2000, vol. 28 (5), pp. E13.1-E13.8.
Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.
Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.
Scheffner M., et al., "The E6 Oncoprotein Encoded by Human Papillomavirus Types 16 and 18 Promotes the Degradation of p53," Cell, 1990, vol. 63 (6), pp. 1129-1136.
Schena M., et al., "Genome Analysis with Gene Expression Microarrays," Bioessays, 1996, vol. 18 (5), pp. 427-431.
Scheuermann R.H., et al., "Polymerase Chain-Reaction-Based mRNA Quantification Using an Internal Standard: Analysis of Oncogene Expression," Methods in Enzymology, 1993, vol. 218, pp. 446-473.
Schlecht N.F., et al., "Viral Load as a Predictor of the Risk of Cervical Intraepithelial Neoplasia," British Journal of Cancer, 2003, vol. 103 (4), pp. 519-524.
Schmidt T.M., et al., "Analysis of a Marine Pikoplankton Community by 16s rRNA Gene Cloning and Sequencing," Journal of Bacteriology, 1991, vol. 173 (14), pp. 4371-4378.
Schmitz F.J., et al., "Development of a Multiplex-PCR for Direct Detection of the Genes for Enterotoxin B and C, and Toxic Shock Syndrome Toxin-1 in *Staphylococcus aureus* Isolates," Journal of Medical Microbiology, 1998, vol. 47 (4), pp. 335-340.
Schmitz F.J., et al., "Development of Resistance to Ciprofloxacin, Rifampin, and Mupirocin in Methicillin-Susceptible and -Resistant *Staphylococcus aureus* Isolates," Antimicrobial Agents and Chemotherapy, 2000, vol. 44 (11), pp. 3229-3231.
Schmitz F.J., et al., "Specific Information Concerning Taxonomy, Pathogenicity and Methicillin Esistance of *Staphylococci* Obtained by a Multiplex PCR," Journal of Medical Microbiology, 1997, vol. 46 (9), pp. 773-778.
Schram K.H., et al., "Mass Spectrometry of Nucleic Acid Components," Methods of Biochemical Analysis, 1990 vol. 34, pp. 203-280.

(56) References Cited

OTHER PUBLICATIONS

Schultz J.C., et al., "Polymerise Chain Reaction Products Analyzed by Charge Detection Mass Spectrometry," Rapid Communications in Mass Spectrometry, 1999, vol. 13 (1), pp. 15-20.

Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.

Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.

Sciacchitano C.J., "Analysis of Polymerase Chain Reaction-Amplified DNA Fragments of Clostridium Botulinum Type E Neurotoxin Gene by High Performance Capillary Electrophoresis," Journal of Liquid Chromatography & Related Technologies, 1996, vol. 19 (13), pp. 2165-2178.

Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid Identification of All Known Retroviral Reverse Transcriptase Sequences with a Novel Versatile Detection Assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive Detection of Ross River Virus—A One-Tube Nested RT-PCR," Journal of Virological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of Coxiella Burnetii," Infection and Immunity, 1999, vol. 67 (11), pp. 6026-6033.
Shadan F.F., et al., "N-Butyrate, A Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of Bacilus Subtilis Sub-Groups," Journal of Microbiological Methods, 2002, vol. 50 (2), pp. 215-223.
Shaver Y.J., et al., "Variation in 16s-23s rRNA Intergenic Spacer Regions Among Bacilus Subtilis 168 Isolates," Molecular Microbiology, 2001, vol. 42 (1), pp. 101-109.
Shimaoka M., et al., "Detection of the Gene for Toxic Shock Syndrome Toxin 1 in Siaphylococcusaureus by Enzyme-Labelled Olibonucleotideprobes," Journal of Medical Microbiology, 1996, vol. 44 (3), pp. 215-218.
Shimaoka M., et al., "Development of Enzyme-Labeled Oligonucleotide Probe for Detection of MecA Gene in Methicillin-Resistant *Staphylococcus aureus*," Journal of Clinical Microbiology, 1994, vol. 32 (8), pp. 1866-1869.
Shrestha N.K., et al., "Rapid Identification of *Staphylococcus aureus* and the MecA Gene from BacT/ALERT Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a New 3-h Hybridization Method for Detecting the MecA Gene in *Staphylococcus aureus* and Comparison with Existing Genotypic and Phenotypic Susceptibility Testing Methods," Journal of Antimicrobial Chemotherapy, 1999, vol. 43 (4), pp. 467-475.
Smirnov I.P., et al., "Application of DNA-Binding Polymers for Preparation of DNA for Analysis by Matrix-Assisted Laser Desorption/Ionization Mass Spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Snijder E.J., et al., "The Molecular Biology of Arteriviruses," The Journal of General Virology, 1998, vol. 79 (Pt 5), pp. 961-979.
Song F., et al., "Identification of cry11-type Genes from Bacilus Thuringiensis Strains and Characterization of a Novel Cry11-Type Gene," Applied and Environmental Microbiology, 2003, vol. 69, pp. 5207-5211.
Spackman E., et al., "Development of a Real-Time Reverse Transcriptase PCR Assay for Type A Influenzavirus and the Avian H5 and H7 Hemagglutinin Subtypes," Journal of Clinical Microbiology, 2002, vol. 40 (9), pp. 3256-3260.
Specialty Enzymes [online], [retrieved on Jan. 5, 2010]. Retrived from the Internet:< URL: Sigma Aldrich—sigmaaldrich.com/Area_of Interest/Life_Science/Molecular_Biology/PCR/Specialty_Enzymes.html.
Spiess L., et al., "Trehalose is a Potent PCR Enhancer: Lowering of DNA Melting Temperature and Thermal Stabilization of Taq Polymerase by the Disaccharide Trehalose," Clinical Chemistry, 2004, vol. 50 (7), pp. 1256-1259.
Srinivasan J.R., et al., "Matrix-Assisted Laser Desorption/Ionization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6). pp. 1044-1046.
Stephensen C.B., et al., "Phylogenetic Analysis of a Highly Conserved Region of the Poymerase Gene from 11 Coronaviruses and Development of a Consensus Poymerase Chain Reaction Assay," Virus Research, 1999, vol. 60 (2), pp. 181-189.
Stone B., et al., "Rapid Detection and Simultaneous Subtype Differentiation of Influenza A Viruses by Real Time PCR," Journal of Virological Methods, 2004, vol. 117 (2), pp. 103-112.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Stratagene Catalog, Gene Characterization Kits, 1988, pp. 39.
Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.
Studdert M.J., et al., "Polymerase Chain Reaction Tests for the Identification of Ross River, Kunjinand Murray Valley Encephalitis Virus Infections in Horses," Australian Veterinary Journal, 2003, vol. 81 (1-2), pp. 76-80.
Stuhlmeier R., et al., "Fast, Simultaneous, and Sensitive Detection of Staphylococci," Journal of Clinical Pathology, 2003, vol. 56 (10), pp. 782-785.
Sumner J.W., et al., "PCR Amplification and Comparison of Nucleotide Sequences from the groESL Heat Shock Operon of *Ehrlichia* Species," Journal of Critical Microbiology, 1997, vol. 35 (8), pp. 2087-2092.
Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.
Supplementary European Search Report for Application No. 04775904.8, dated Jul. 7, 2008, 8 pages.
Supplementary European Search Report for Application No. EP03796752.8, dated Aug. 7, 2007, 3 pages.
Supplementary European Search Report for Application No. EP03810055.8, dated Jun. 8, 2007, 4 pages.
Supplementary European Search Report for Application No. EP03814656, dated Oct. 16, 2007, 2 pages.
Supplementary European Search Report for Application No. EP04752257.8, dated Feb. 15, 2006, 2 pages.

(56) References Cited

OTHER PUBLICATIONS

Supplementary European Search Report for Application No. EP05753037, dated Aug. 21, 2009, 2 pages.
Supplementary Partial European Search Report for Application No. EP02709785.6, dated Sep. 1, 2005, 5 pages.
Supplementary Partial European Search Report for Application No. EP05751872.2, dated Jan. 28, 2008, 8 pages.
Supplementary Partial European Search Report for Application No. EP 05856582.1, dated Oct. 27, 2008, 10 pages.
Swaminathan B., et al., "PulseNet: The Molecular Subtyping Network for Foodborne Bacterial Disease Surveillance, United States," Emerging Infectious Diseases, 2001, vol. 7 (3), pp. 382-389.
Swanborg R.H., et al., "Human Herpesvirus 6 and Chlamydia Pneumoniae as Etiologic Agents in Multiplesclerosis—a Critical Review," Microbes and Infection / Institut Pasteur, 2002, vol. 4 (13), pp. 1327-1333.
Swenson J.M., et al., "Performance of Eight Methods, Including Two New Rapid Methods, for Detection of Oxacillin Resistance in a Challenge Set of *Staphylococcus aureus* Organisms," Journal of Clinical Microbiology, 2001, vol. 39 (10), pp. 3785-3788.
Takagaki Y., et al., "Four Factors are Required for 3"-End Cleavage of Pre-mRNAs," Genes and Development, 1989, vol. 3 (11), pp. 1711-1724.
Takahashi H., et al., "Characterization of gryA, gryB, grIA and grIB Mutations in Fluoroquinolone-Resistant Clinical Isolates of *Staphylococcus aureus*," The Journal of Antimicrobial Chemotherapy, 1998, vol. 41 (1), pp. 49-57.
Takahata M., et al., "Mutations in the GyrA and Gr1A Genes of Quinolone-Resistant Clinical Isolates of Methicillin-Resistant *Staphylococcus aureus*," The Journal of Antimicrobial Chemotherapy, 1996, vol. 38 (3), pp. 543-546.
Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.
Talaat A.M., et al., "Genome-Directed Primers for Selective Labeling of Bacterial Transcripts for DNA Microarray Analysis," Nature Biotechnology, 2000, vol. 17, pp. 679-682.
Tan T.Y., "Use of Molecular Techniques for the Detection of Antibiotic Resistance in Bacteria," Expert Review of Molecular Diagnostics, 2003, vol. 3 (1), pp. 93-103.
Tanabe F., et al., "The Properties and Mec A Gene of the Methicillin-Resistant *Staphylococcus aureus* Isolated in Fukushima Medical College Hospital," Fukushima Journal of Medical Science, 1993, vol. 39 (1), pp. 35-42.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., Double-Stranded DNA Analysis by Matrix Assisted Laser Desorption/Ionization, 42nd ASMS Conference on Mass Spectrometry, 1994.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
Tang K., et al., Matrix-Assisted Laser Desorption/Ionization Mass Spectrometry of Oligonucleotides, Dissertation submitted to the Faculty of Vanderbilt University, 1994.
Tarassishin L., et al., "Adenovirus Core Protein VII Displays a Linear Epitope Conserved in a Range of Human Adenoviruses," Journal of General Virology, 1999, vol. 80 (Pt 1), pp. 47-50.
Tarassishin L., et al., "An Epitope on the Adenovirus Fibre Tail is Common to all Human Subgroups," Archives of Virology, 2000, vol. 145 (4), pp. 805-811.
Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Taubenberger J.K., et al., "Characterization of the 1918 Influenza Virus Polymerase Genes," Nature, 2005, vol. 437 (7060), pp. 889-893.
Taylor L.H., et al., "Risk Factors for Human Disease Emergence," Philosophical Transactions of the Royal Society of London Series B, Biological Sciences, 2001, vol. 356 (1411), pp. 983-989.
Tenover F.C., et al., "Characterization of a Strain of Community-Associated Methicillin-Resistant*Slaphylococcus aureus* Widely Disseminated in the United States," Journal of Clinical Microbiology, 2006, vol. 44 (1), pp. 108-118.
Teramura T., et al., "Quantitative Detection of Serum Adenovirus in a Transplant Recipient," Lancet, 2002, vol. 359 (9321), pp. 1945.
Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.
Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.
Thompson W.W., et al., "Influenza-Associated Hospitalizations in the United States," The Journal of the American Medical Association, 2004, vol. 292 (11), pp. 1333-1340.
Tokue Y., et al., "Comparison of a Polymerase Chain Reaction Assay and a Conventional Microbiologic Method for Detection of Methicillin-Resistant *Slaphylococcus aureus*," Antimicrobial Agents and Chemotherapy, 1992, vol. 36 (1), pp. 6-9.
Tong J., et al., "Ligation Reaction Specificities of an NAD+-Dependent DNA Ligase from the Hyperthermophile Aquifex Aeolicus," Nucleic Acids Research, 2000, vol. 28 (6), pp. 1447-1454.
Top F.H Jr., "Control of Adenovirus Acute Respiratory Disease in U.S. Army Trainees," The Yale Journal of Biology and Medicine, 1975, vol. 48 (3), pp. 185-195.
Torroni A., et al., "Classification of European mtDNAs from an Analysis of Three European Populations," Genetics, 1996, vol. 144 (4), pp. 1835-1850.
Towner K.J., et al., "Development and Evaluation of a PCR-Based Immunoassay for the Rapid Detection of Methicillin-Resistant *Staphylococcus aureus*," Journal of Medical Microbiology, 1998, vol. 47 (7), pp. 607-613.
Tristan A., et al., "Virulence Determinants in Community and Hospital Meticillin-Resistant *Staphylococcus aureus*," The Journal of Hospital Infection, 2007, vol. 65 (2), pp. 105-109.
Tsuneyoshi T., et al., "Mass Spectrometric Gene Diagnosis of One-Base Substitution from Polymerase Chain Reaction Amplified Human DNA," Rapid Communications in Mass Spectomerty, 1997, vol. 11 (7), pp. 719-722.
Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.
Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.
Udo E.E., et al., "Genetic Analysis of Methicillin-Resistant *Staphylococcus aureus* Expressing High- and Low-Level Mupirocin Resistance," Journal of Medical Microbiology, 2001, vol. 50 (10), pp. 909-915.
Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.
Unal S., et al., "Detection of Methicillin-Resistant Staphylococci by Using the Polymerase Chain Reaction," Journal of Clinical Microbiology, 1992, vol. 30 (7), pp. 1685-1691.
Upton A., et al., "Mupirocin and *Staphylococcus aureus*: A Recent Paradigm of Emerging Antibiotic Resistance," The Journal of Antimicrobial Chemotherapy, 2003, vol. 51 (3), pp. 613-617.
User Enzyme [online], [retrieved on Jan. 5, 2010]. Retrived from the Internet:< URL: www.neb.com/nebecomm/products/productM5505.asp.

(56) References Cited

OTHER PUBLICATIONS

Vabret A., et al., "Development of a PCR- and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.

Van Aerschot A., et al., "In Search of Acyclic Analogues as Universal Nucleosides in Degenerate Probes," Nucleosides and Nucleotides, 1995, vol. 14 (3-5), pp. 1053-1056.

Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.

Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.

Van Den Berg R.J., et al., "Rapid Diagnosis of Toxinogenic Clostridium Difficile in Faecal Samples with Internally Controlled Real-Time PCR," Clinical Microbiology and Infection : The Official Publication of the European Society of Clinical Microbiology and Infectious Diseases, 2006, vol. 12 (2), pp. 184-186.

Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.

Van Der Zee H., et al., "Rapid and Alternative Screening Methods for Microbiological Analysis," Journal of AOAC International, 1997, vol. 80 (4), pp. 934-940.

Van Dinten L.C., et al., "Proteolytic Processing of the Open Reading Frame lb-EncodedPart of Arterivirus Replicase is Mediated by nsp4 Serine Protease and is Essential for Virus Replication," Journal of Virology, 1999, vol. 73 (3), pp. 2027-2037.

Van Elden L.J., et al., "Clinical Diagnosis of Influenza Virus Infection: Evaluation of Diagnostic Tools in General Practice," The British Journal of General Practice, 2001, vol. 51 (469), pp. 630-634.

Van Elden L.J., et al., "Simultaneous Detection of Influenza Viruses A and B Using Real-Time Quantitative PCR," Journal of Clinical Microbiology, 2001, vol. 39 (1), pp. 196-200.

Van Ert M.N., et al., "Mass Spectrometry Provides Accurate Characterization of Two Genetic Marker Types in Bacillus Anthracis," Bio Techniques, 2004, vol. 37 (4), pp. 642-651.

Van Leeuwen W.B., et al., "Multilocus Sequence Typing of *Staphylococcus aureus* with DNA Array Technology," Journal of Clinical Microbiology, 2003, vol. 41 (7), pp. 3323-3326.

Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.

Vanchiere J.A., et al., "Detection of BK Virus and Simian Virus 40 in the Urine of Healthy Children," Journal of Medical Virology, 2005, vol. 75 (3), pp. 447-454.

Vanderhallen H., et al. "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.

Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.

Vannuffel P., et al., "Specific Detection of Methicillin-Resistant *Staphylococcus* Species by Multiplex PCR," Journal of Clinical Microbiology, 1995, vol. 33 (11), pp. 2864-2867.

Verma S., et al., "Modified Oligonucleotides: Synthesis and Strategy for Users," Annual Review of Biochemistry, 1998, vol. 67, pp. 99-134.

Vidal M., et al., "Single Multiplex PCR Assay to Identify Simultaneously the Six Categories of Diarrheagenic *Escherichia coli* Associated with Enteric Infections," Journal of Clinical Microbiology, 2005, vol. 43 (10), pp. 5362-5365.

Videla C., et al., "Genomic Analysis of Adenovirus Isolated from Argentinian Children with Acute Lower Respiratory Infections," Journal of Clinical Virology, 1999, vol. 14 (1), pp. 67-71.

Vilchez R.A. et al., "Detection of Polyomavirus Simian Virus 40 Tumor Antigen DNA in AIDS-Related Systemic Non-Hodgkin Lymphoma," Journal of Acquired Immune Deficiency Syndromes, 2002, vol. 29 (2), pp. 109-116.

Voelter C., et al., "Screening Human Tumor Samples with a Broad-Spectrum Polymerase Chain Reaction Method for the Detection of Polyomaviruses," Virology, 1997, vol. 237 (2), pp. 389-396.

Volokhov D., et al., "Microarray Analysis of Erythromycin Resistance Determinants," Journal of Applied Microbiology, 2003, vol. 95 (4), pp. 787-798.

Von Eiff C., et al., "Pathogenesis of Infections Due to Coagulase-Negative Staphylococci," The Lancet Infectious Diseases, 2002, vol. 2 (11), pp. 677-685.

Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.

Walker E.S., et al., "A Decline in Mupirocin Resistance in Methicillin-Resistant *Staphylococcus aureus* Accompanied Administrative Control of Prescriptions," Journal of Clinical Microbiology, 2004, vol. 42 (6), pp. 2792-2795.

Wallace S.S., et al., "The Enigma of Endonuclease VIII," DNA Repair, 2003, vol. 2 (5), pp. 441-453.

Wallet F., et al., "Choice of a Routine Method for Detecting Methicillin-Resistance in Staphylococci," The Journal of Antimicrobial Chemotherapy, 1996, vol. 37 (5), pp. 901-909.

Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.

Wang G., et al., "Targeted Mutagenesis in Mammalian Cells Mediated by Intracellular Triple Helix Formation," Molecular and Cellular Biology, 1995, vol. 15 (3), pp. 1759-1768.

Ward C.L., et al., "Design and Performance Testing of Quantitative Real Time PCR Assays for Influenza A and B Viral Load Measurement," Journal of Clinical Virology, 2004, vol. 29 (3), pp. 179-188.

Watanabe K., et al., "ICB Database: The gyrB Database for Identification and Classification of Bacteria," Nucleic Acids Research, 2001, vol. 29 (1), pp. 344-345.

Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.

Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.

Wertheim H.F., et al., "Effect of Mupirocin Treatment on Nasal, Pharyngeal, and Perineal Carriage of *Staphylococcus aureus* in Healthy Adults," Antimicrobial Agents and Chemotherapy, 2005, vol. 49 (4), pp. 1465-1467.

Westermann P., et al., "Inhibition of Expression of SV40 Virus Large T-Antigen by Antisense Oligodeoxyribonucleotides," Biomedica Biochimica Acta, 1989, vol. 1, pp. 85-93.

Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.

Wichelhaus T.A., et al., "Rapid Detection of Epidemic Strains of Methicillin-Resistant *Staphylococcus aureus*," Journal of Clinical Microbiology, 1999, vol. 37 (3), pp. 690-693.

Wickham T.J., "Targeting Adenovirus," Gene Therapy, 2000, vol. 7 (2), pp. 110-114.

Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.

(56) References Cited

OTHER PUBLICATIONS

Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.

Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.

Wolter A., et al., "Negative Ion FAB Mass Spectrometric Analysis of Non-Charged Key Intermediates in Oligonucleotide Synthesis: Rapid Identification of Partially Protected Dinucleoside Monophosphates," Biomedical and Environmental Mass Spectrometry, 1987, vol. 14, pp. 111-116.

Woo T.H., et al., "Identification of Leptospira Inadai by Continuous Monitoring of Fluorescence during Rapid Cycle PCR," Systematic and Applied Microbiology, 1998, vol. 21 (1), pp. 89-96.

Wood S.R., et al., "Rapid Detection and Serotyping of Adenovirus by Direct Immunofluorescence," Journal of Medical Virology, 1997, vol. 51 (3), pp. 198-201.

Wright K.E., et al., "Typing and Subtyping of Influenza Viruses in Clinical Samples by PCR," Journal of Clinical Microbiology, 1995, vol. 33 (5), pp. 1180-1184.

Written Opinion for Application No. PCT/US2004/33742, dated May 15, 2006, 5 pages.

Wu S., et al., "Genetic Organization of the mecA Region in Methicillin-Susceptible and Methicillin-Resistant Strains of *Staphylococcus sciuri*," The Journal of Bacteriology, 1998, vol. 180 (2), pp. 236-242.

Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.

Wunschel D., et al., "Discrimination Among the B. Cereus Group, in Comparison to B. Subtilis, by Structural Carbohydrate Profiles and Ribosomal RNA Spacer Region PCR," Systematic and Applied Microbiology, 1994, vol. 17, pp. 625-635.

Wunschel D.S., et al., "Analysis of Double-Stranded Polymerase Chain Reaction Products from the Bacilus Cereus Group by Electrospray Lonization Fourier Transform Lon Cyclotron Resonance Mass Spectrometry," Rapid Communications in Mass Spectrometry, 1996, vol. 10 (1), pp. 29-35.

Wunschel D.S., et al., "Heterogeneity in Bacillus Cereus PCR Products Detected by ESI-FTICR Mass Spectrometry," Analytical Chemistry, 1998, vol. 70 (6), pp. 1203-1207.

Wunschel D.S., et al., "Mass spectrometric characterization of DNA for molecular biological applications: advances using MALDI and ESI," Advances in Mass Spectrometry, 1998, vol. 14, Elsevier, pp. 377-406.

Xu L., et al., "Electrophore Mass Tag Dideoxy DNA Sequencing," Analytical Chemistry, 1997, vol. 69 (17), pp. 3595-3602.

Xu W., et al., "Species-Specific Identification of Human Adenoviruses by a Multiplex PCR Assay," Journal of Clinical Microbiology, 2000, vol. 38 (11), pp. 4114-4120.

Xu W., et al., "Type-Specific Identification of Human Adenovirus, 3, 7, and 21 by a Multiplex PCR Assay," Journal of Medical Virology, 2001, vol. 64 (4), pp. 537-542.

Xu X., et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.

Yao Z.P., et al., "Mass Spectrometry Based Proteolytic Mapping for Rapid Virus Identification," Analytical Chemistry, 2002, vol. 74 (11), pp. 2529-2534.

Yasui T., et al., "A Specific Oligonucleotide Primer for the Rapid Detection of Lactobacillus Lindneri by Polymerase Chain Reaction," Canadian Journal of Microbiology, 1997, vol. 43 (2), pp. 157-163.

Ye K., et al., "Three Distinct Promoters Direct Transcription of Different 5" Untranslated Regions of the Human Interleukin 1 Type 1 Receptor. A Possible Mechanism for Control of Translation," Cytokine, 1996, vol. 8 (6), pp. 421-429.

Yun H.J., et al., "Increased Antibacterial Activity of OW286, A Novel Fluoronaphthyridone Antibiotic, Against *Staphylococcus aureus* Strains with Defined Mutations in DNA Gyrase and Toposiomerase IV," International Journal of Antimicrobial Agents, 2005, vol. 25 (4), pp. 334-337.

Zeng Z.B., "Precision Mapping of Quantitative Trait Loci," Genetics, 1994, vol. 136 (4), pp. 1457-1468.

Zhang J., et al., "PowerBLAST: A New Network BLAST Application for Interactive or Automated Sequence Analysis and Annotation," Genome Research, 1997, vol. 7 (6), pp. 649-656.

Zhang K., et al., "New Quadriplex PCR Assay for Detection of Methicillin and Mupirocin Resistance and Simultaneous Discrimination of *Staphylococcus aureus* from Coagulase-Negative Staphylococci," Journal of Clinical Microbiology, 2004, vol. 42 (11), pp. 4947-4955.

Zhang W.D., et al., "Detection and Identification of Human Influenza Viruses by the Polymerase Chain Reaction," Journal of Virological Methods, 1991, vol. 33 (1-2), pp. 165-189.

Zhang Y.Q., et al., "Genome-Based Analysis of Virulence Genes in a Non-Biofilm-Forming *Staphylococcus epidemidis* Strain (ATCC 12228)," Molecular Microbiology, 2003, vol. 49 (6), pp. 1577-1593.

\* cited by examiner

METHODS FOR REPAIRING DEGRADED DNA

CROSS-REFERENCE TO RELATED APPLICATIONS

This application is a Divisional application of copending U.S. patent application Ser. No. 10/891,337, filed Jul. 14, 2004 which is hereby incorporated by reference in its entirety.

FIELD OF THE INVENTION

This invention relates generally to the field of amplification of DNA and provides methods and kits for repair of degraded DNA in order to improve DNA amplification processes.

BACKGROUND OF THE INVENTION

Successful DNA amplification relies on the integrity of the DNA template but aged samples or samples stored under sub-optimal conditions often results in failed amplification reactions.

DNA both in the living cells and isolated in vitro is subject to many chemical alterations (a fact often forgotten in the excitement of being able to do DNA sequencing on dried and/or frozen specimens). If the genetic information encoded in the DNA is to remain uncorrupted, any chemical changes must be corrected. The recent publication of the human genome has already revealed 130 genes whose products participate in DNA repair.

Agents that damage DNA include: ionizing radiation such as gamma rays and x-rays ultraviolet rays, especially the UV-C rays (~260 nm) that are absorbed strongly by DNA but also the longer-wavelength UV-B, highly-reactive oxygen radicals produced during normal cellular respiration as well as by other biochemical pathways, many hydrocarbons, including some found in cigarette smoke, some plant and microbial products and chemicals used in chemotherapy, especially chemotherapy of cancers All four of the bases in DNA (A, T, C, G) can be covalently modified at various positions. One of the most frequent is deamination, resulting for example, in a C being converted to a U. Mismatches of the normal bases because of a failure of proofreading during DNA replication. A common example is incorporation of the pyrimidine U (normally found only in RNA) instead of T.

Nicks in the DNA backbone can be limited to one of the two strands (a single-stranded break, SSB) or on both strands (a double-stranded break (DSB). Ionizing radiation is a frequent cause, but some chemicals produce breaks as well.

Covalent cross-linkages can be formed between bases on the same DNA strand ("intra-strand") or on the opposite strand ("inter-strand").

Various types of DNA damage can occur during improper storage, aging, freeze-thawing, or exposure to acid, heat or light. This will adversely affect the performance of the DNA as template in PCR because the damage will block the progression of the DNA polymerase.

Enzyme reagents for use in the modification and repair of degraded DNA are available commercially, for example from New England BioLabs (neb.com/nebecomm/products/category12.asp#16). However, only recently has attention been focused on combining such enzyme reagents for the purpose of repairing DNA and improving the DNA template integrity for subsequent amplification reactions. For example, Restorase™ (Sigma Aldrich) has been demonstrated to repair AP sites, but not other types of DNA damage such as backbone nicks.

There remains a need for combinations of enzymes to effect repair of the many different classes of DNA damage for subsequent amplification reactions, particularly since alternative amplification methods to PCR are gaining prominence. One particularly useful method is whole genome amplification by multiple displacement amplification (MDA). MDA has been developed for the whole genome amplification of human DNA samples. MDA relies on priming the genomic DNA with exonuclease resistant random primers and the use of a strand displacing DNA polymerase such as Φ29 DNA polymerase. Φ29 DNA polymerase is highly processive, strand displacing and has a very low error rate of 1 in $10^6$-$10^7$ nucleotides compared to an error rate of 3 in $10^4$ for native Taq polymerase and 1.6 in $10^6$ for Pfu polymerase. Due to the high processivity and strand displacing properties of Φ29 DNA polymerase the MDA reaction is performed under isothermal conditions at 30° C. The combination of a highly processive enzyme and random priming makes MDA amplification ideal approach for the amplification of DNA where there is currently insufficient material for use standard DNA typing technologies.

Other such alternatives to PCR amplification include isothermal helicase-dependent amplification, LATE-PCR assymmetric amplification, and single primer isothermal linear amplification.

Endonuclease VIII from *E. coli* acts as both an N-glycosylase and an AP-lyase. The N-glycosylase activity releases degraded pyrimidines from double-stranded DNA, generating an AP site. The AP-lyase activity cleaves 3' to the AP site leaving a 5' phosphate and a 3' phosphate. Degraded bases recognized and removed by Endonuclease VIII include urea, 5,6-dihydroxythymine, thymine glycol, 5-hydroxy-5-methylhydantoin, uracil glycol, 6-hydroxy-5,6-dihydrothymine and methyltartronylurea. While Endonuclease VIII is similar to Endonuclease III, Endonuclease VIII has β and δ lyase activity while Endonuclease III has β lyase activity (New England BioLabs—neb.com/nebecomm/products/productM0299.asp).

Fpg (formamidopyrimidine [fapy]-DNA glycosylase) (also known as 8-oxoguanine DNA glycosylase) acts both as an N-glycosylase and an AP-lyase. The N-glycosylase activity releases degraded purines from double stranded DNA, generating an apurinic (AP site). The AP-lyase activity cleaves both 3' and 5' to the AP site thereby removing the AP site and leaving a 1 base gap. Some of the degraded bases recognized and removed by Fpg include 7,8-dihydro-8-oxoguanine (8-oxoguanine), 8-oxoadenine, fapy-guanine, methyl-fapy-guanine, fapy-adenine, aflatoxin B1-fapy-guanine, 5-hydroxy-cytosine and 5-hydroxy-uracil (New England BioLabs—neb.com/nebecomm/products/productM0240.asp).

USER (Uracil-Specific Excision Reagent) enzyme generates a single nucleotide gap at the location of a uracil. USER Enzyme is a mixture of Uracil DNA glycosylase (UDG) and the DNA glycosylase-lyase Endonuclease VIII. UDG catalyses the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released (New England BioLabs—neb.com/nebecomm/products/productM5505.asp).

Endonuclease IV can act on a variety of oxidative damage in DNA. The enzyme is apurinic/apyrimidinic (AP) endonuclease that will hydrolyze intact AP sites in DNA. AP sites are cleaved at the first phosphodiester bond that is 5' to the lesion leaving a hydroxyl group at the 3' terminus and a deoxyribose 5'-phosphate at the 5' terminus. The enzyme also has a 3'-diesterase activity and can release phosphoglycoaldehyde, intact deoxyribose 5-phosphate and phosphate from the 3' end of DNA (New England BioLabs—neb.com/nebecomm/products/productM0304.asp).

DNA Polymerase I, Large (Klenow) Fragment is a proteolytic product of *E. coli* DNA Polymerase I which retains polymerization and 3'→5' exonuclease activity, but has lost 5'→3' exonuclease activity. Klenow retains the polymerization fidelity of the holoenzyme without degrading 5' termini. This enzyme is used in applications such as filling-in of 5' overhangs to form blunt ends, removal of 3' overhangs to form blunt ends, and second strand cDNA synthesis (New England BioLabs-neb.com/nebecomm/products/productM0210.asp).

T4 polynucleotide kinase catalyzes the transfer and exchange of a phosphate group from the γ position of ATP to the 5'-hydroxyl terminus of polynucleotides (double- and single-stranded DNA and RNA) and nucleoside 3'-monophosphates and also catalyzes the removal of 3'-phosphoryl groups from 3'-phosphoryl polynucleotides, deoxynucleoside 3'-monophosphates and deoxynucleoside 3'-diphosphates (New England BioLabs—neb.com/nebecomm/products/productM0201.asp).

T4 DNA ligase catalyzes the formation of a phosphodiester bond between juxtaposed 5' phosphate and 3' hydroxyl termini in duplex DNA or RNA. This enzyme will join blunt end and cohesive end termini as well as repair single stranded nicks in duplex DNA, RNA or DNA/RNA hybrids (New England BioLabs—neb.com/nebecomm/products/productM0202.asp).

The present invention satisfies the need for providing, inter alio, combinations of DNA repair enzymes that are useful for restoring the integrity of degraded DNA templates so that effective and efficient amplification can be obtained and subsequent analyses carried out. Examples of such subsequent analyses include, but are not limited to, methods for identification of bacterial and viral bioagents for biodefense, diagnostics and forensics investigations which are disclosed and claimed in U.S. patent application Ser. Nos. 09/798,007, 10/660,122, 10/728,486, 10/405,756, 10/660,998 and 10/807,019, each of which is commonly owned and incorporated herein by reference in its entirety.

SUMMARY OF THE INVENTION

The present invention provides methods for repairing degraded DNA in vitro comprising contacting the degraded DNA with an enzyme combination. The enzyme combination comprises endonuclease activity, DNA N-glycosylase activity, AP lyase activity, polymerase activity, 3'-diesterase activity, polynucleotide kinase activity, and DNA ligase activity. In some embodiments, the degraded DNA comprises a covalent modification such as, for example, a deamination, or an intra-strand or inter-strand cross linkage. In some embodiments, the degraded DNA comprises a nick, which can be either a single-stranded break or a double-stranded break. In some embodiments, the degraded DNA comprises an abasic site. In some embodiments, the endonuclease activity is provided by endonuclease VIII, endonuclease IV, or is provided by a combination of endonuclease IV and endonuclease VIII. In some embodiments, the DNA N-glycosylase activity is provided by endonuclease VIII, uracil DNA glycosylase, or 8-oxoguanine DNA glycosylase. In some embodiments, the AP lyase activity is provided by endonuclease VIII, or 8-oxoguanine DNA glycosylase. In some embodiments, the polymerase activity is provided by DNA Polymerase I, Large (Klenow) Fragment. In some embodiments, the 3'-diesterase activity is provided by endonuclease IV. In some embodiments, the polynucleotide kinase activity is provided by T4 polynucleotide kinase. In some embodiments, the DNA ligase activity is provided by T4 DNA ligase. In some embodiments, the degraded DNA comprises a degraded base such as, for example, urea, 5,6-dihydroxythymine, thymine glycol, 5-hydroxy-5-methylhydantoin, uracil glycol, 6-hydroxy-5, 6-dihydrothymine, methyltartronylurea, 7,8-dihydro-8-oxoguanine (8-oxoguanine), 8-oxoadenine, fapy-guanine, methyl-fapy-guanine, fapy-adenine, aflatoxin B1-fapy-guanine, 5-hydroxy-cytosine, or 5-hydroxy-uracil.

The present invention also provides methods for amplification of degraded DNA in vitro. The degraded DNA is contacted with an enzyme combination comprising endonuclease activity, DNA N-glycosylase activity, AP lyase activity, polymerase activity, 3'-diesterase activity, polynucleotide kinase activity, and DNA ligase activity to produce repaired DNA. The repaired DNA is purified from the enzyme combination. The repaired DNA is amplified by methods such as for example, polymerase chain reaction, helicase-dependent amplification, LATE-PCR assymmetric amplification, single primer isothermal linear amplification, or multiple displacement amplification. In some embodiments, the polymerase used to effect the multiple displacement amplification is irradiated with an effective amount of ultraviolet light to destroy contaminating DNA in the preparation of the polymerase. In some embodiments, the polymerase is Φ29 polymerase.

The present invention also provides kits comprising an endonuclease, a DNA N-glycosylase, an AP lyase, a DNA polymerase, a 3'-diesterase, a polynucleotide kinase, and a DNA ligase. In some embodiments, the kits also comprise a mixture of random primers, a mixture of deoxynucleotide triphosphates, and/or a highly processive strand displacing polymerase.

DESCRIPTION OF EMBODIMENTS

Figure 1:
FIG. 1 indicates that irradiated human mitochondrial DNA does not amplify in the whole genome amplification reaction. Lane (a): positive control—1 ng of non-irradiated mitochondrial DNA); Lane (b): size ladder; Lane (c): 10 ng of irradiated DNA treated with the heat denaturation step described in Example 2; Lane (d): 10 ng irradiated DNA without the heat denaturation step; Lanes (e and f): negative controls amplified with and without the heat denaturation step.

The present invention is directed to, inter alia, methods for repairing degraded DNA in vitro comprising contacting the degraded DNA with an enzyme combination. The enzyme combination comprises endonuclease activity, DNA N-glycosylase activity, AP lyase activity, polymerase activity, 3'-diesterase activity, polynucleotide kinase activity, and DNA ligase activity, or any combination thereof. The degraded DNA can be contacted with any combination or all of the foregoing enzymes in a single cocktail or a series of cocktails, or can be contacted sequentially in any order.

As defined herein, the term "in vitro" refers to DNA isolated from a cell or tissue.

As defined herein, the term "AP site" refers to an apurinic or apyrimidinic site (i.e., a nucleobase within a segment of DNA whose purine or pyrimidine base has been removed).

In some embodiments, the endonuclease activity is provided by one or more enzymes such as, for example, endonuclease VIII or endonuclease IV, or a combination thereof. Other suitable enzymes having endonuclease activity are known to those skilled in the art and can also be used in the methods described herein.

In some embodiments, the DNA N-glycosylase activity is provided by one or more enzymes such as, for example, endonuclease VIII, uracil DNA glycosylase, or 8-oxoguanine DNA glycosylase, or any combination thereof. Other suitable enzymes having DNA N-glycosylase activity are known to those skilled in the art and can also be used in the methods described herein.

In some embodiments, the AP lyase activity is provided by one or more enzymes such as, for example, endonuclease VIII or 8-oxoguanine DNA glycosylase, or a combination thereof. Other suitable enzymes having AP lyase activity are known to those skilled in the art and can also be used in the methods described herein.

In some embodiments, the polymerase activity is provided by one or more enzymes such as, for example, DNA Polymerase I, Large (Klenow) Fragment. Other suitable enzymes having polymerase activity are known to those skilled in the art and can also be used in the methods described herein.

In some embodiments, the 3'-diesterase activity is provided by one or more enzymes such as, for example, endonuclease IV. Other suitable enzymes having 3'-diesterase activity are known to those skilled in the art and can also be used in the methods described herein.

In some embodiments, the polynucleotide kinase activity is provided by one or more enzymes such as, for example, T4 polynucleotide kinase. Other suitable enzymes having polynucleotide kinase activity are known to those skilled in the art and can also be used in the methods described herein.

In some embodiments, the DNA ligase activity is provided by one or more enzymes such as, for example, T4 DNA ligase. Other suitable enzymes having DNA ligase activity are known to those skilled in the art and can also be used in the methods described herein.

In some embodiments, the degraded DNA comprises a degraded base such as, for example, modified purine and pyrimidine bases including, but not limited to, urea, 5,6-dihydroxythymine, thymine glycol, 5-hydroxy-5-methylhydantoin, uracil glycol, 6-hydroxy-5,6-dihydrothymine, methyltartronylurea, 7,8-dihydro-8-oxoguanine (8-oxoguanine), 8-oxoadenine, fapy-guanine, methyl-fapy-guanine, fapy-adenine, aflatoxin B1-fapy-guanine, 5-hydroxy-cytosine, or 5-hydroxy-uracil.

In some embodiments, the degraded DNA comprises other classes of DNA damage including, but not limited to, a backbone nick, an abasic (apurinic or apyrimidinic) site, or an inter- or intra-strand cross linkage.

The present invention is also directed to methods for amplification of degraded DNA comprising repairing the degraded DNA by contacting the degraded DNA with an enzyme combination that contains endonuclease activity, DNA N-glycosylase activity, AP lyase activity, polymerase activity, 3'-diesterase activity, polynucleotide kinase activity, and DNA ligase activity. The repaired DNA is purified from the enzyme combination and the DNA is amplified by amplification methods including, but not limited to, PCR, multiple displacement amplification, rolling circle amplification, helicase-dependent amplification, LATE-PCR assymmetric amplification, and single primer isothermal linear amplification.

In some embodiments, the polymerase used to effect the multiple displacement amplification is irradiated with an effective amount of ultraviolet light to destroy contaminating DNA in the preparation of the polymerase used for multiple displacement amplification. In some embodiments, the polymerase is Φ29 polymerase.

The present invention is also directed to kits for repairing degraded DNA. In some embodiments, the kits include an enzyme combination that contains DNA N-glycosylase activity, AP lyase activity, DNA polymerase activity, a 3'-diesterase activity, polynucleotide kinase activity, and DNA ligase activity, or any combination thereof. In some embodiments, the kit comprises packaging material containing the components thereof.

The kit may also comprise a sufficient quantity of reagents for carrying out multiple displacement amplification reactions (whole genome amplification), including, for example, Φ29 polymerase, a mixture of random primers, nucleotide triphosphates, and/or a highly processive strand displacing polymerase, or any combination thereof. A kit may further include instructions pertinent for the particular embodiment of the kit, such instructions describing how to irradiate the polymerase to deactivate contaminating DNA. A kit may also comprise amplification reaction containers such as microcentrifuge tubes and the like.

The present invention also comprises compositions comprising any two or more of the following enzymes: DNA N-glycosylase activity, AP lyase activity, DNA polymerase activity, a 3'-diesterase activity, polynucleotide kinase activity, and DNA ligase activity, or any combination thereof. Representative examples of each of these enzymes are described above.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Figure 2:
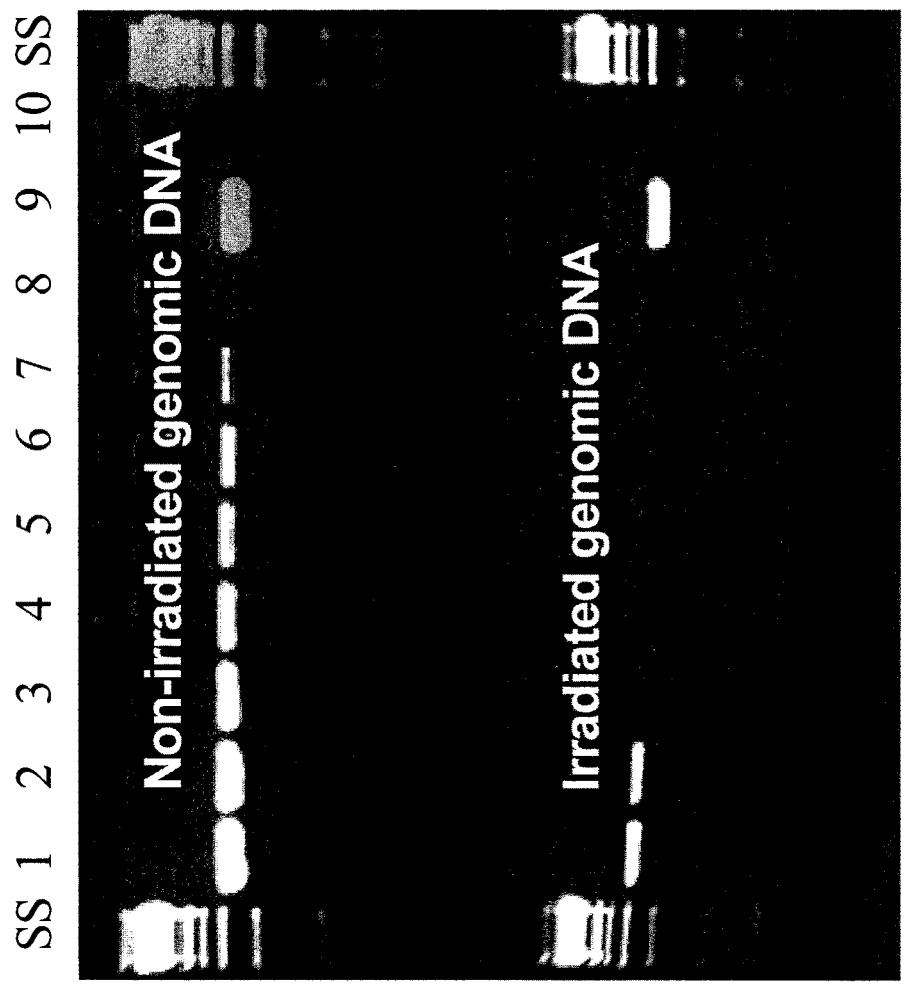
FIG. 2 indicates that irradiated DNA performs poorly in PCR reactions targeting the HV2 region of human mitochondrial DNA. Lanes 1-8 have 1 ng, 500 pg, 100, pg, 25 pg, 12 pg, 6 pg, 3 pg and 300 fg of irradiated mitochondrial DNA template added to the HV2 PCR reactions. Lane 9 is a positive control and lane 10 is a negative control.

Example 1: Repair of Irradiated Double-Stranded DNA Prior Use in Multiple Displacement Amplification Irradiation of DNA is used herein as a means to artificially damage DNA in order to investigate the capability of DNA repair enzyme mixtures to repair the damage. As shown in FIG. 1, human mitochondrial DNA exposed to 4 mega-rad of radiation (lanes c-f) is not amplifiable by whole genome amplification (WGA) effected by multiple displacement amplification (MDA), presumably due to the large frequency of nicks and degraded nucleotides. Likewise, the same radiation treatment results in poor PCR amplification of the HV2 region of human mitochondrial DNA relative to non-irradiated control DNA samples (FIG. 2). A significant difference in the amount of irradiated DNA needed in a PCR reaction in order to obtain a detectable PCR product was observed. This observation was fortuitous because it enabled a quick test of DNA repair formulations and conditions to quickly assess their effects on improving the performance of the irradiated DNA in PCR instead of in WGA.

For repair of irradiated DNA, the following protocol was found to be effective: a stock enzyme combination solution (herein designated RC13 enzyme mix) was prepared as shown in Table 1 and stored at −20° C. RC13 is repair cocktail formulation number 13 and its formulation is the result of over 100 different test reaction conditions and formulations. The repair assay improved the performance of irradiated DNA in both PCR and WGA reactions. The RC13 enzyme mixture contains four different enzymes that are involved with the excision of degraded nucleotides from DNA. The mixture also contains a polynucleotide kinase, a polymerase to extend and fill in gaps and a ligase to repair nicks and to concatamerize the DNA fragments. One hurdle was the identification of inhibitors from the repair cocktail that block the WGA reaction. It was found that the enzymes themselves were the source of the inhibition and that efficient amplification of the repaired DNA requires a phenol/chloroform purification step.

TABLE 1

Preparation of RC13 Enzyme Mix

| Enzyme/Reagent | Vendor | Cat# | Units/ml | Amount (µl) | Final Units/µl |
|---|---|---|---|---|---|
| Endonuclease VIII | NEB | M0299S | 10000 | 2 | 0.38 |
| FPG | NEB | M0240S | 8000 | 2 | 0.30 |
| USER Enzyme | NEB | M5505S | 1000 | 2 | 0.04 |
| Endonuclease IV | Epicentre | E70100 | 2000 | 2 | 0.08 |
| Klenow fragment | NEB | M0212S | 5000 | 2 | 0.19 |
| T4 Polynucleotide Kinase | NEB | M0201S | 10000 | 1 | 0.38 |
| T4 DNA ligase High Conc. | NEB | | 2,000,000 | 25 | 657 |
| 50% Glycerol | — | — | — | 40 | |

RC13 buffer composed of 250 mM TRIS-HCl, pH 7.6, 50 mM $MgCl_2$, 5 mM ATP and 5 mM dithiothreitol was used for the DNA repair reaction with the RC13 enzyme combination as follows: water was added to a DNA solution to a volume of 15 µl or 25 µl, to which was added 4 µl RC13 buffer and 1.5 µl RC13 enzyme mix for the 15 µl reaction or 6 µl RC13 buffer and 1.5 µl RC13 enzyme mix for the 25 µl reaction. The reaction mixture was then incubated in a thermocycler at 37° C. for 2 hours then at 16° C. for 12 hours. The reaction was stopped by heating to 65° C. for 15 minutes.

The repaired DNA in the resulting reaction mixture can be used directly in PCR reactions without further purification from RC13 enzyme components.

Prior to amplification of the repaired DNA by whole genome amplification, the repaired DNA is purified from the RC13 enzyme mix as follows: a standard phenol/chloroform extraction was performed in a 1.5 µl, followed by a standard chloroform extraction with final purification of the DNA sample using Micro Bio-Spin® chromatography columns (Bio-Rad, cat #732-6223). The column is inverted sharply several times to re-suspend the settled gel and remove bubbles. The tip is snapped off and the column is placed in a 2.0 ml microcentrifuge collection tube. The column is then centrifuged at 800×g for 4 minutes, after which the collection tube is discarded. The column is placed in a clean 1.5 ml microcentrifuge tube and the DNA sample is applied to the column. The column is then centrifuged at 800×g for 4 minutes to elute the DNA sample.

Figure 3:
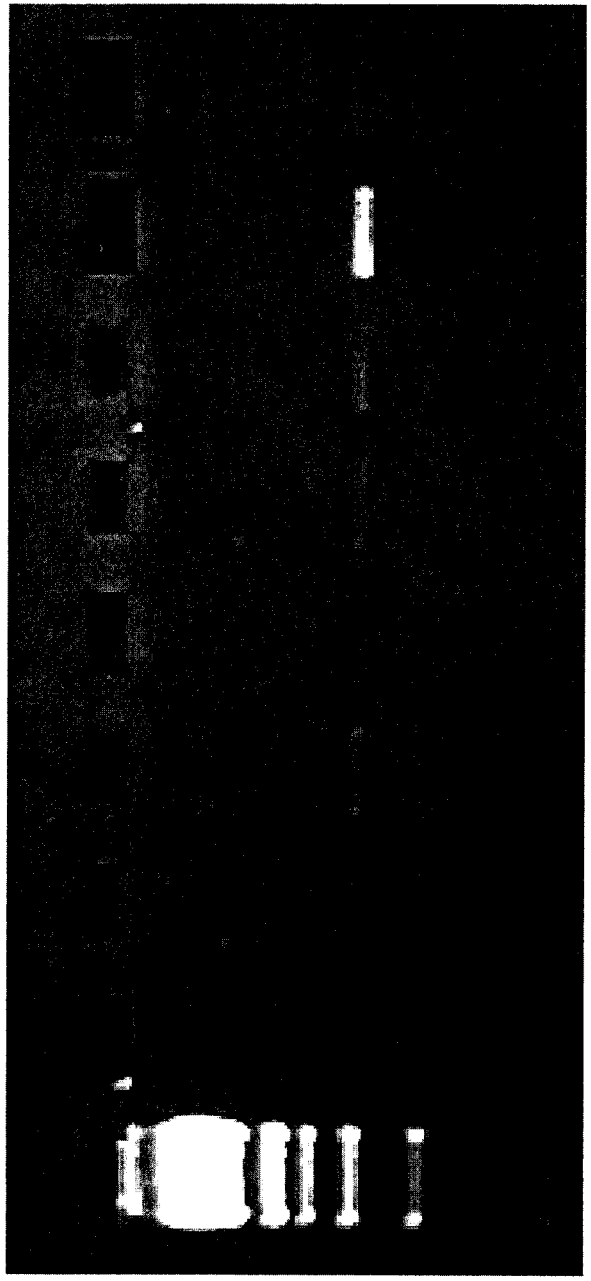
FIG. 3 indicates improved performance of irradiated DNA in human mitochondrial DNA HV2 region PCR following treatment with high concentrations of T4 DNA ligase and 6 other enzymes for 2 hours at 37° C. followed by 12 hours at 16° C. (lane 94) The protocol used for lane 94 is described in detail in Example 1. Even number lanes had 2 ng of irradiated DNA used in the repair reaction and odd numbered lanes had 400 pg of irradiated DNA used in the repair reactions. 5% of the repaired DNA was subsequently used in the HV2 PCR reaction. Lanes 88 and 89 have repair cocktail with low ligase concentration (2 units) and were incubated at 37° C. for 2 hours. Lanes 90 & 91 had low ligase and were incubated at 37° C. for 12 hours. Lanes 92 & 93 had low ligase and were incubated for two hours at 37° C. followed by 12 hours at 16° C. and lanes 94 & 95 had repair cocktail made using high concentration of ligase and were incubated at 37° C. for two hours followed by 16° C. for 12 hours.

The preceding method was used in an experiment which determined that high concentrations of ligase are necessary for efficient repair of irradiated DNA. In FIG. 3 the repair protocol as described above was used in lane 94 and the results indicate effective repair of the DNA.

Example 2: Whole Genome Amplification of Genomic DNA by Multiple Displacement Amplification Using Φ29 Polymerase The following method has been found to be effective for whole genome amplification of DNA:

TABLE 2

Reaction Components for Whole Genome Amplification

| Components | Final Concentration |
|---|---|
| Starting DNA | 1 pg-100 ng |
| Water | NA |
| 10x NEB Φ29 Rxn Buffer, Supplied with polymerase. | 1x |

TABLE 2-continued

Reaction Components for Whole Genome Amplification

| Components | Final Concentration |
|---|---|
| Modified-Random Primers (1 mM) equal part mix o hexamers, heptamers and octamers Custom ordered from IDT-DNA-thiophosphate linkages for the last two 3 prime nucleotides | 50 uM |
| DNTPs (100 mM mix) Stratagene Corp. | 2 mM |
| Φ29 polymerase (10,000 units/ml.)-NEB cat # M0269L | 16 Units |
| Pyrophos-phosphatase (40 u/ml stock)-Amersham cat # E70953Z | 0.008 Units |
| BSA-Acetylated-Ambion Cat # 2612 (20 mg/ml) | 200 ug/ml |
| 0.1M DTT-Invitrogen cat # Y00147 | 5 mM | wherein NEB buffer is 50 mM TRIS-HCl, 10 mM $MgCl_2$, 10 mM $(NH_4)_2SO_4$, 4 mM DTT, pH 7.5 at 25° C.

A sample of DNA is diluted with nuclease-free water to a volume of 62 μl in a 200 μl PCR tube, to which is added 35.0 μl of Mix A (a mixture of 200 μl of 10×NEB, 100 μl of modified-random primer mix (1 mM) and 40 μl of 100 mM DNTP mixture), followed by vortexing and centrifuging to collect all liquid in the bottom of the tube. The mixture is then heated to 95° C. for 5 minutes and allowed to cool to 4° C. using a thermocycler. Then 3.0 μl of Mix B (a mixture of 10,000 units/ml of Φ29 polymerase, 40 units/ml pyrophos-phosphatase, 20 mg/ml BSA-acetylated (Ambion Cat. #2612) and 0.1 M DTT). The reaction mixture is then cycled through a 12 hour thermocycler program as follows:

1. 30° C. for 4 minutes
2. 15° C. for 15 seconds
3. repeat steps 1 and 2 sequentially 150 times
4. 90° C. for 3 minutes
5. maintain at 4° C.

Post amplification processing of the amplified DNA includes fragmentation of the DNA by sonication with a Misonix Sonicator 3000 equipped with a cup horn (Cat #431A) and a cup horn stand (Cat #448), power level setting 10 with a 1 minute process time (30 sec interval on, 30 sec interval off). The PCR tube containing the WGA reaction mixture is placed in a floating foam holder in the cup horn filled ⅓ with water. The resulting post-amplification processed DNA is diluted 1:10 with water and can be used directly in mitochondrial DNA typing PCR reactions, such as those disclosed and claimed in U.S. patent application Ser. Nos. 10/660,998 and 10/807,019, each of which is commonly owned and incorporated herein by reference in its entirety.

Example 3: Inactivation of Contaminating DNA in 029 Polymerase

Figure 4:
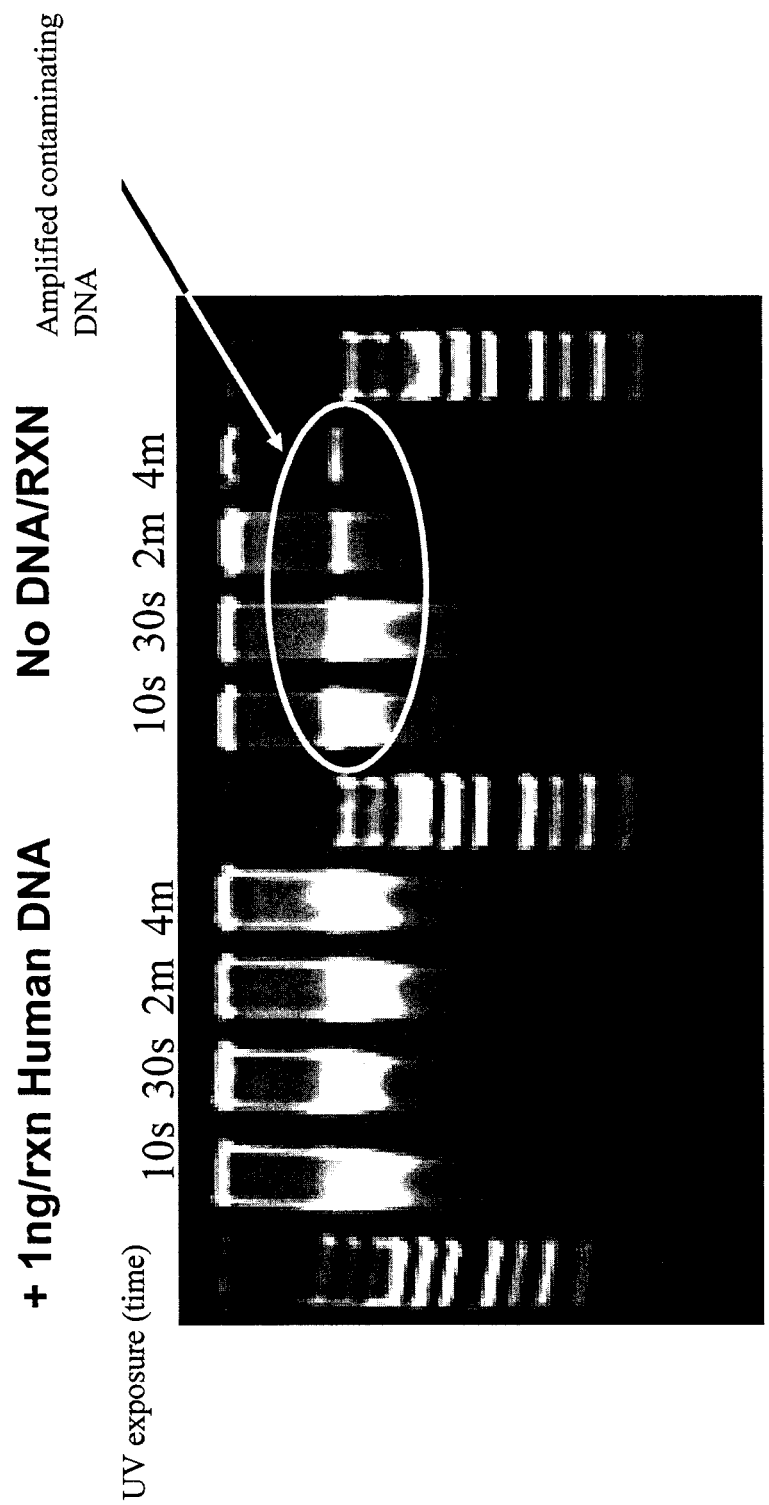
FIG. 4 demonstrates that commercially obtained Φ29 polymerase used for whole genome amplification reactions is contaminated with DNA which can be destroyed by irradiation with ultraviolet light. The left half of the gel shows the effect of irradiating the enzyme preparation for 10 sec, 30 sec, 2 min. and 4 min. prior to amplification of a 1 ng sample of human DNA. The gel indicates that the extent of amplification is essentially equivalent for each of the four reactions. In contrast, the right half of the gel indicates that contaminating DNA is amplified in the absence of expressly added human DNA template, but that this contaminating DNA fails to amplify to the same extent when the Φ29 polymerase preparation is exposed to ultraviolet light for 2 to 4 minutes.

FIG. 4 demonstrates that commercially obtained Φ29 polymerase used for whole genome amplification reactions is contaminated with DNA which can be destroyed by irradiation with ultraviolet light. The left half of the gel shows the effect of irradiating the enzyme preparation for 10 sec, 30 sec, 2 min. and 4 min. prior to amplification of a 1 ng sample of human DNA. The gel indicates that the extent of amplification is essentially equivalent for each of the four reactions. In contrast, the right half of the gel indicates that contaminating DNA is amplified in the absence of expressly added human DNA template, but that this contaminating DNA fails to amplify to the same extent when the Φ29 polymerase preparation is exposed to ultraviolet light for 2 to 4 minutes. This experiment indicates that an added step prior to carrying out a WGA reaction wherein the Φ29 polymerase preparation is irradiated with ultraviolet light to destroy contaminating DNA is a useful addition for a whole genome amplification reaction. It is expected that this step will enable a significant lowering of the concentration (template copy number) of starting template DNA required to carry out a WGA reaction.

Various modifications of the invention, in addition to those described herein, will be apparent to those skilled in the art from the foregoing description. Such modifications are also intended to fall within the scope of the appended claims. Each of the patents, applications, printed publications, and other published documents mentioned or referred to in this specification are incorporated herein by reference in their entirety. Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

What is claimed is:

1. A kit comprising a purified endonuclease, a purified DNA N-glycosylase, a purified AP lyase, a purified DNA polymerase, a purified 3'-diesterase, a purified polynucleotide kinase, a purified large Klenow fragment, a purified DNA ligase, a mixture of random primers comprising an equal part mix of hexamers, heptamers, and octamers with thiophosphate linkages for the last two 3' nucleotides and a mixture of deoxynucleotide triphosphates, wherein the kit optionally further includes a highly processive strand displacing polymerase.

2. The kit of claim 1 further comprising irradiated and non-irradiated DNA controls.

3. The kit of claim 1 further comprising pyrophosphatase.

4. The kit of claim 1 further comprising φ29 polymerase.

5. The kit of claim 1 further comprising dithiothreitol (DTT).

6. The kit of claim 1 further comprising bovine serum albumin (BSA)-acetylated.

7. The kit of claim 1 further comprising glycerol.

* * * * *